US010247722B2

(12) United States Patent
Gavard et al.

(10) Patent No.: US 10,247,722 B2
(45) Date of Patent: Apr. 2, 2019

(54) USE OF COMPOUNDS INHIBITING APELIN / APJ / GP130 SIGNALING FOR TREATING CANCER

(71) Applicants: Centre National de la Recherche Scientifique (CNRS), Paris (FR); Universite Paris Descartes, Paris (FR); Institut National de la Sante et de la Recherche Medicale (INSERM), Paris (FR)

(72) Inventors: Julie Gavard, Paris (FR); Eva-Maria Galan-Moya, Paris (FR)

(73) Assignees: Centre National de la Recherche Scientifique (CNRS), Paris (FR); Universite Paris Descartes, Paris (FR); Institut National de la Sante et de la Recherche Medicale (INSERM), Paris (FR)

( * ) Notice: Subject to any disclaimer, the term of this patent is extended or adjusted under 35 U.S.C. 154(b) by 0 days.

(21) Appl. No.: 15/127,534

(22) PCT Filed: Mar. 20, 2015

(86) PCT No.: PCT/EP2015/055926
§ 371 (c)(1),
(2) Date: Sep. 20, 2016

(87) PCT Pub. No.: WO2015/140296
PCT Pub. Date: Sep. 24, 2015

(65) Prior Publication Data
US 2017/0146518 A1   May 25, 2017

(30) Foreign Application Priority Data

Mar. 20, 2014 (EP) .................................... 14305396
Sep. 2, 2014 (EP) .................................... 14306353

(51) Int. Cl.
| | | |
|---|---|---|
| *G01N 33/53* | (2006.01) | |
| *G01N 33/50* | (2006.01) | |
| *G01N 33/574* | (2006.01) | |
| *A61K 39/395* | (2006.01) | |
| *A61K 48/00* | (2006.01) | |
| *A61K 31/00* | (2006.01) | |
| *C12N 15/113* | (2010.01) | |

(52) U.S. Cl.
CPC .......... *G01N 33/5011* (2013.01); *A61K 31/00* (2013.01); *A61K 39/395* (2013.01); *A61K 48/005* (2013.01); *C12N 15/1138* (2013.01); *G01N 33/5073* (2013.01); *G01N 33/57407* (2013.01); *C12N 2310/14* (2013.01); *G01N 2333/7155* (2013.01); *G01N 2333/726* (2013.01); *G01N 2800/52* (2013.01)

(58) Field of Classification Search
None
See application file for complete search history.

(56) References Cited

U.S. PATENT DOCUMENTS

| | | | | |
|---|---|---|---|---|
| 7,736,646 B2* | 6/2010 | Krieg | ..................... | C07K 16/18 |
| | | | | 424/133.1 |
| 2008/0182779 A1* | 7/2008 | Ashley | ............... | A61K 38/1709 |
| | | | | 424/133.1 |
| 2010/0221255 A1* | 9/2010 | Cuttitta | .................. | C07K 14/47 |
| | | | | 424/139.1 |
| 2011/0191868 A1 | 8/2011 | Gupta et al. | | |

FOREIGN PATENT DOCUMENTS

| | | |
|---|---|---|
| WO | WO 2010/043037 | 4/2010 |
| WO | WO 2013/153049 | 10/2013 |

OTHER PUBLICATIONS

Doranz et al (AIDS Res Hum Retroviruses, 2001, 17(6): Abstract).*
Mack et al (Am J Phisiol Endocrinol Metab, 2009, 297: E735-E748).*
Evans et al (Journal of Neurochemistry, 2001, 77: 476-485).*
Mercier et al (JBC, 2002, 277(47): 44925-4493).*
Al-Hajj et al., *Prospective identification of tumorigenic breast cancer cells*, 100(7) PNAS 3983-3988 (Apr. 1, 2003).
Bao et al., *Glioma stem cells promote radioresistance by preferential activation of the DNA damage response*, 444, Letters 756-760 (Dec. 7, 2006).
Berta et al., *Apelin Expression in Human Non-small Cell Lung Cancer*, 5(8) Journal of Thoracic Oncology 1120-1129 (Aug. 2010).
Charest et al., *Monitoring agonist-promoted conformational changes of β-arrestin in living cells by intramolecular BRET*, 6(4) EMBO Reports 334-340 (2005).
Chautard et al., *Akt signaling pathway: a target for radiosensitizing human malignant glioma*, 12(5) Neuro-Oncology 434-443 (2010).
Chun et al., *Apelin signaling antagonizes Ang II effects in mouse models of atherosclerosis*, 118(10) The Journal of Clinical Investigation 3343-3354 (Oct. 2008).

(Continued)

*Primary Examiner* — Sean E Aeder
(74) *Attorney, Agent, or Firm* — Buchanan Ingersoll & Rooney PC

(57) ABSTRACT

Today, despite current advances in combinatorial therapies such as surgery, radiotherapy and chemotherapy, aggressive cancers remain fatal. Cancer stem-like cells (CSCs) may account for chemotherapy resistance and thus represent a promising therapeutic target. In this context, the present inventors identified essential intracellular pathways favoring the self-renewal and survival of CSCs. More precisely, the present inventors showed that the cytokine co-receptor GP130 acts as a co-receptor for Apelin/APJ signaling and that the interaction of Apelin with APJ/GP130 activates a dual signaling pathway involving the Akt/mTOR and STAT3 transcription factor, thereby promoting CSCs survival and self-renewal. They therefore propose to block these pathways in order to treat patients suffering from tumors containing CSCs, such as glioblastomas. In another aspect, the invention relates to the use of the Apelin expression level for evaluating the survival probability of a subject suffering from glioblastoma.

10 Claims, 35 Drawing Sheets

Figure 1:
Figure 1:
Figure 1:

Specification includes a Sequence Listing.

(56) References Cited

OTHER PUBLICATIONS

Crocker et al., *Serum angiogenic profile of patients with glioblastoma identifies distinct tumor subtypes and shows that TIMP-1 is a prognostic factor*, 13(1) Neuro-Oncology 99-108 (2011).

Dahlrot et al., *What is the clinical value of cancer stem cell markers in gliomas?*, 6(3) Int. J. Clin. Exp. Pathol. 334-348 (2013).

Ellington et al., *In vitro selection of RNA molecules that bind specific ligands*, 346 Nature 818-822 (Aug. 30, 1990).

Fisher et al., *Epidemiology of Brain Tumors*, 25(4) Neurologic Clinics 867-890 (Nov. 2007) (abstract only).

Galan-Moya et al., *Feeding the hungry enemy; An endothelial recipe for glioma stem cells*, 10(15) Cell Cycle 1-2 (Aug. 1, 2011).

Galan-Moya et al., *Secreted factors from brain endothelial cells maintain glioblastoma stem-like cell expansion through the mTOR pathway*, EMBO Reports 1-7 (2011).

Kälin et al., *Dissecting the role of Apelin Signaling in Gliomagenesis*, 61(Suppl. 1) S214 (Jul. 1, 2013).

Kälin et al., *Paracrine and autocrine mechanisms of apelin signaling govern embryonic and tumor angiogenesis*, 305 Developmental Biology 599-614 (2007).

Kidoya et al., *The apelin/APJ system induces maturation of the tumor vasculature and improves the efficiency of immune therapy*, 31 Oncogene 3254-3264 (2012).

Kim et al., *Phosphorylation of EZH2 Activates STAT3 Signaling via STAT3 Methylation and Promotes Tumorigenicity of Glioblastoma Stem-like Cells*, 23 Cancer Cell 839-852 (Jun. 10, 2013).

Köhler et al., *Continuous cultures of fused cells secreting antibody of predefined specificity*, 256 Nature 495-497 (Aug. 7, 1975).

Lee et al., *Characterization of Apelin, the Ligand for the APJ Receptor*, 74(1) J. Neurochem 34-41 (2000).

Masri et al., *Apelin (65-77) activates p70 S6 kinase and is mitogenic for umbilical endothelial cells*, The FASEB Journal 1-26 (Dec. 2016) (published online 2004).

Macaluso et al., *Discovery of a Competitive Apelin Receptor (APJ) Antagonist*, 6 ChemMedChem 1017-1023 (2011).

Macaluso et al., *Exploring the 'RPRL' Motif of Apelin-13 through Molecular Simulation and Biological Evaluation of Cyclic Peptide Analogues*, 5 ChemMedChem 1247-1253 (2010).

Nakauchi et al., *Quantitative Assessment of the Stem Cell Self-Renewal Capacity*, 938 Annals New York Academy of Sciences 18-25 (2001).

O'Carroll et al., *The apelin receptor APJ: journal from an orphan to a multifaceted regulator of homeostasis*, 219(1) Society for Endocrinology R13-R35 (2013).

Patru et al., *CD133, CD15/SSEA-1, CD34 or side populations do not resume tumor-initiating properties of long-term cultured cancer stem cells from human malignant glio-neuronal tumors*, 10(66) BMC Cancer 1-11 (2010).

Piccirillo et al., *Bone morphogenetic proteins inhibit the tumorigenic potential of human brain-tumor-initiating cells*, 444(7) Letters 761-765 (Dec. 2006).

Pitkin et al., *International Union of Basic and Clinical Pharmacology. LXXIV. Apelin Receptor Nomenclature, Distribution, Pharmacology and Function*, 63(3) Pharmacology Reviews 331-342 (2010).

Pitkin et al., *Modulation of the apelin/APJ system in heart failure and atherosclerosis in man*, 160 British Journal of Pharmacology 1785-1795 (2010).

Rayalam et al., *Emerging Role of Apelin as a Therapeutic Target in Cancer: A Patent Review*, 6(3) Anti-Cancer Drug Discovery 367-372 (2011) (abstract only).

Shenoy, *Visualizing G Protein-Coupled Receptor Signalsomes Using Confocal Immunofluorescence Microscopy*, 756 Methods in Molecular Biology 333-342 (Jul. 1, 2011).

Singh et al., *Identification of human brain tumour initiating cells*, 432 Nature 396-401 (Nov. 18, 2004) (abstract only).

Thomson et al., *Method for Measurement of Self-Renewal Capacity of Clonogenic Cells from Biopsies of Metastatic Human Malignant Melanoma*, 42 Cancer Research 4606-1613 (Nov. 1982).

Verhaak et al., *Integrated Genomic Analysis Identifies Clinically Relevant Subtypes of Gliobastoma Characterized by Abnormalities in PDGFRA, IDH1, EGFR, and NF1*, 17 Cancer Cell 98-110 (Jan. 19, 2010).

Weksler et al., *Blood-brain barrier-specific properties of a human adult brain endothelial cell line*, 19(13) FASEB Journal 1872-1874 (2005).

Yan et al., *The Evolving Landscape of Brain Tumor Cancer Stem Cells*, 26(6) Curr Opin Neurol. 701-707 (Dec. 2013).

Wang et al., *Targeting Interleukin 6 Signaling Suppresses Glioma Stem Cell Survival and Tumor Growth*, 27 Stem Cells 2393-2404 (2009).

Zhou et al., *Activation of the PTEN/mTOR/STAT3 pathway in breast cancer stem-like cells is required for viability and maintenance*, 104(41) PNAS 16158-16163 (Oct. 9, 2007).

European Search Report dated Sep. 3, 2014, in corresponding EP Patent Application 14 30 5396.

International Search Report dated Jan. 1, 2015, in corresponding PCT Application No. PCT/EP2015/055926.

\* cited by examiner

A. Secreted Growth Factors 1 2 3 4 5 6 7 8 9

1. ADM / 2. Apelin / 3. CTGF / 4. Follistatin-like 1 / 5. Pentraxtin related protein 3 / 6. IGF-BP7 / 7. MIF / 8. TGFb2 / 9. Galectin 1

B. Proteases 1 2 3 4 5 6

1. Cystatin C / 2. Pai 1 / 3. MMP1 / 4. Serine protease 23 / 5. Cathepsin B / 6. Serglycin C. Extracellular matrix 1 2 3 4 5 6 7

1. Galectin 3 binding protein / 2. Fibronectin / 3. Thrombospandin 1 / 4. Fibulin 3 / 5. HSPG2 / 6. Laminin 5 / 7. Edil 3

A

B

C

D

E

F

G

A

B  #10

C

D

E

F

A

B

C

D i

USE OF COMPOUNDS INHIBITING APELIN / APJ / GP130 SIGNALING FOR TREATING CANCER

BACKGROUND OF THE INVENTION

Increasing evidence suggests that initial cancer development is due to a rare population of cells, termed cancer stem cells (CSCs) (also known as "tumor-initiating cells", or "tumor side-populations", or "cancer stem-like cells") that are able to initiate and sustain this disease. These cells have indeed been demonstrated to be responsible for tumorigenesis, cancer metastasis, and cancer reoccurrence in particular cancers. Cancer stem cells have self-renewal capacity and they can differentiate into multiple cell types, although the equilibrium between self-renewal and differentiation potential shifts towards enhanced self-renewal, leading to limited differentiation capacity.

Conventional chemotherapies and radiotherapies are known to kill differentiated or differentiating cells, which form the bulk of the tumor (but that are unable to regenerate tumors). However, the population of cancer stem cells remains unaffected by said treatments and often causes a relapse of the disease.

In this context, it is imperative that anti-cancer therapies include strategies affecting preferentially CSCs. As a matter of fact, by targeting cancer stem cells, it will be possible to treat patients with aggressive and non-resectable tumors, as well as preventing tumor metastasis and recurrence.

Moreover, the identification of molecules that target CSCs in a selective manner, i.e., while sparing non-cancerous or normal stem cells, is critical to provide new anti-cancer drugs having few side effects.

It is therefore important to identify and validate pathways that are selectively implicated in cancer stem cell self-renewal and survival. Yet, though multiple pathways underlying properties of embryonic or adult stem cells have been already elucidated, few pathways have been identified for cancer stem cell self-renewal and survival.

Glioblastoma multiforme (GBM) is the most frequent and malignant primary tumor of the central nervous system in adults (60 000 cases/year in Europe and US). It has been proposed that GBM tumors derive from a small fraction of cells that constitute a reservoir of self-sustaining cells with the exclusive ability to self-renew and maintain the tumor, called glioblastoma stem-like cells (GSCs) (Singh et al, 2003). Regardless of the brain tumor ontogeny, GSCs might be involved in resistance to radiotherapies and contribute to tumor recurrence and aggressiveness (Bao et al, 2006). Furthermore, alterations in GSC levels affect tumor growth in experimental models of glioma (Piccirillo et al, 2006). Very few therapeutic protocols exist for this disease and, despite major clinical efforts, median survival rates from the time of diagnosis range between 12 and 15 months, and fewer than 3% of patients survive more than 5 years (Fisher et al, 2007).

In this context, the inventors identified pathways that regulate specifically the self-renewal and survival of CSCs—and in particular of GSCs. They now propose to screen for compounds that are able to block specifically these pathways, said compounds being efficient for treating patients with aggressive tumors, with minor side effects.

More precisely, the inventors highlight for the first time the essential interplay between the Akt/mTOR and STAT3 signaling pathways in self-renewal and survival of cancer stem-like cells such as GSCs. These pathways are activated by the endothelial-produced Apelin which operates through the APJ and GP130 membrane co-receptors. The results below show that the Apelin/APJ/Gp130 signaling nexus operates as a niche-specific signal that sustains tumour initiation and progression, suggesting that Apelin is a druggable paracrine factor in glioblastoma. As a matter of fact, compounds impairing the protein interaction of Apelin on its coreceptors APJ/GP130 (thereby inhibiting the Akt/mTor and STAT3 pathways) in GSCs lead to their apoptosis and thus refrain tumor progression and recurrence.

LEGENDS OF THE FIGURES

FIG. 1. Analysis of the secretome content.

Figure 2:
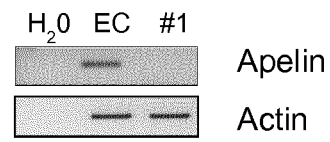
Figure 2:
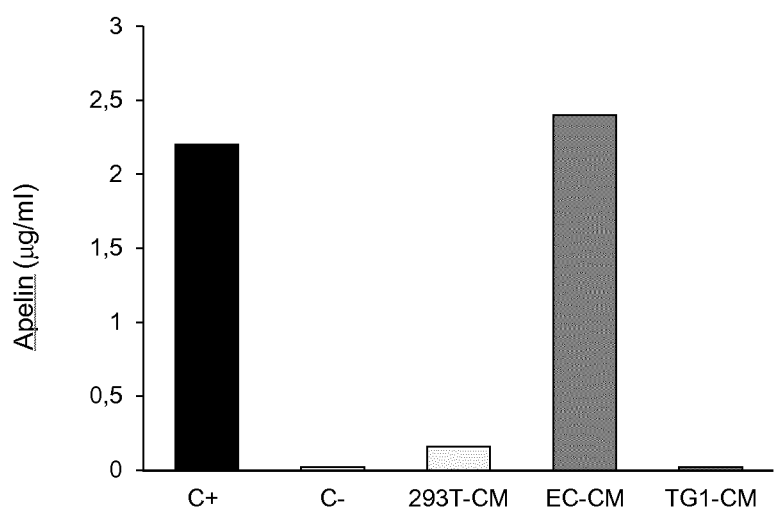
Figure 2:
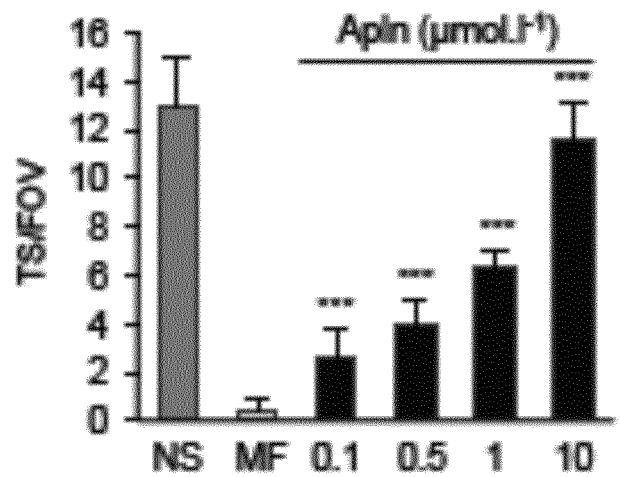
Figure 2:
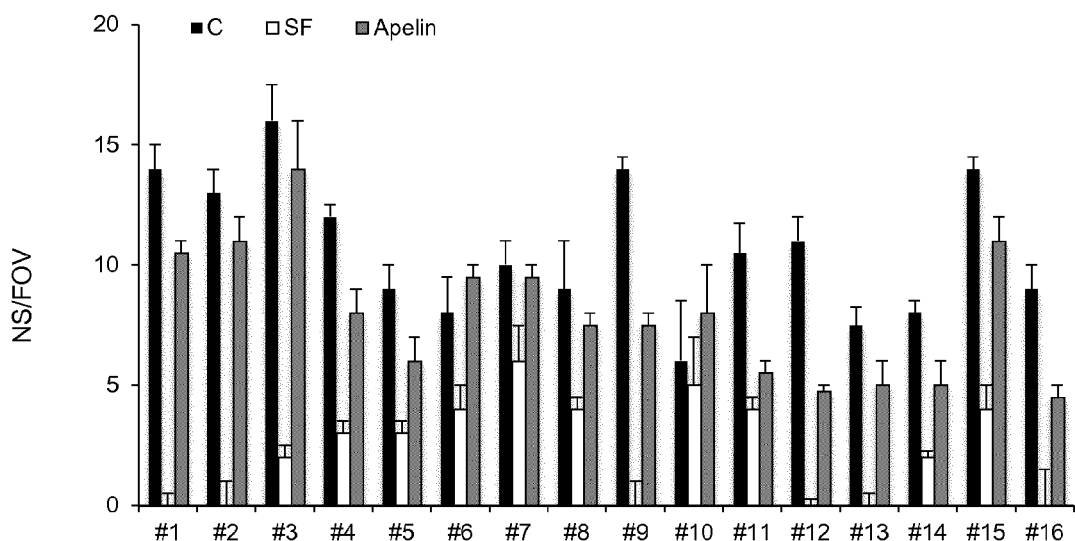
Figure 2:
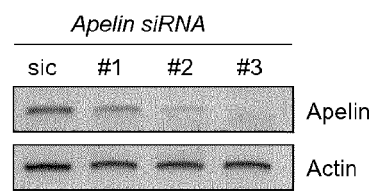
Figure 2:
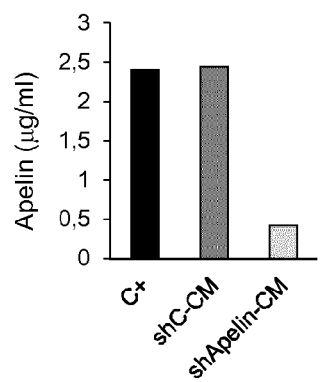
Figure 2:
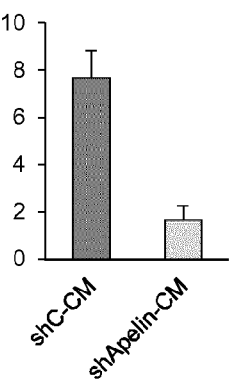

FIG. 2. Endothelial production of Apelin regulates GSC integrity. A. RT-PCR for Apelin and Actin as a control in mRNA prepared from brain endothelial cells (EC) and patient-derived GSC#1. B. Apelin secretion was measured by ELISA in positive and negative templates (C+ and C−, respectively), and in HEK-293T (293T), EC and GSC#1 (TG1) conditioned media (CM). C-D. Quantification of neurosphere formation per field of view (NS/FOV) of GSC#1 grown in complete media (NS34 or C), in deprived medium (SF) or in SF supplemented with recombinant Apelin (Apelin) at 1 µM, unless specified. E. EC received non-silencing siRNA (sic) or siRNA targeting Apelin and Apelin mRNA levels were checked 3 days later by RT-PCR. F. Stable ECs expressing either a non-silencing shRNA (shC) or shRNA targeting Apelin were used to prepared conditioned media and secreted Apelin levels were estimated by ELISA. G. Quantification of neurosphere formation per field of view (NS/FOV) of GSC#1 grown in CM prepared from ECs that received either shRNA control or targeting Apelin.

Figure 3:
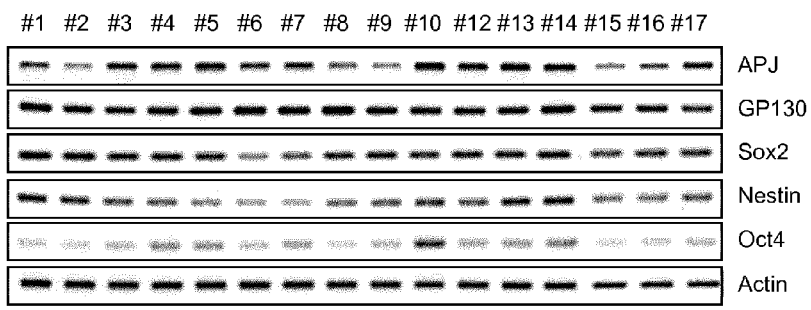
Figure 3:
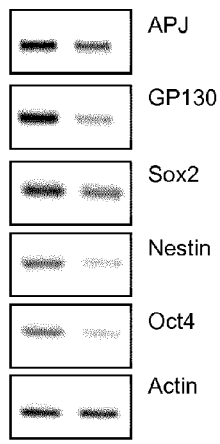
Figure 3:
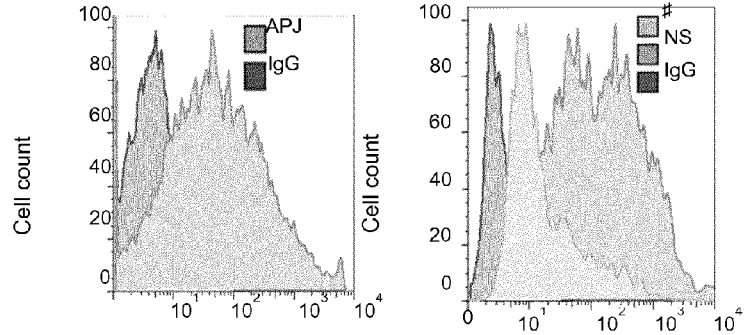
Figure 3:
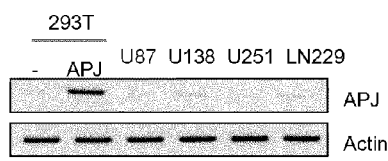
Figure 3:
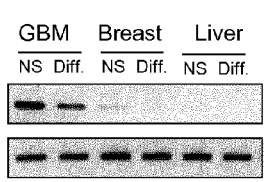
Figure 3:
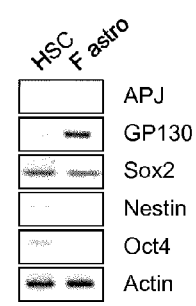

FIG. 3. APJ profile of expression. A. mRNA levels were analyzed by RT-PCR in 16 GSCs for APJ, GP130, Sox2, Nestin, Oct4 and Actin. B. mRNA levels were analyzed by RT-PCR in GSC#10, either grown as neurosphere (NS) or induced in differentiation (Diff.) for APJ, GP130, Sox2, Nestin, Oct4 and Actin. C. APJ expression was measured by indirect immunofluorescence and flow cytometry in GSC NS (green) or Diff (#, pink). Isotype control is shown in blue. D-F. mRNA levels were analyzed by RT-PCR for the indicated primers in GBM cell lines (U87, U138, U251 and LN229), mock or APJ-HA-transfected HEK-293T cells (293T), cancer stem-like cells isolated from GBM, Breast and Liver Cancer either grown as NS or Diff, human normal hematopoietic stem cells (HSC) and human fetal astrocytes (F Astro).

Figure 4:
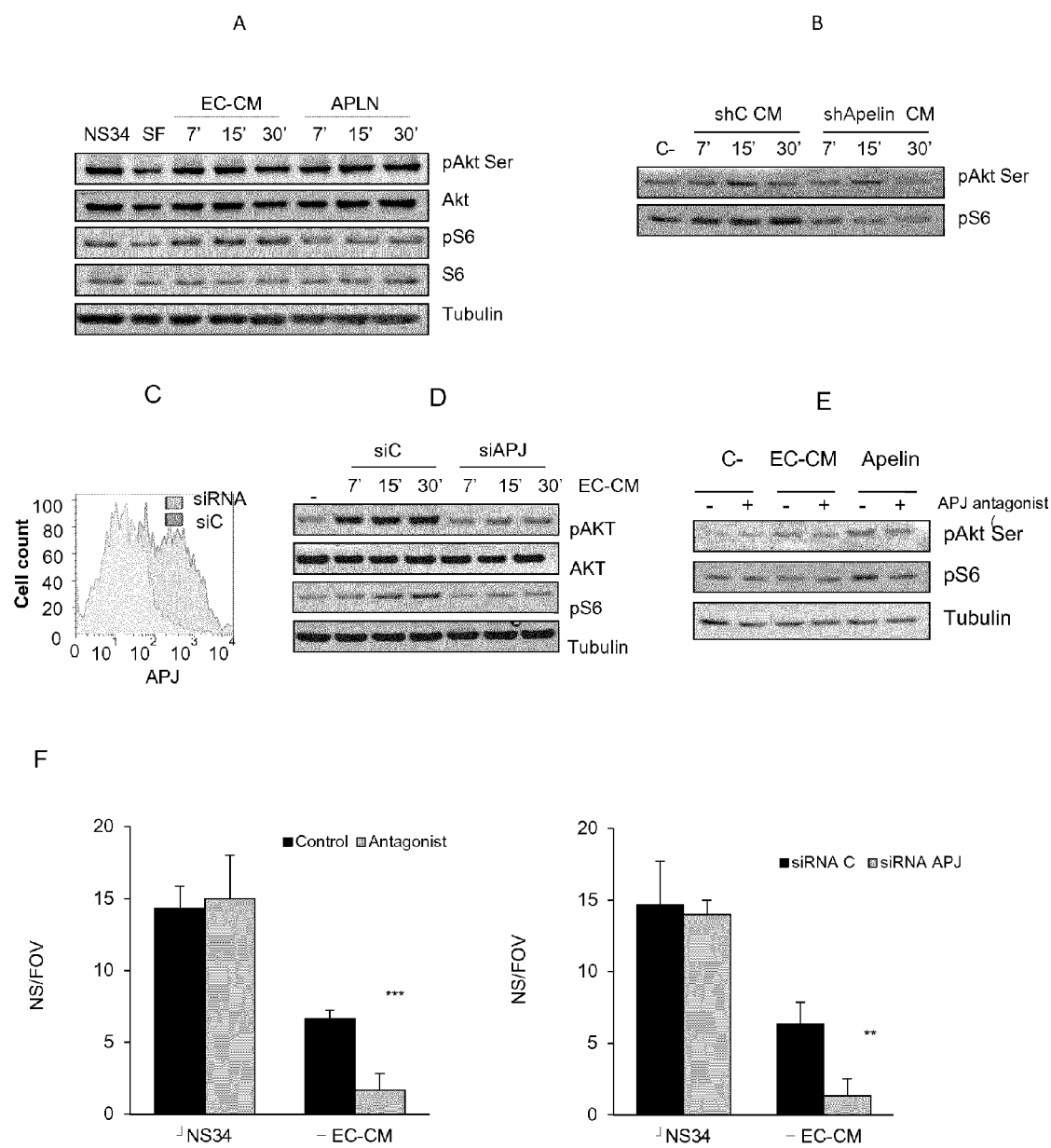
Figure 4:
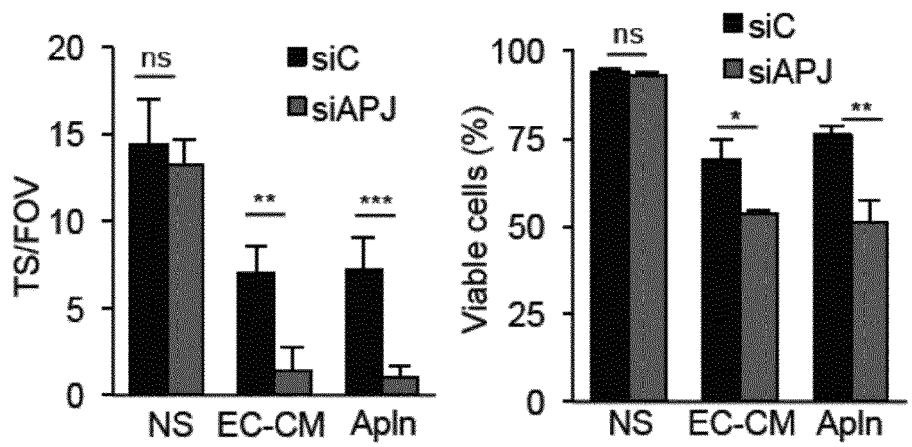
Figure 4:
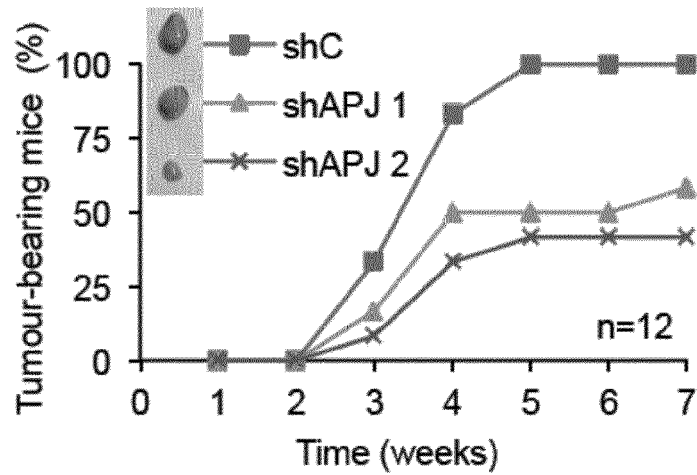
Figure 4:
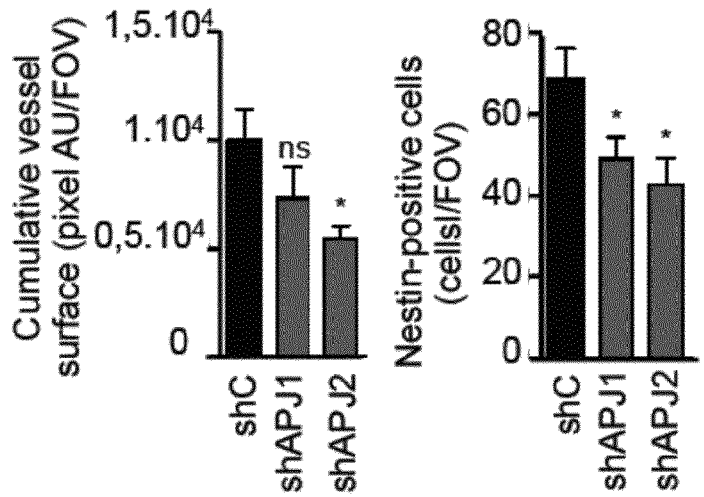

FIG. 4. Endothelial Apelin maintains GSC integrity through APJ signaling to mTOR. A-B. Western-blot analysis for phosphorylated Akt on Ser 473 (pAkt Ser), pS6, Total Akt, Total S6 and Tubulin in GSC#1 treated with complete media (NS34), deprived medium (SF), endothelial cell-conditioned media (EC-CM), or SF supplemented with Apelin (1 µM, APLN), for the indicated times. Alternatively, GSC#1 received EC-CM prepared from non-silencing shRNA (shC) or shRNA targeting Apelin. C-D. GSC#1 received non-silencing siRNA (siC) or siRNA targeting APJ. Knockdown efficiency was estimated by indirect immunofluorescence and flow cytometry (C) and GSC#1 were cultured with the resulting EC-CM for the indicated times, and analyzed by western-blots using the indicated antibodies (D). E. GSC#1 were pre-treated with APJ antagonist 45 min prior EC-CM or Apelin stimulation and protein lysates were analyzed by western-blots. F. Neurosphere assay was conducted in GSC#1 treated with siRNA as in (D) or with pharmacological APJ inhibitor as in (E), and number of neurosphere per field of view (NS/FOV) was quantified. Tumoursphere formation per field of view (TS/FOV) and trypan blue exclusion (Viable cells %) were also quantified (G). H-I. GSCs were stably transfected with non-targeting shRNA (shC) and two shRNA targeting APJ (shAPJ1 and shAPJ2) and implanted in nude mice. Appearance of palpable tumours was scored at the indicated times (H). Frozen sections from resulting tumours were stained for blood vessels (PECAM), or Nestin and nuclei (DAPI). Quantification of both staining is shown (I). Scale bar: 40 μm. Data represent mean+sem on n=3 experiments. T-test: *$P<0.05$; **$P<0.01$.

Figure 5:
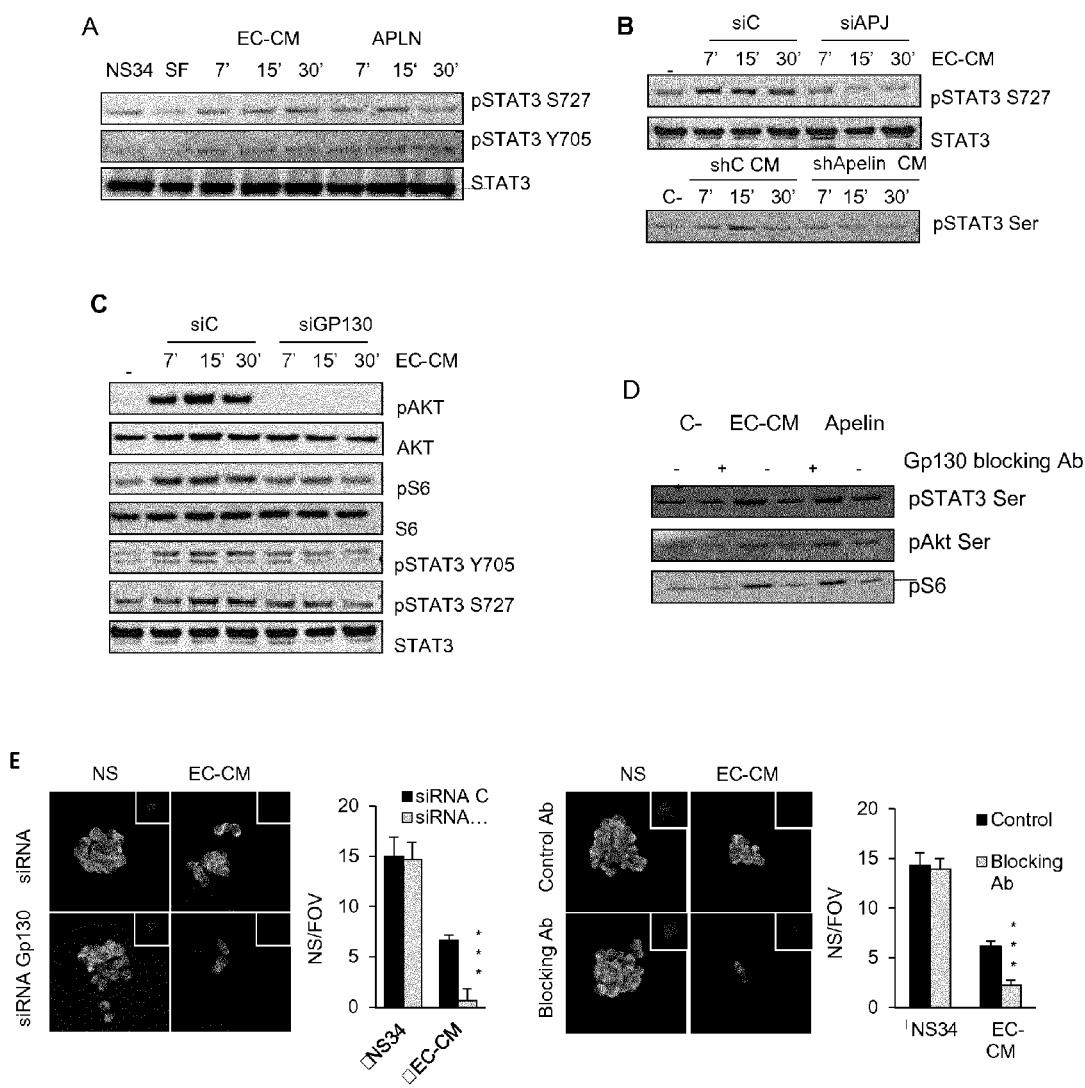

FIG. 5. Endothelial Apelin triggers GP130/STAT3 activation. A. Western-blot analysis for pY-STAT3, pS-STAT3 and Total STAT3 in GSC#1 treated with complete media (NS34), deprived medium (SF), endothelial cell-conditioned media (EC-CM), or SF supplemented with Apelin (1 μM), for the indicated times. B. GSC#1 received non-silencing siRNA (sic) or siRNA targeting APJ. GSC#1 were treated with EC-CM and analyzed by western-blots using the indicated antibodies (upper panel). Alternatively, GSC#1 received EC-CM prepared from non-silencing shRNA (shC) or shRNA targeting Apelin (lower panel). C. GSC#1 received non-silencing siRNA (siC) or siRNA targeting GP130, were stimulated with EC-CM three days later, and protein lysates were analyzed by western-blots, using the indicated antibodies. D. GSC#1 were pre-treated with GP130-blocking antibody 45 min prior EC-CM or Apelin stimulation and protein lysates were analyzed by western-blots. E. Neurosphere assay was conducted in GSC#1 treated with siRNA as in (C) or with GP130-blocking antibody as in (D).

Figure 6:
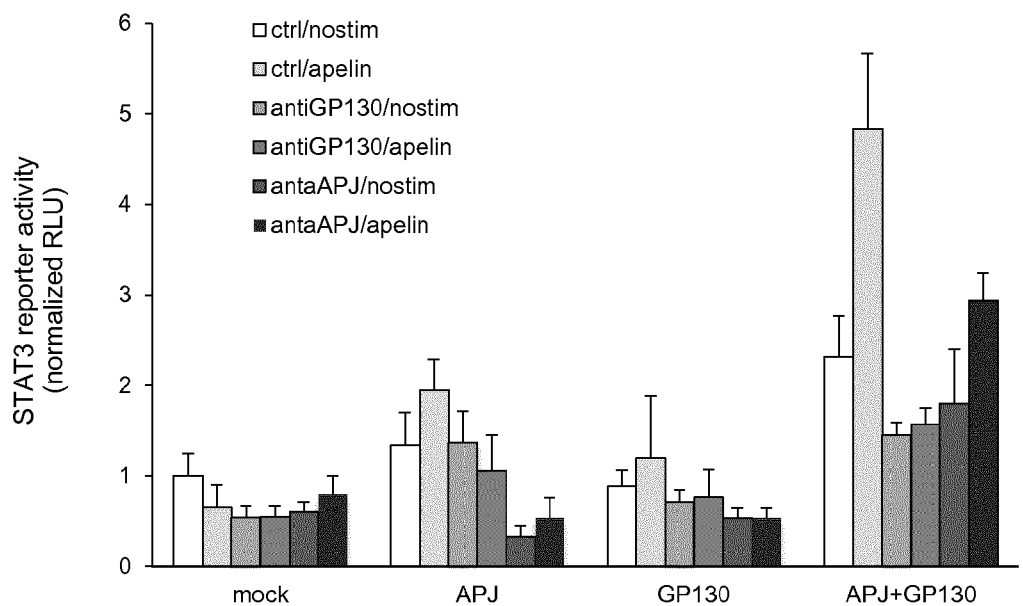
Figure 6:
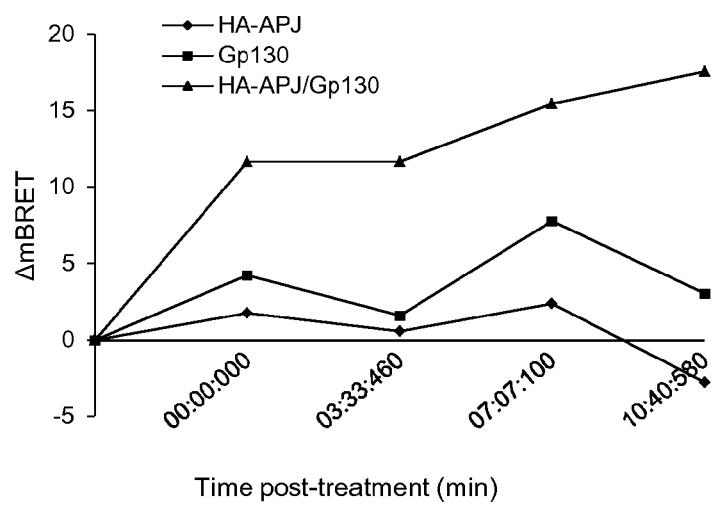
Figure 6:
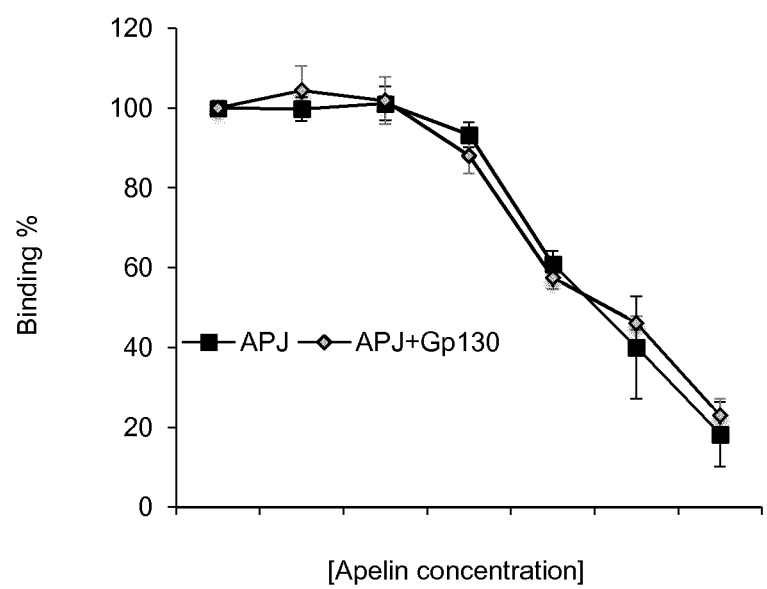
Figure 6:
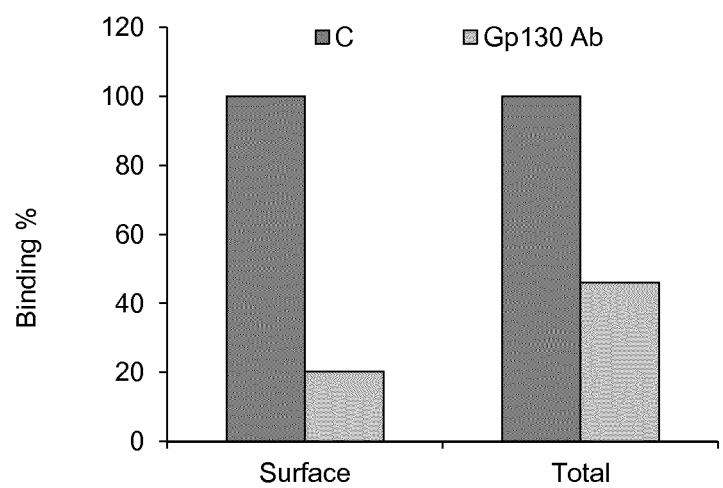
Figure 6:
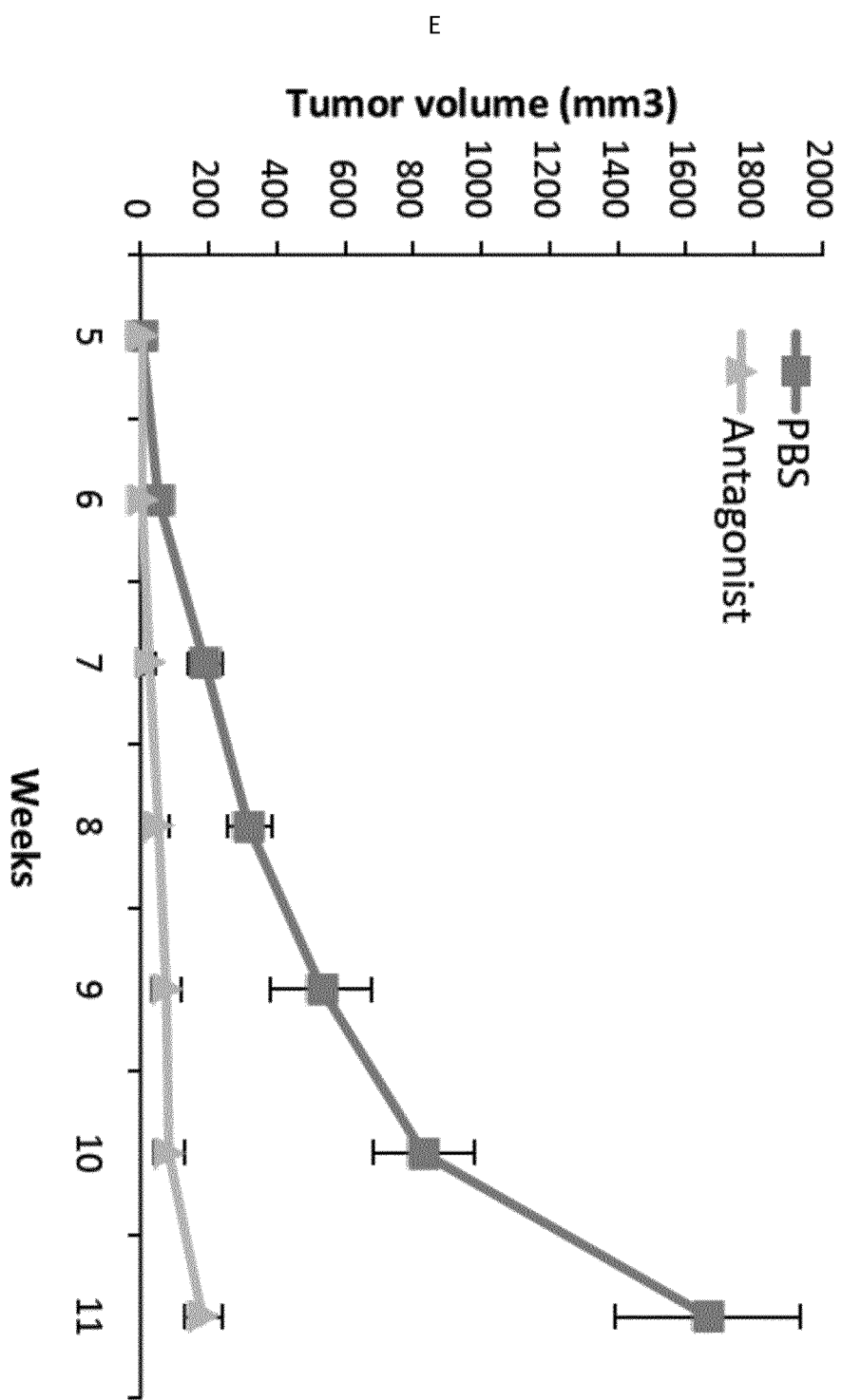

FIG. 6. Apelin co-opts GP130 and APJ. A. STAT3 reporter activity was measured through luciferase-based assay in HEK-293T cells transfected with mock, APJ-, GP130-expression plasmid and both. Cells were not stimulated (nostim) or treated with Apelin (1 μM) for 6 h, following vehicle (ctrl), APJ inhibitor or GP130-blocking antibody 45 min pre-treatment. B. BRET analysis was conducted in HEK-293T cells transfected with mock, APJ-, GP130-expression plasmid and both. Cells received Apelin (1 μM) for the indicated times, and data are presented as Delta mBRET on one representative experiment. C-D. Binding experiment as described in materials and methods in HEK-293T cells transfected with either APJ- or APJ- and GP130-expression plasmids (C) and in GSC#1 from membrane preparation (surface) or total lysates (D). E. Evolution of the tumor volume of glioblastoma xenograft mouse model that were obtained by subcutaneous injection of GSCs and were then treated with either PBS or an APJ antagonist (MM54).

Figure 7:
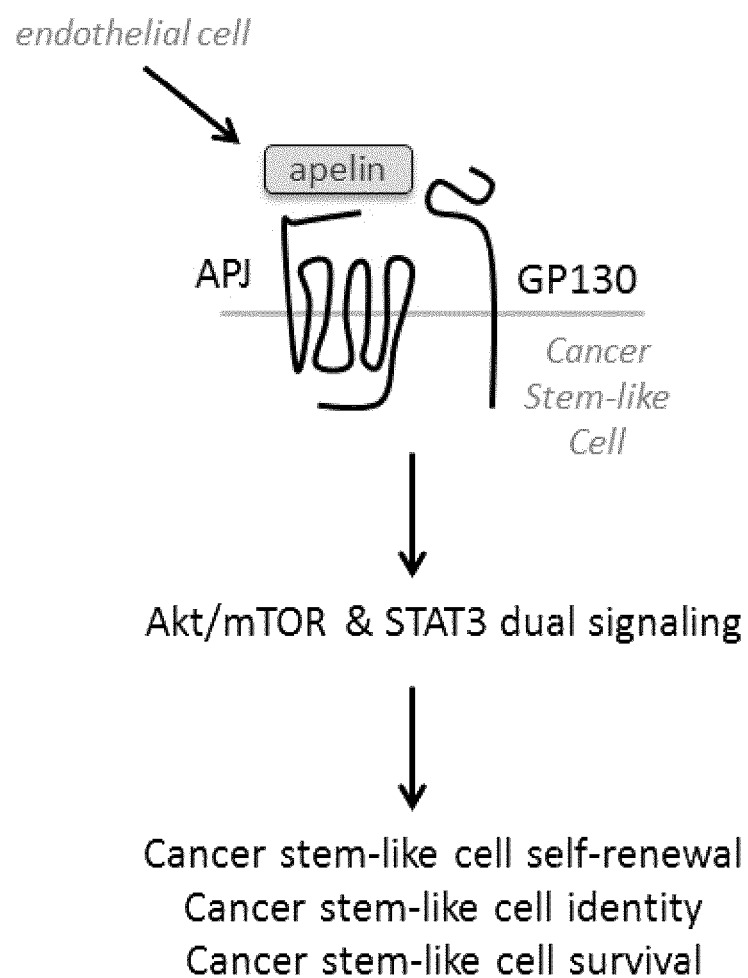

FIG. 7. Scheme of the signaling pathways involved in CSCs properties. The present inventors identified that endothelial-produced Apelin operates through APJ and GP130 membrane receptors, and subsequently activates the Akt/mTOR and STAT3 intracellular signaling pathways. This molecular network is functional in cancer stem-like cells, and promotes self-renewal and survival, to ultimately maintain their integrity.

Figure 8:
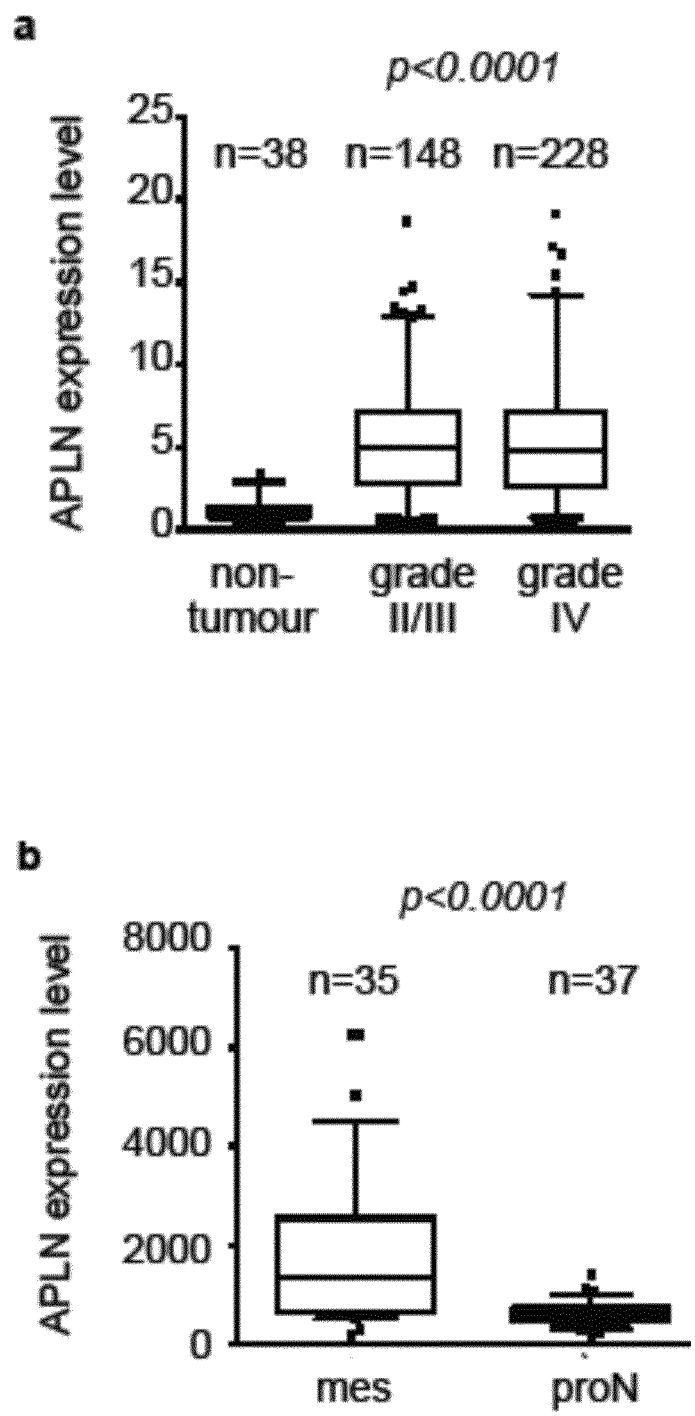
Figure 8:
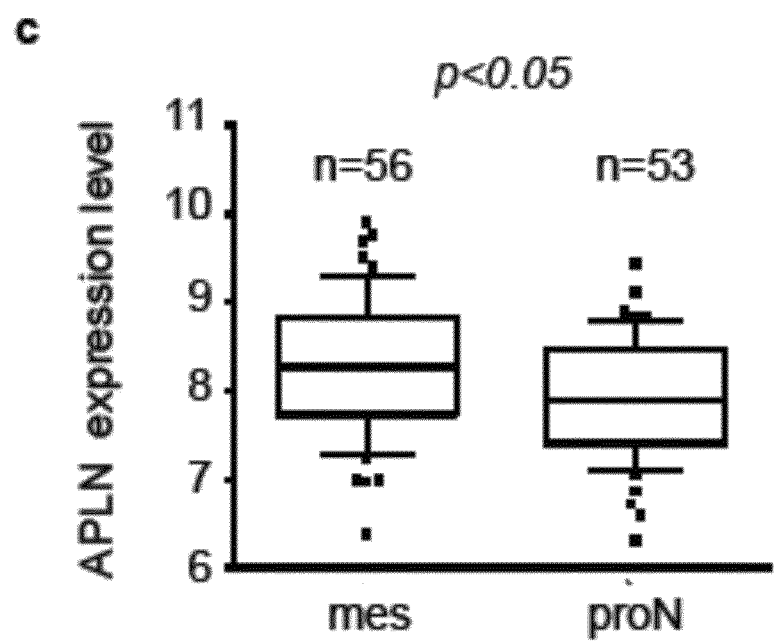
Figure 8:
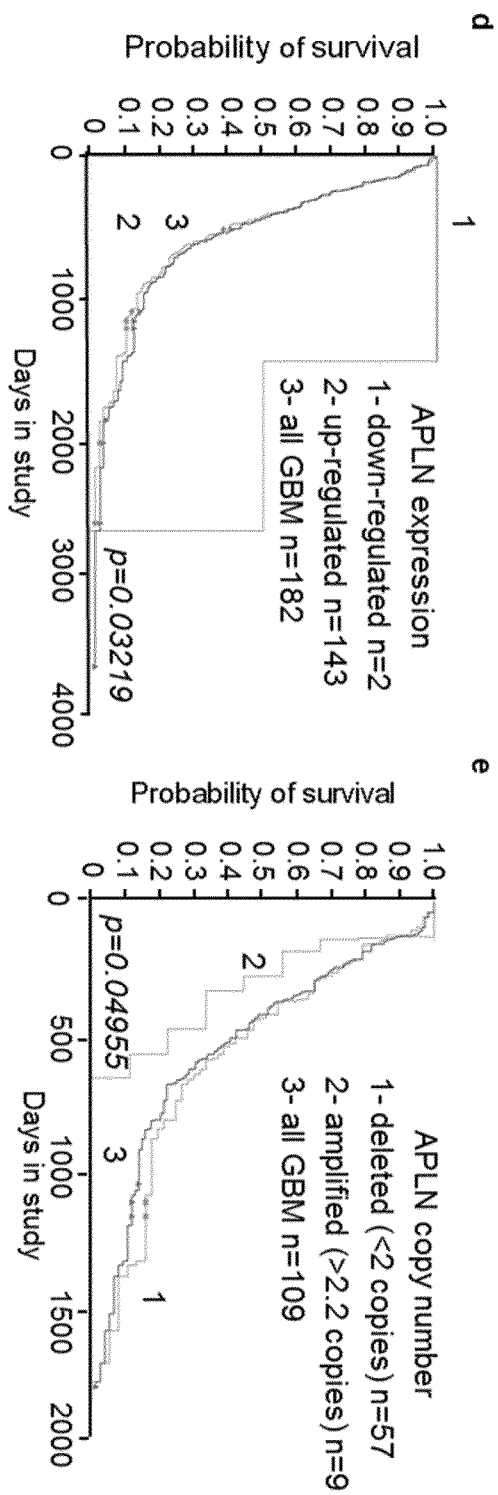

FIG. 8. Apelin expression is elevated in human glioblastoma. a. Box-plot showing Apelin mRNA levels (APLN expression) in control (non-tumor) brain tissues, astrocytomas (World Health Organization [WHO] grades II-III), and glioblastomas (GBM; WHO grade IV) derived from the National Cancer Institute's Repository for Molecular Brain Neoplasia Data (REMBRANDT) database. b-c. Box-plot showing Apelin mRNA levels in GBM from mesenchymal (mes) or proneural (proN) subtypes. d-e. Kaplan-Meier survival plot based on patient subgroup from REMBRANDT database comprising only GBM patients. In each graph, patient samples have been divided into APLN low-expressing tumors (downregulated) and APLN high-expressing tumors (up-regulated) or alternatively, regarding APLN copy number. For both plots all GBM can be seen.

Figure 9:
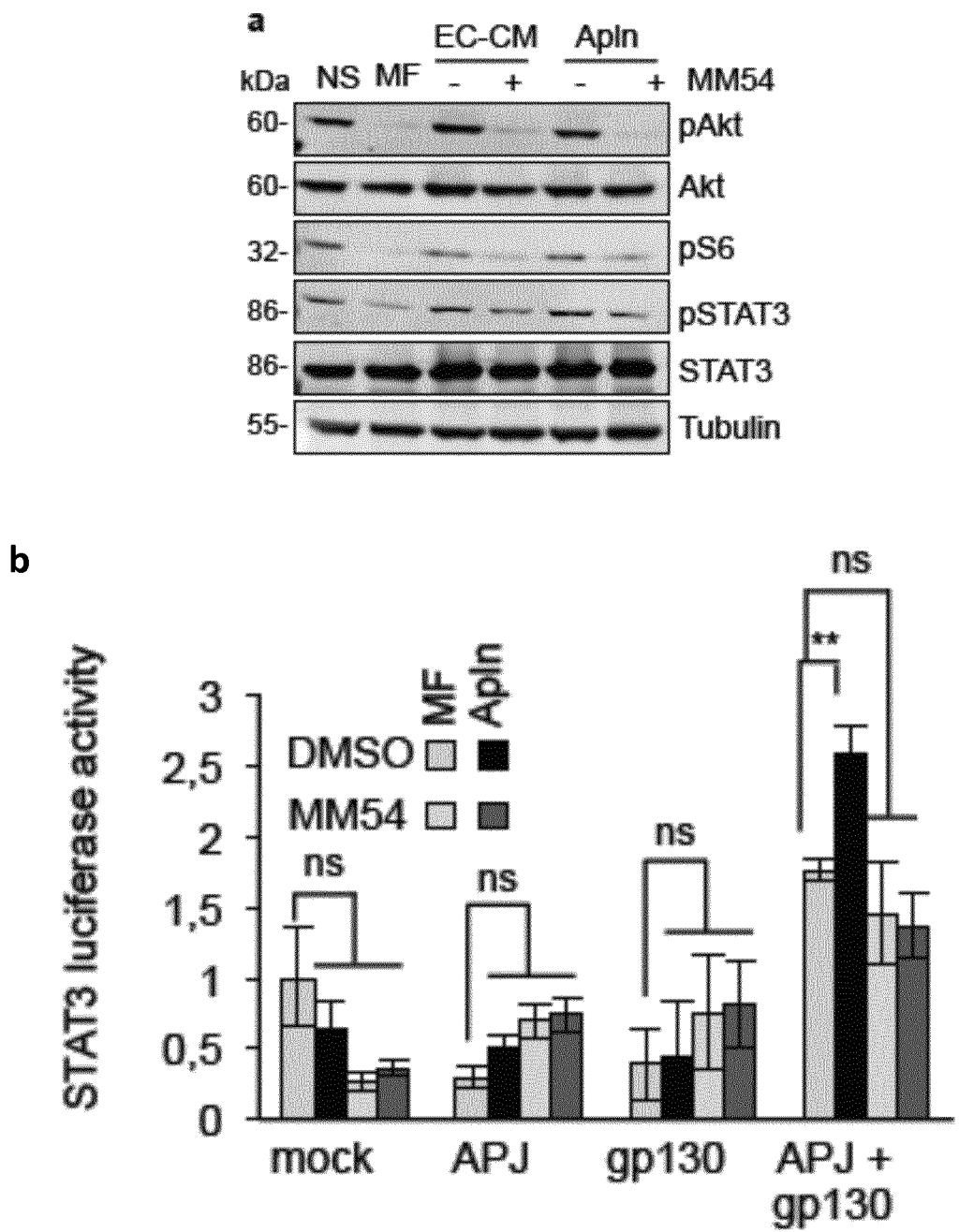
Figure 9:
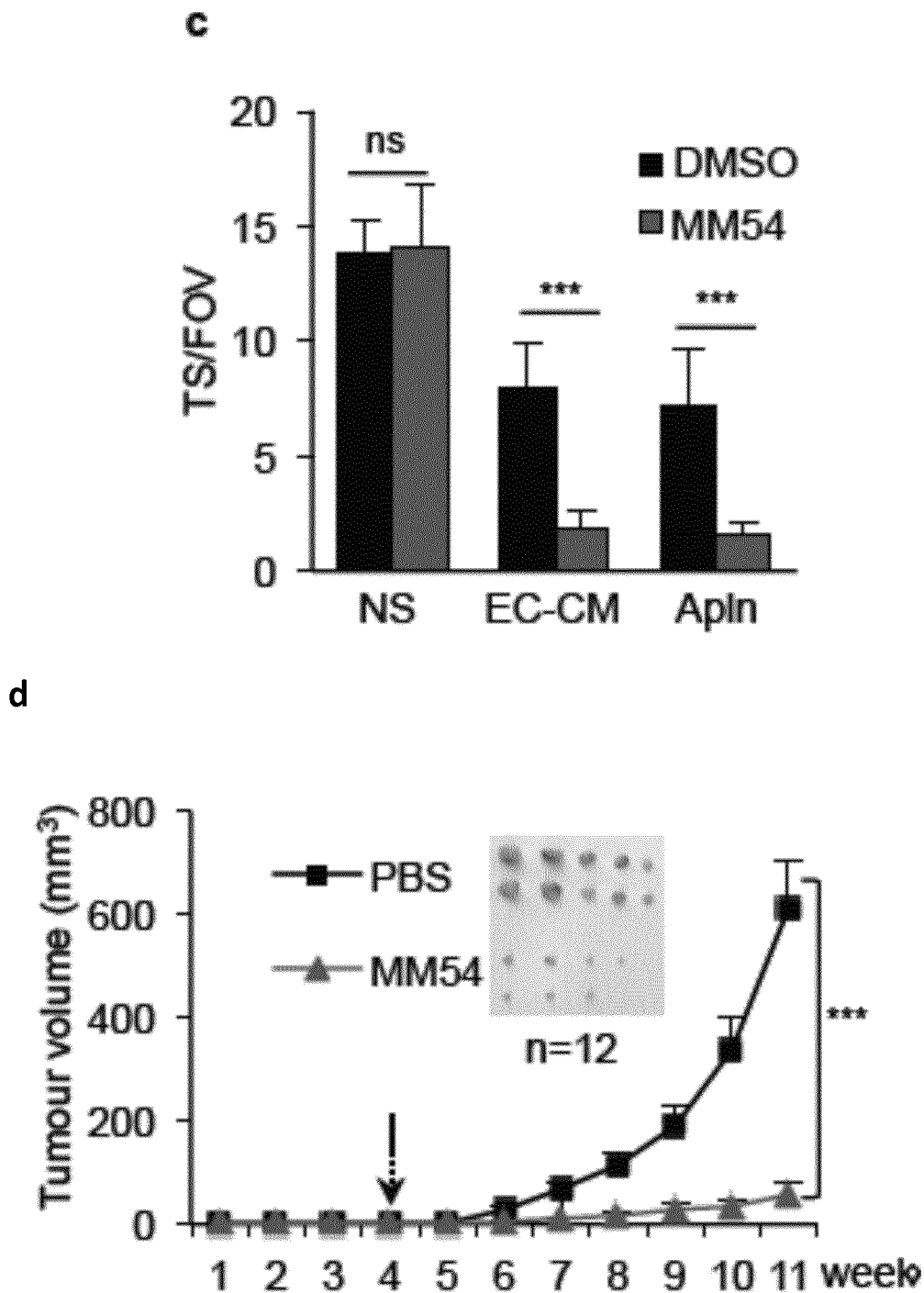
Figure 9:
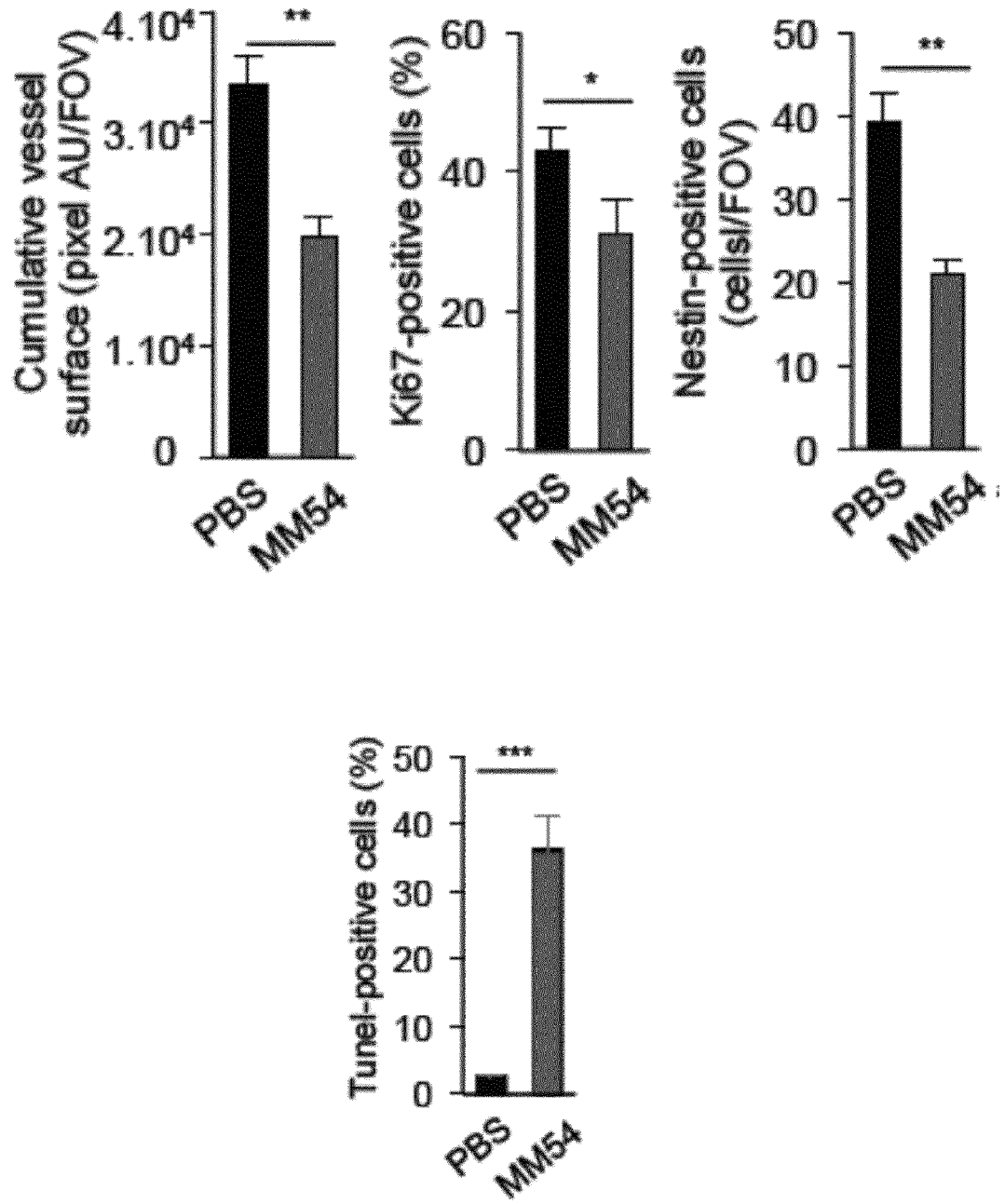

FIG. 9. Pharmacological inhibition of APJ impairs tumour growth. a. GSCs were pre-treated with APJ antagonist (MM54, 2 μmol·l$^{-1}$) 45 min prior EC-CM or Apelin (Apin, 1 μmol·l$^{-1}$, 7 min) and protein lysates were analysed by western-blots with the indicated antibodies. Controls include GSC grown in complete (NS) and mitogen-free media (MF). b. STAT3 reporter activity was measured in mock, APJ, Gp130 and APJ+Gp130-transfected HEK-293T and exposed for 6 h to MF and Apin, together with either DMSO or MM54. c. GSCs were exposed to NS, EC-CM and Apin in the presence of DMSO or MM54. Tumoursphere formation per field of view (TS/FOV) was also quantified. d. Nude mice were xenografted with GSCs and bi-weekly intraperitoneal administration of vehicle (PBS) or APJ antagonist (MM54, 20 μmol·l$^{-1}$) started at week 4 (arrow). Tumour volume was measured weekly for 7 weeks. e. Frozen sections from GSC-xenografted tumours treated either with vehicle or MM54 were stained for blood vessels (PECAM), together with either Ki67 (proliferation marker or Nestin and nuclei. Percentage of dead cells was estimated by TUNEL. Quantification of both staining is shown. Data represent mean+sem on n=3 experiments. Two-way ANOVA: *$P<0.05$; **$P<0.01$.

Figure 10:
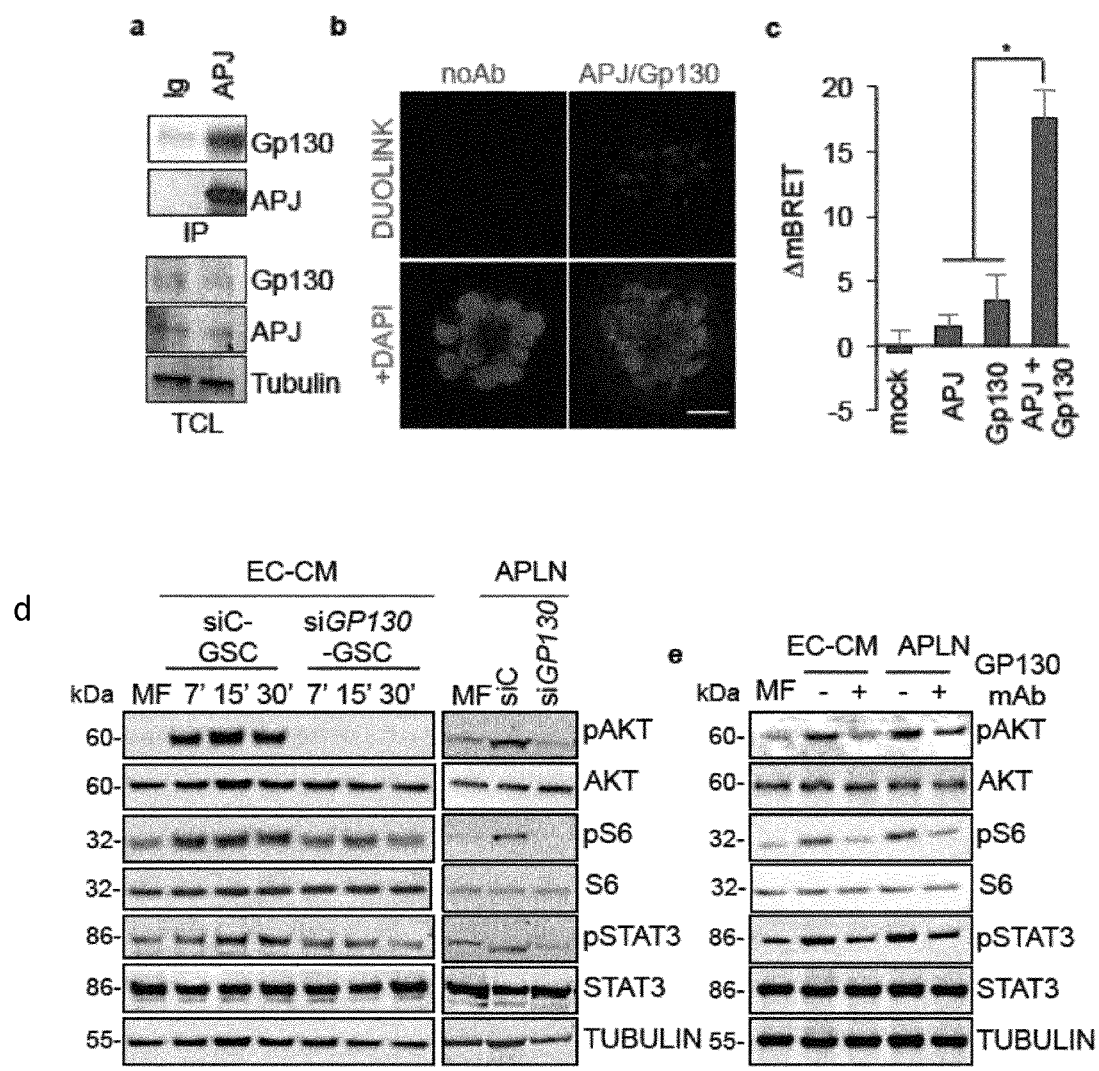
Figure 10:
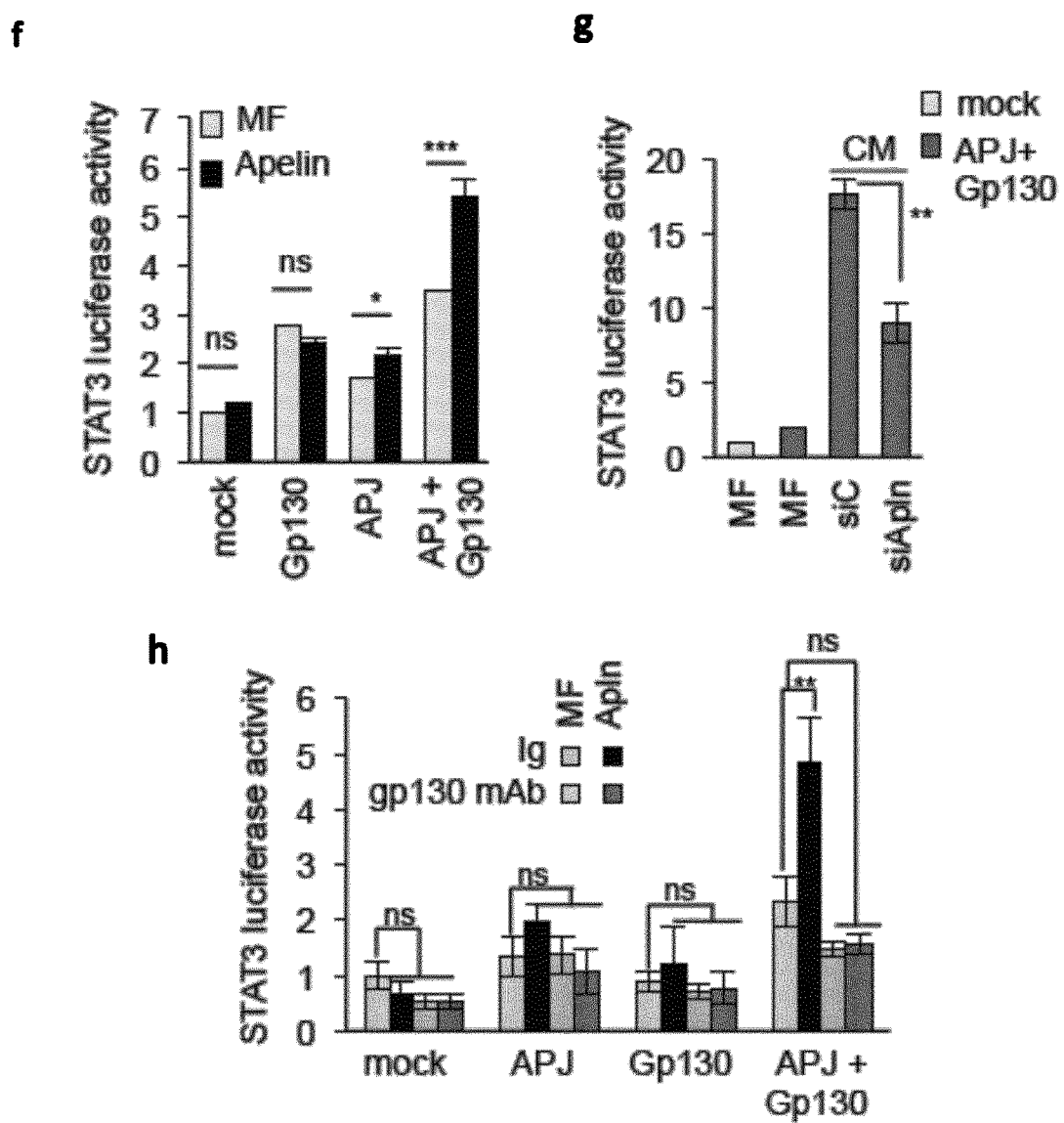
Figure 10:
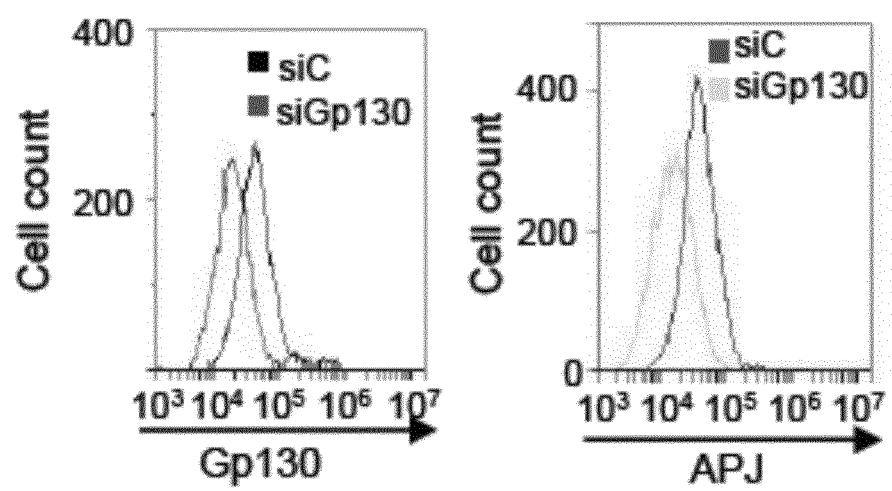
Figure 10:
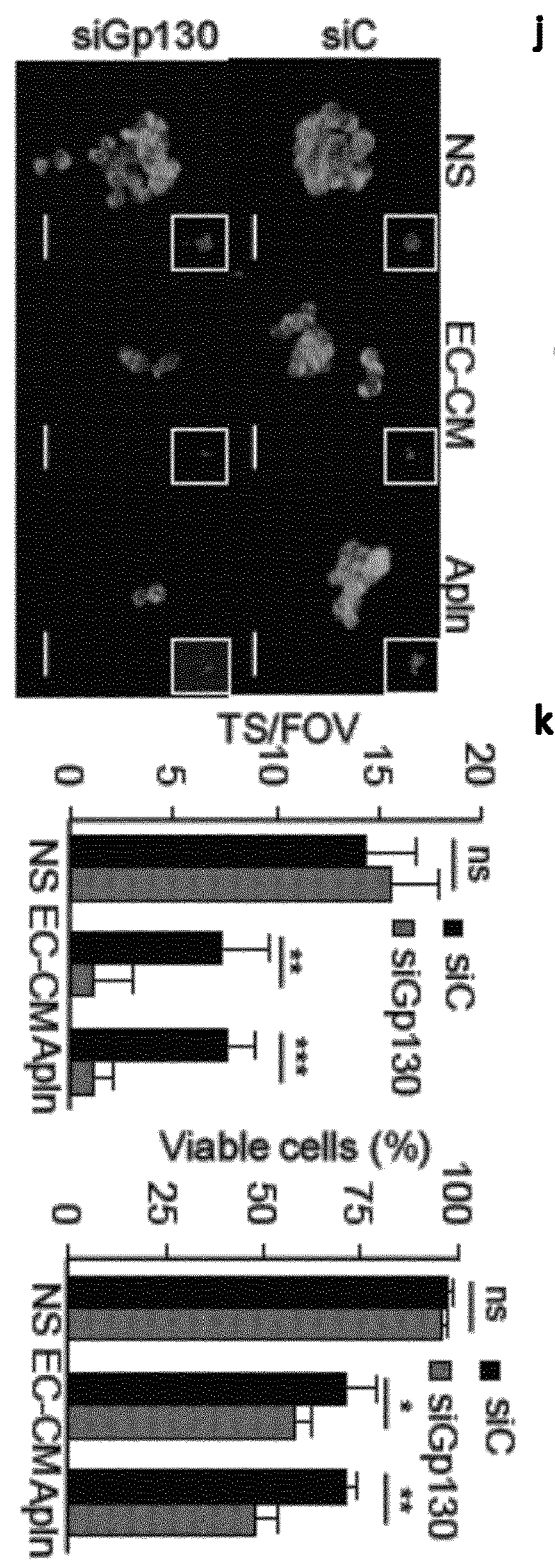
Figure 10:
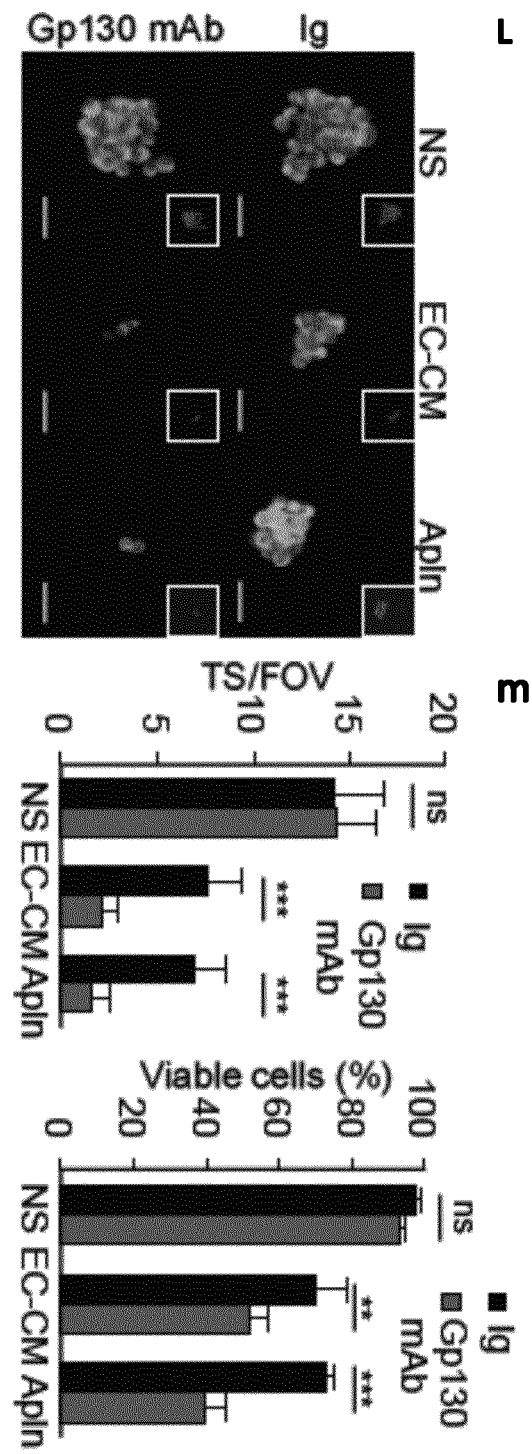

FIG. 10. Gp130 acts a co-receptor for APJ signalling a. Gp130 and APJ expression was evaluated in GSC total cell lysates (TCL) or immunoprecipitated (IP) fractions using anti-APJ antibodies. Immunoglobulin (Ig) was used as a control. b. Gp130 and APJ association was visualised through DuoLink using anti-APJ and anti-Gp130 antibodies (red dots). Staining in the absence of primary antibodies (noAb) is shown. Nuclei were stained with DAPI. Scale bar: 40 um. c. BRET analysis was conducted in HEK-293T cells transfected with mock, APJ, Gp130 and APJ+Gp130 and treated with Apelin (Apin, 1 μmol$^1$, 7 min). Data are presented as Delta mBRET, as described in methods. d. GSCs received either non-silencing RNA (siC) or Gp130 targeting siRNA (siGp130), prior stimulation with mitogen-free medium (MF), endothelial cell-conditioned media (EC-CM, indicated times) or APLN (7 minutes). Protein lysates were analysed by western-blots using the indicated antibodies. e. Alternatively, GSCs were pre-treated with anti-Gp130 blocking antibodies (GP130 mAb) 45 min prior EC-CM or APLN stimulation (7 min). f-h. STAT3 reporter activity was measured through luciferase-based assays in mock, APJ, Gp130 and APJ+Gp130-transfected HEK-293T cells (g, i). Cells were treated for 6 h with MF or Apin (f). mock and APJ+Gp130-transfected HEK-293T cells were exposed to control or Apin-depleted EC-CM (g). Alternatively, cells were pre-treated with anti-Gp130 blocking antibodies or control Ig (h). i. Flow cytometry analysis of total Gp130 and surface APJ expression in GSCs that received siC, siAPJ and siGp130. j-m. siC and siGp130 GSCs were exposed to NS, EC-CM and Apin (j, k). Alternatively, cells were treated with Ig and Gp130 mAb (l, m). Cells were processed for confocal analysis of Nestin (green), Sox2 (red) and nuclei (blue) Scale bar: 40 um. (j, l). Tumoursphere formation per field of view (TS/FOV) and trypan blue exclusion (Viable cells %) were also quantified (k, m). Data represent mean+sem on n=3 experiments. T-test: *$P<0.05$; $P<0.01$; *$P<0.001$.

Figure 11:
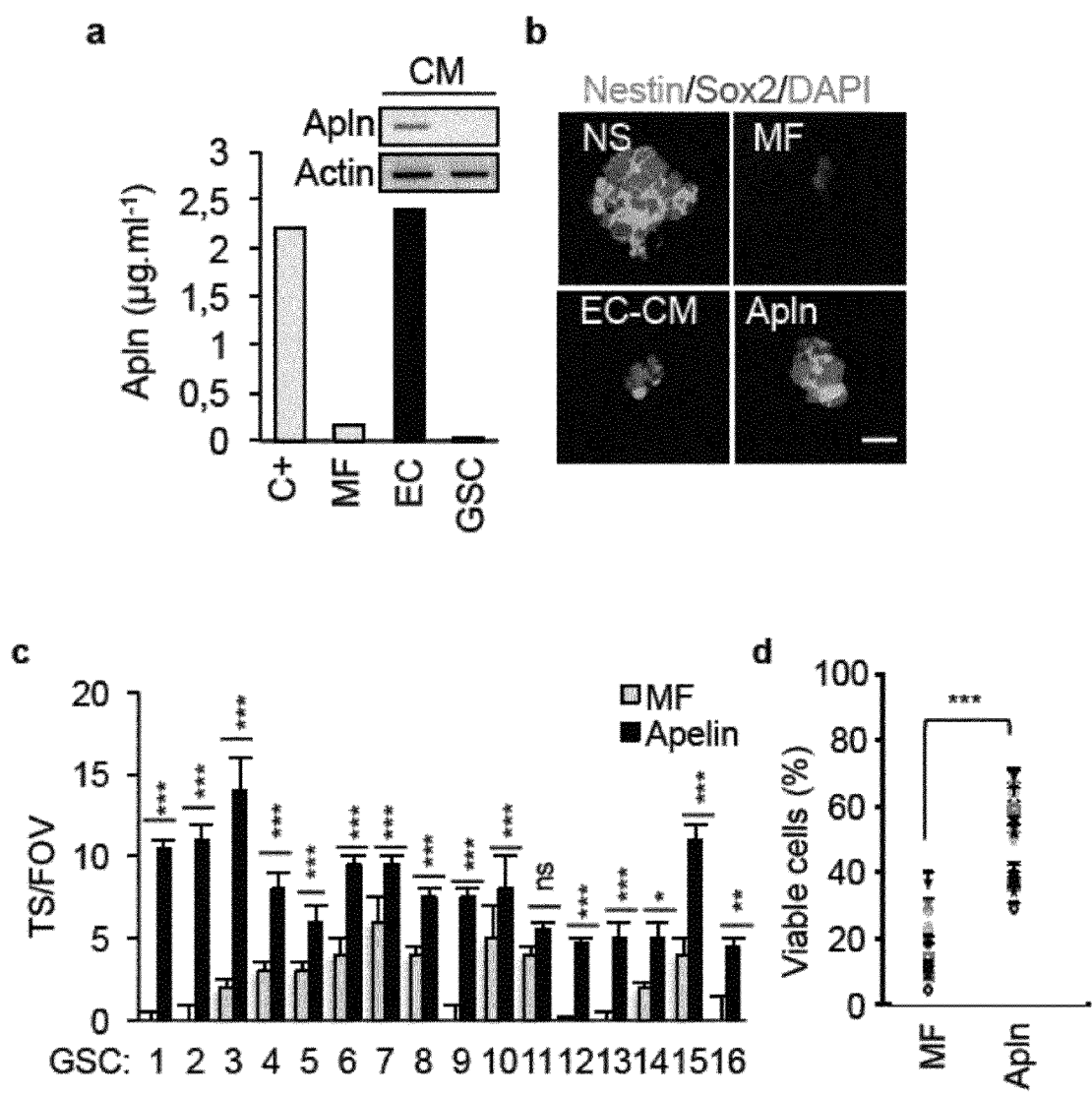
Figure 11:
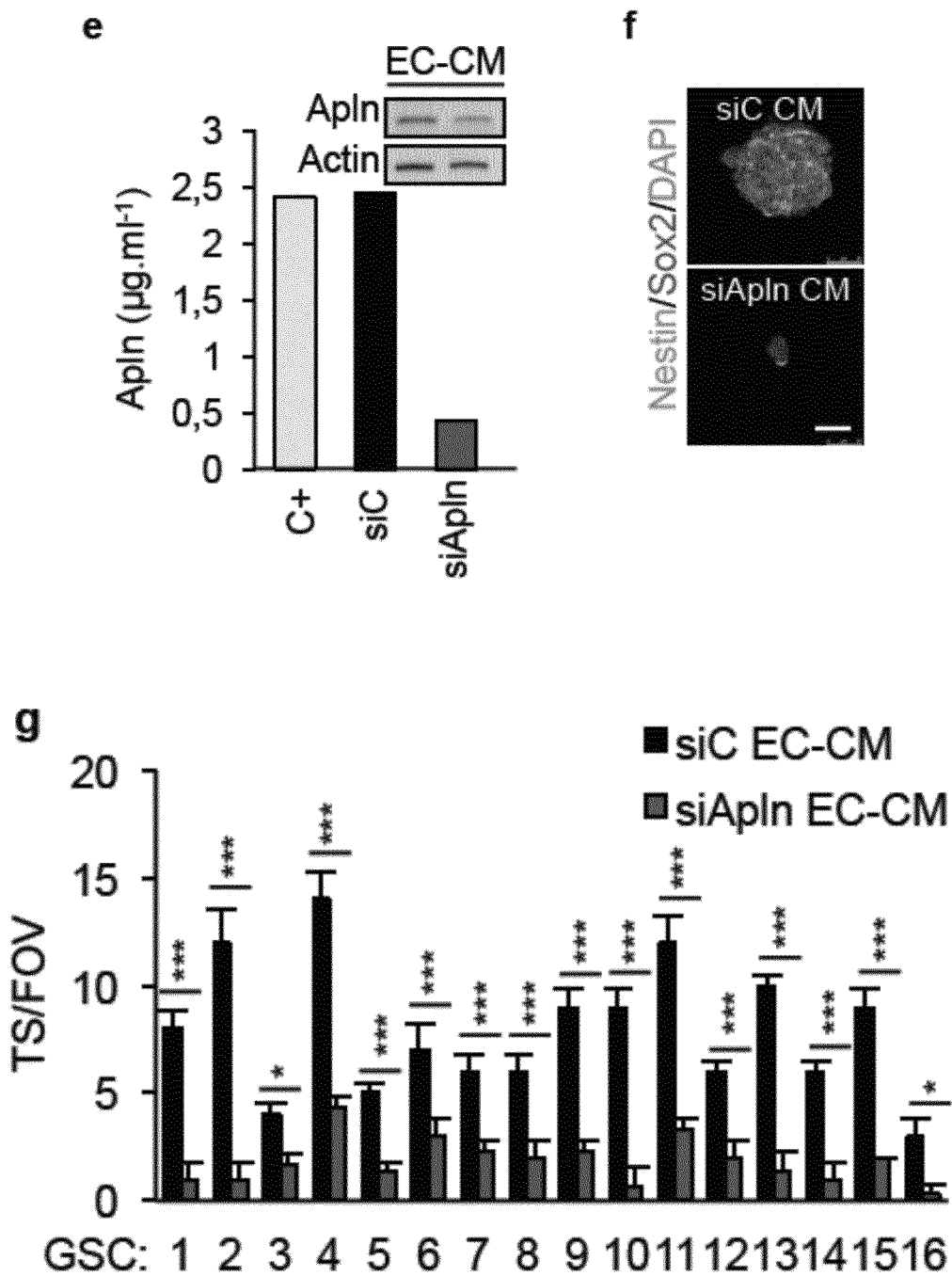
Figure 11:
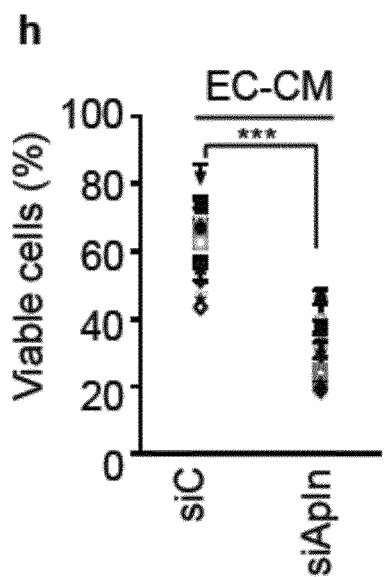
Figure 11:
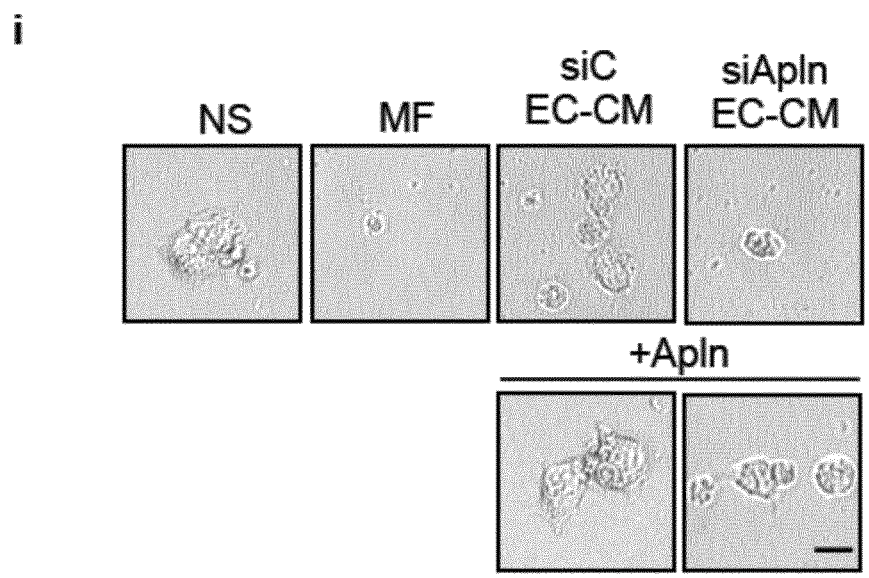
Figure 11:
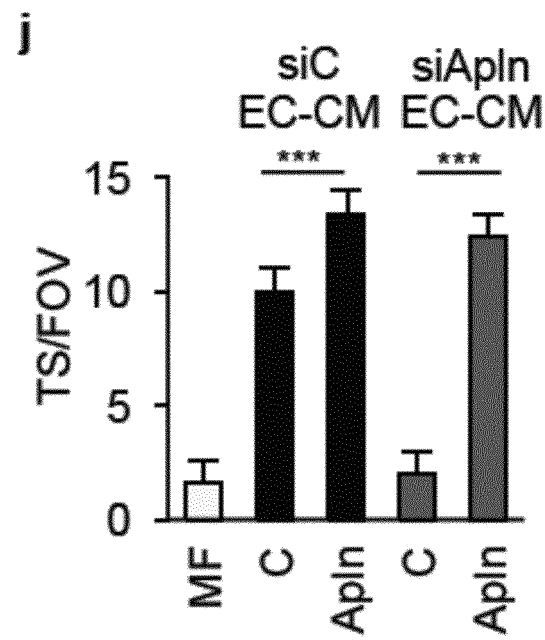
Figure 11:
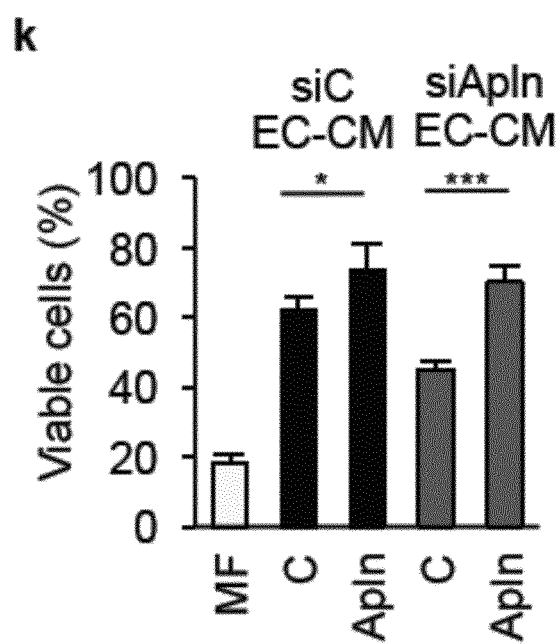

FIG. 11. Endothelial Apelin regulates GSC survival. a. Apelin secretion was measured by EIA in positive templates (C+), mitogen-free media (MF), human brain endothelial cell (EC) and GSC conditioned media (CM). RT-PCR for Apelin and Actin is also shown for EC and GSC. b. Confocal analysis of Nestin (green), Sox2 (red) and nuclei (DAPI, blue) in GSC grown in complete media (NS), in MF, in EC-CM or MF containing only recombinant Apelin (Apin, 1 µmol·l$^{-1}$). Scale bar: 40 um. c-d. GSCs #1-16 were cultured in MF or Apin. Quantification of tumourspheres per field of view (TS/FOV) (c) and trypan blue exclusion quantification (Viable cells %) (d) was performed. e. EC received non-silencing RNA (siC) or Apin targeting siRNA (siApin). Apin extinction was checked by RT-PCR and enzyme immunoassay. f. GSCs were cultured with siC and siApin EC-CM, as prepared in (e). Confocal analysis was performed on Nestin (green), Sox2 (red) and DAPI (blue) co-staining. Scale bar: 40 µm. g-h. siC or siApin EC-CM treated GSCs were processed as in (c, d). i-k. GSCs were cultured with NS, MF, siC EC-CM and siApinEC-CM alone or plus Apin. Phase pictures are shown (i) Scale bar: 25 µm, TS/FOV and viable cells were also analysed (j, k). Data represent mean+sem on n=3 experiments. T-test: *$P<0.05$; $P<0.01$; *$P<0.001$.

Figure 12:
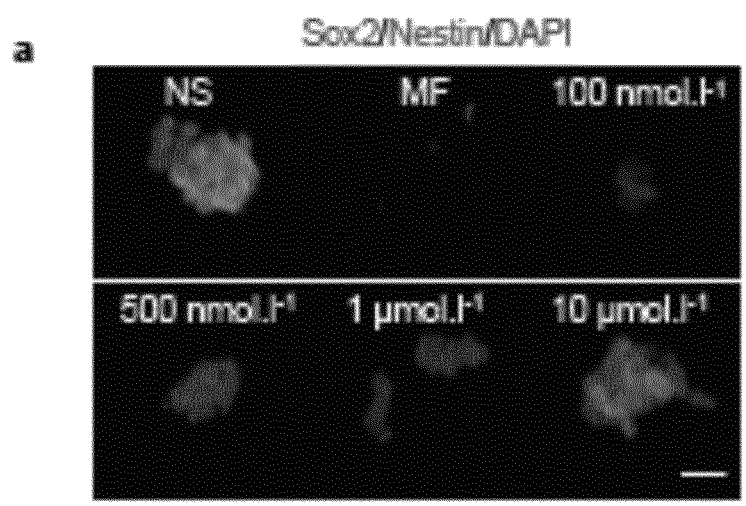

FIG. 12. Apelin dose response. a. Confocal analysis on Sox2 (red), Nestin (green) and Nuclei (blue), together with TS/FOV counts in GSC culture with NS, MF and MF complemented with the indicated Apelin concentrations.

Figure 13:
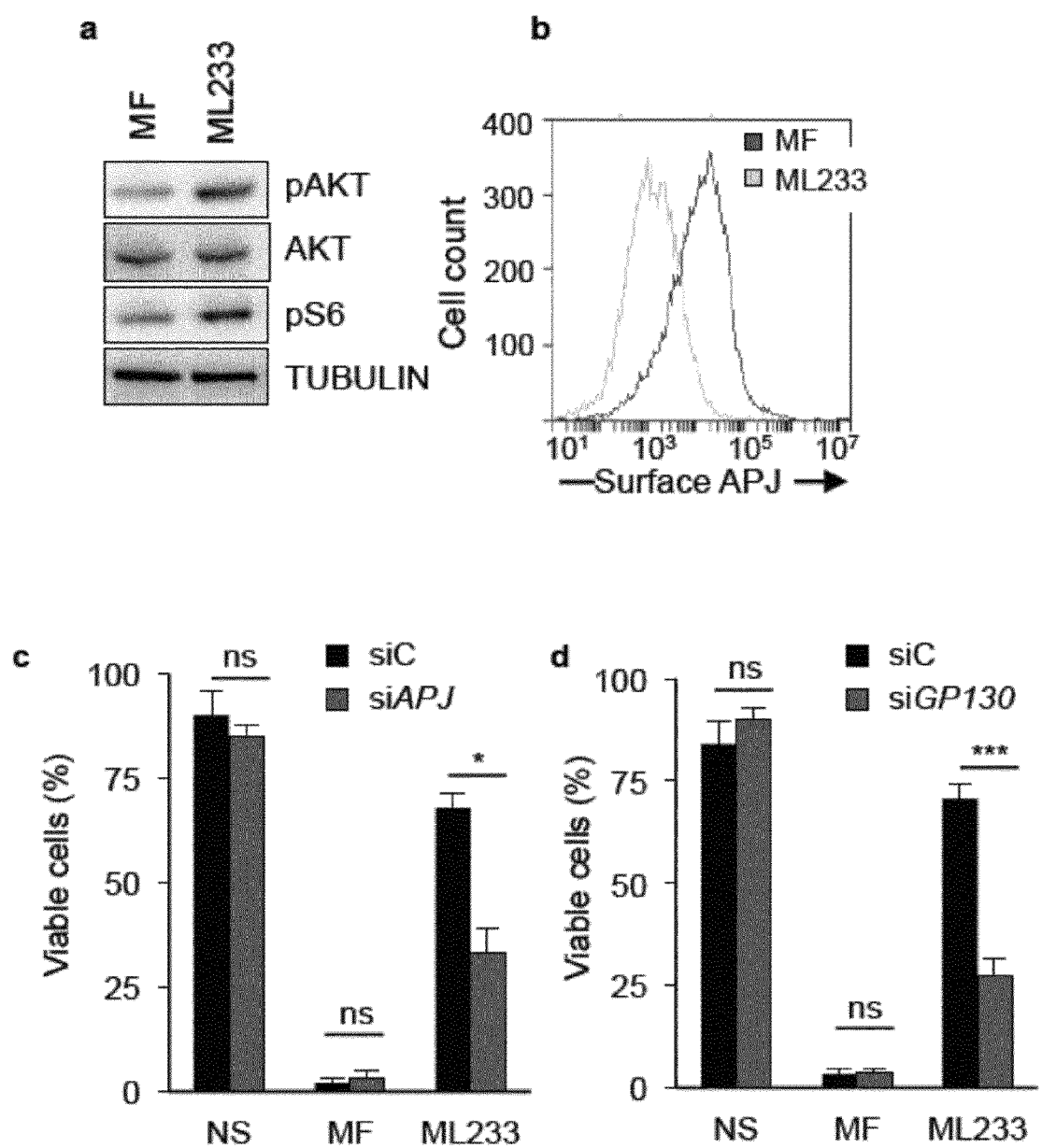

FIG. 13. The ML233 APJ agonist promotes GSC survival through APJ/GP130. a-b. GSC1 were treated with ML233 (1 mmol·l$^{1}$, 7 min) and western-blot for the indicated antibodies (a) and flow cytometry analysis of surface APJ (b) expression were performed. c-d. GSC1 were transfected with non-silencing RNA (siC) or siRNA targeting APJ or GP130 and further exposed to complete medium (NS), mitogen-free (MF) alone or supplemented with ML233 (1 mmol·l$^{1}$) for 4 days. Tumoursphere formation per field of view (TS/FOV) (c) and trypan blue exclusion (Viable cells %) (c) were quantified. Data represent mean+sem on n=3 experiments. T-test: *$P<0.05$; ***$P<0.001$.

Figure 14:
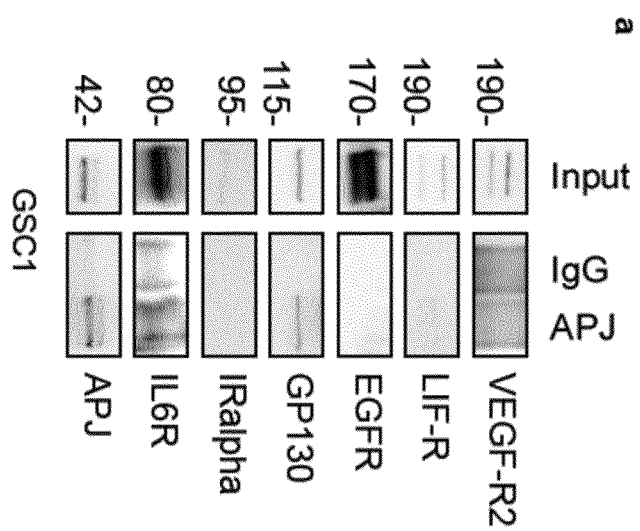
Figure 14:
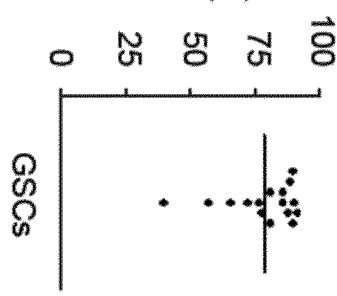
Figure 14:
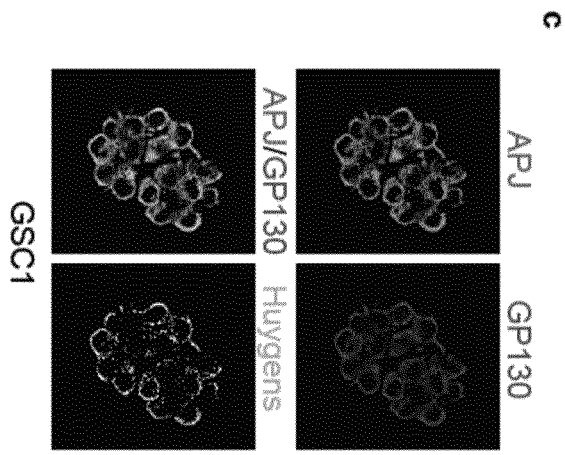
Figure 14:
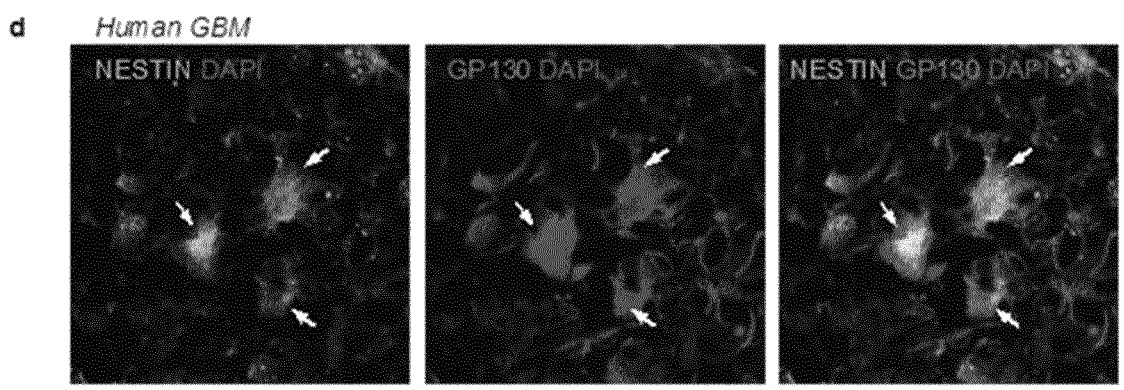

FIG. 14. Gp130 expression and interaction with APJ. a. Control IgG or APJ immunoprecipitated fractions were analysed by western-blot using the indicated antibodies. Input is also shown. b. GP130 expression in GSC#1-16 was evaluated by flow cytometry and % of GP130 expressing cells is indicated. Line represents the median value. c. Confocal analysis of APJ (green) and GP130 (red) in GSC1 grown in NS media. Receptors co-localization analysed with Huygens software is shown. d. Human GBM frozen sections were stained for NESTIN and GP130.

Figure 15:
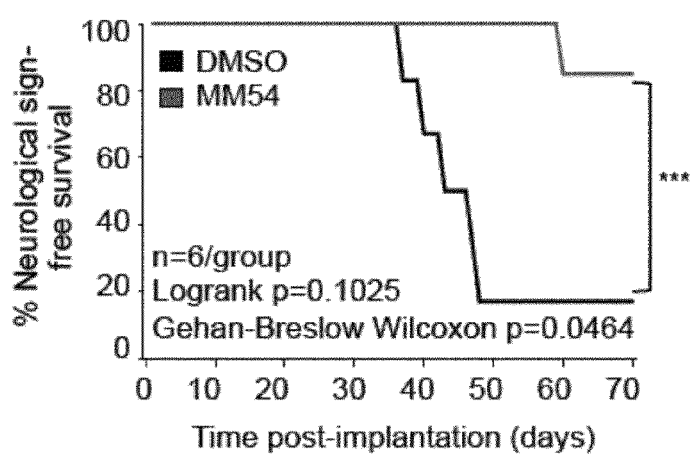
Figure 15:
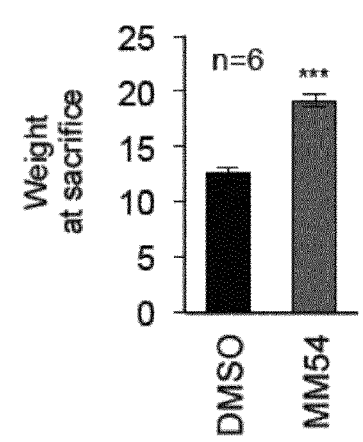
Figure 15:
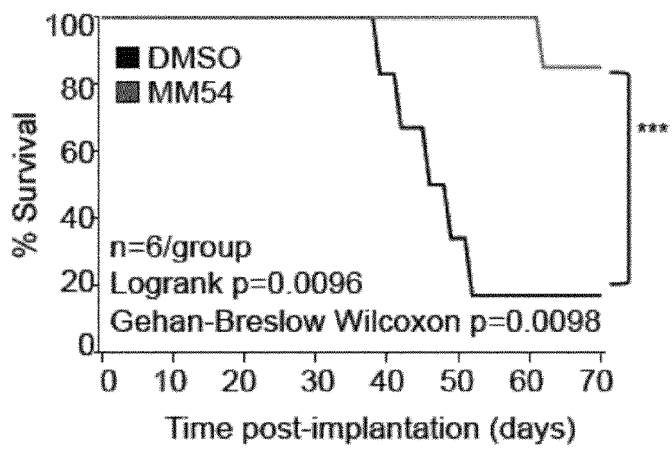

FIG. 15. Anti-tumor effect of APJ inhibition. Nude mice were implanted with GSC #9 orthotopically ($10^5$ cells) and treated tri-weekly with intraperitoneal injection of vehicle (PBS) or APJ antagonist (MM54, 20 µmol·l$^-$, 4 mg/kg) starting at day 16 (arrow). Appearance of neurological symptoms (a) and weight at sacrifice (b) were monitored. Kaplan-Meier survival curve of GSC #9-bearing mice is shown (c). Data represent mean+sem of n=3 experiments. Two-way ANOVA: *$P<0.05$; **$P<0.01$.

Figure 16:
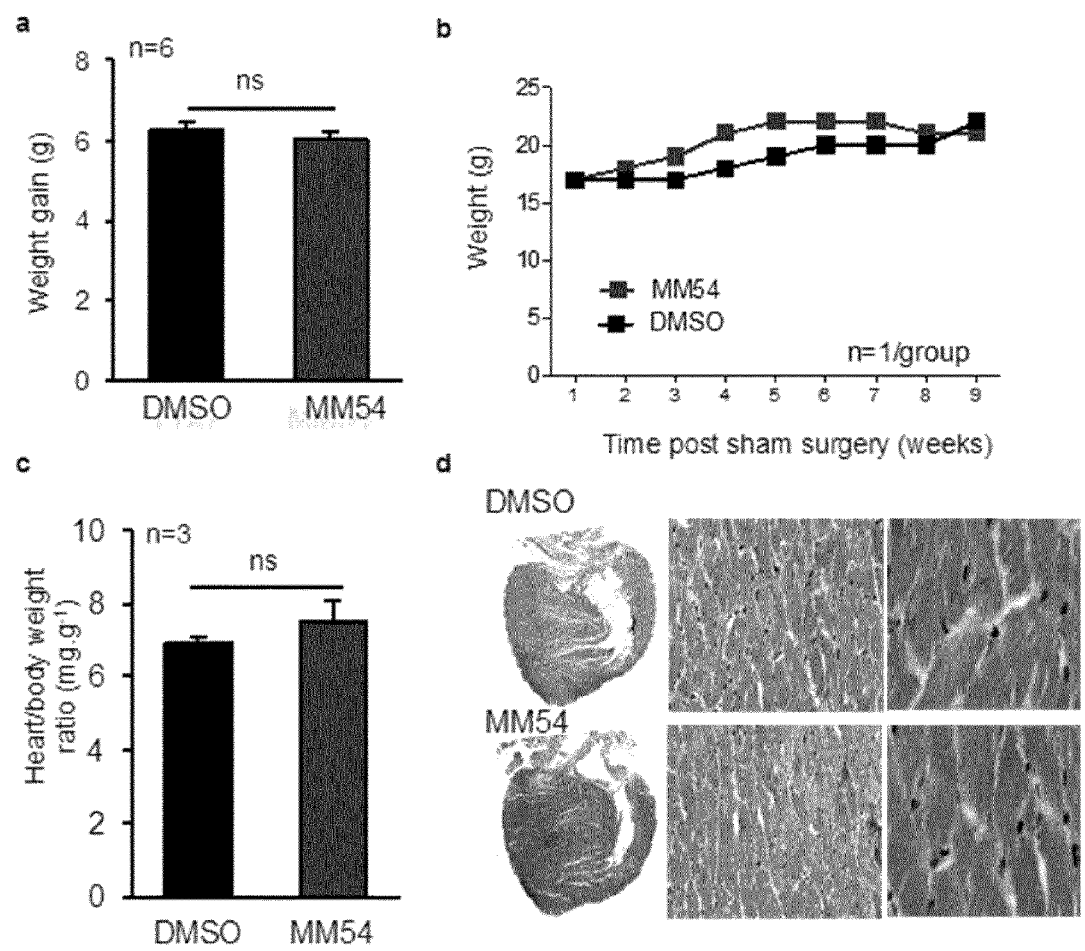

FIG. 16. MM54 treatment does not exert obvious toxic effects a. Gain weight was measured in ectopic tumour bearing mice that received bi-weekly treatment over 7 weeks. b-d. Female nude mice underwent intracranial implantation of PBS (sham surgery) and then received DMSO and MM54 17 days after PBS implantation. Body weight was monitored long the experiment (a). Heart/body weight ratios were calculated at the day of sacrifice (c). General anatomy of hearts from DMSO and MM54-treated mice using the Masson Trichrome staining (d).

Figure 17:
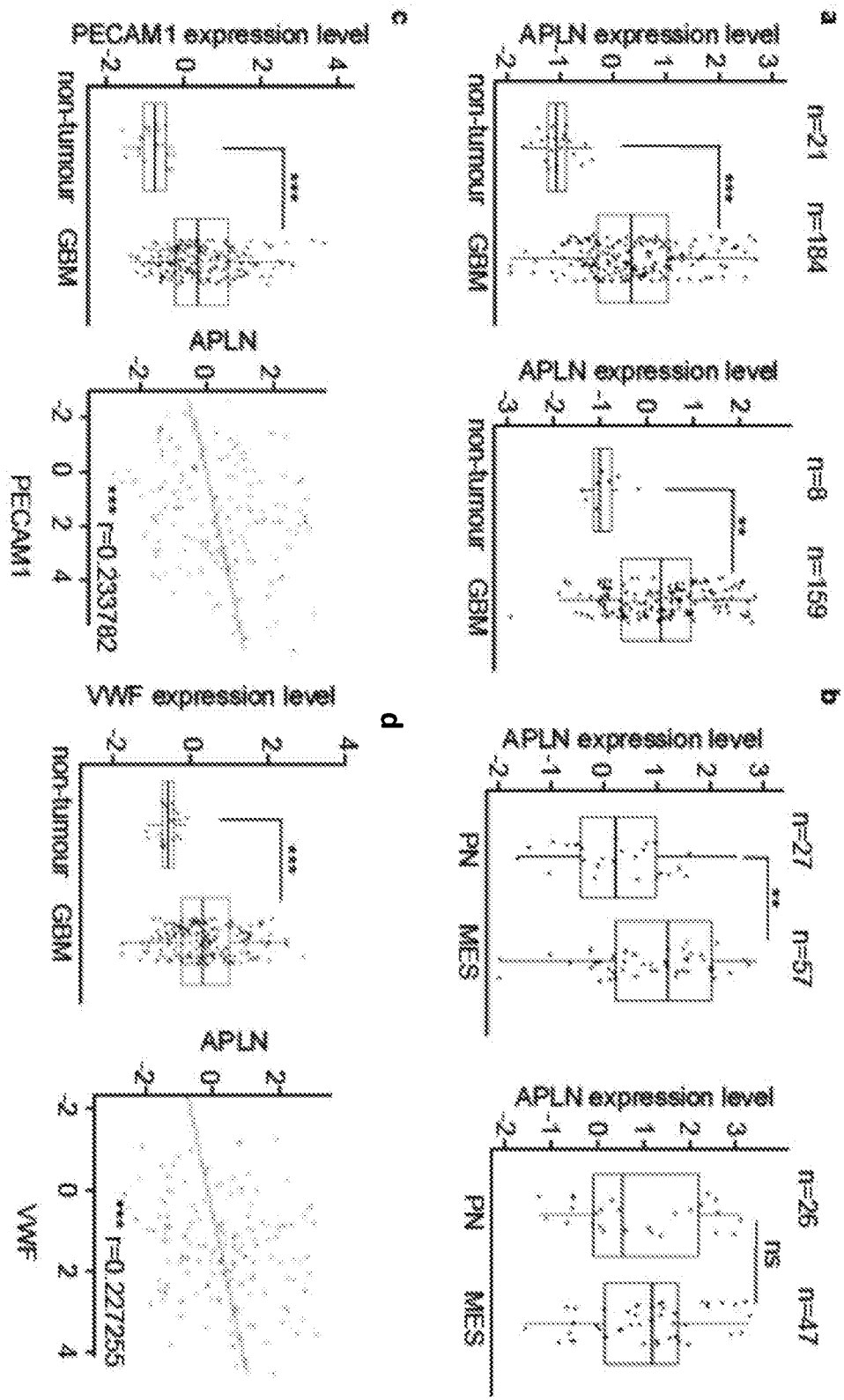
Figure 17:
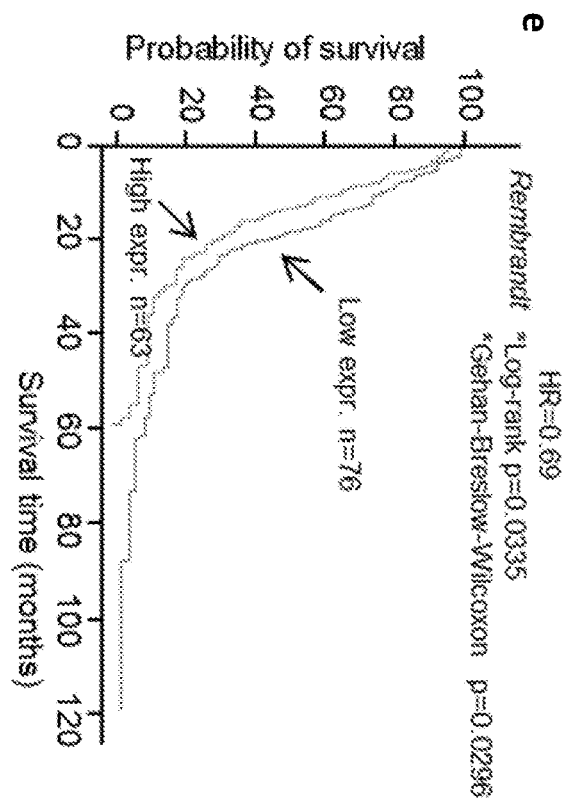
Figure 17:
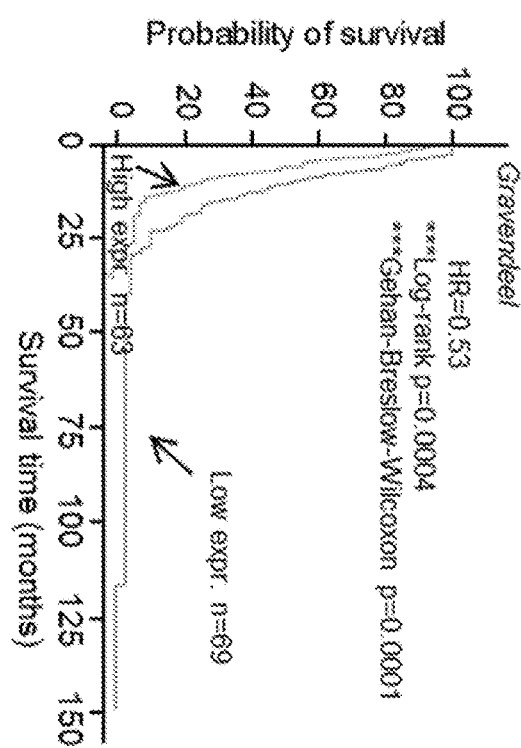

FIG. 17. APLN expression is elevated in human glioblastoma. a. Box-plot showing APT N mRNA levels in control (non-tumour) and glioblastoma (GBM; WHO grade IV) on two independent sample cohorts (National Cancer Institute's Repository for Molecular Brain Neoplasia Data, REMBRANDT and GSE16011 GRAVENDEEL). b. Box-plot showing APLN mRNA levels in GBM from proneural (PN) or mesenchymal (MES) subtypes from the same datasets than in a, c-d. From GRAVENDEEL dataset, PECAM1 and VWF mRNA levels analysis was performed as in a. Correlation of both endothelial factors with APLN is shown r=Pearson's correlation, From a-c, median value is represented by a solid line within the boxes; boxes show the 25$^{th}$ and 75$^{th}$ percentile range of mRNA levels, maximum and minimum values are indicated with vertical bars, points symbolise all patients. Significance was calculated with pairwise comparisons between group levels with corrections for multiple testing (p-values with Bonferroni correction). $P<0.01$; *$P<0.005$. e. Kaplan-Meier survival plot based on patient subgroup from REMBRANDT and GRAVENDEEL data bases comprising only GBM patients, excluding G-CIMP and IDH mutants. In each graph, patient samples have been divided into APLN low expressing tumours (downregulated, as indicated) and APLN high-expressing tumours (up-regulated, as indicated) using the median. Survival differences were compared by log-rank analysis.

Figure 18:
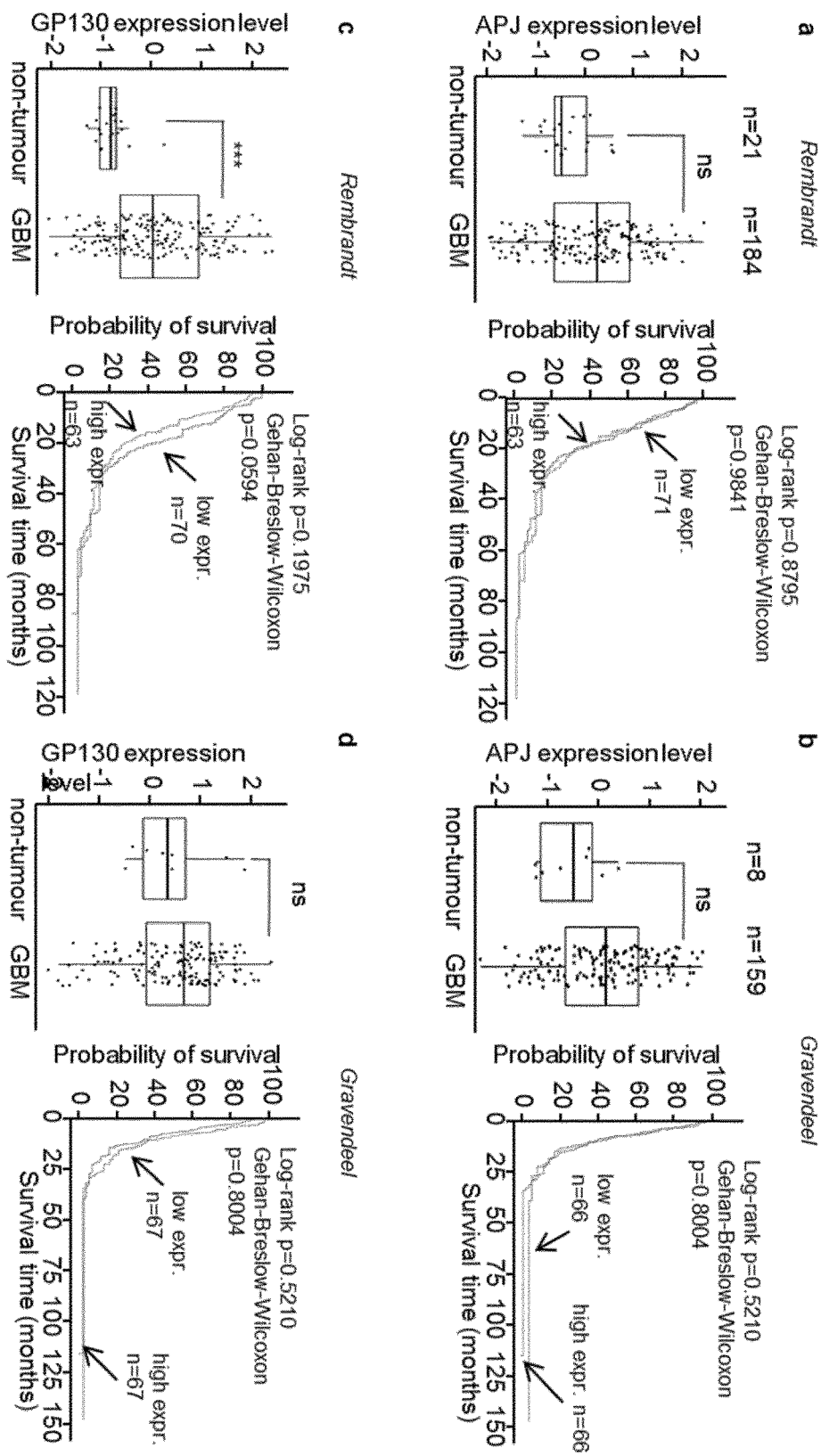

FIG. 18. APJ and GP130 expression do not correlate with patient survival. A-d. Box-plots showing APJ and GP130 mRNA levels and Kaplan-Meier survival plots in GBM patients using REMBRANDT (a,c) and GRAVENDEEL (b,d) databases, and processed as in FIG. 17.

DETAILED DESCRIPTION OF THE INVENTION

Apelin is a 13 amino-acid peptide known for its role in the cardiovascular and neuroendocrine systems. Apelin is reported to operate through a G-protein coupled receptor called "APJ" or "APLNR", which is expressed by endothelial cells of various organs (such as heart, brain, kidney, lungs, etc.) and of a wide variety of tumor types (Rayalam S. et al, 2011). The function of the Apelin/APJ system and the downstream molecular mechanisms involved in cancer stem-like cells are not described yet. The present inventors showed that, surprisingly, the cytokine co-receptor GP130 acts as a co-receptor for Apelin/APJ signaling and that the interaction of Apelin with APJ/GP130 activates a dual signaling pathway involving the Akt/mTOR pathway and the STAT3 transcription factor, thereby promoting GSCs survival and self-renewal. Their results suggest that impairing the Apelin/APJ/GP130 axis inhibits GSCs survival and self-renewal, independently of the Apelin angiogenic activity on ECs.

The molecular axis involving Apelin/APJ/GP130 is therefore a suitable target to interfere with CSCs survival, and, in particular, with GSCs survival. The present invention proposes a methodology for the screening of Apelin/APJ/GP130 pathway inhibitors that target CSCs and are therefore efficient anti-cancer treatments. This invention is of high interest for future medical applications.

Importantly, the compound(s) identified by the screening method of the invention would specifically affect CSCs because only these cells are dependent upon the Apelin/APJ/GP130 pathway and the downstream activation of mTOR and STAT3.

In a first aspect, the present invention relates to a screening method for identifying compounds capable of inhibiting Cancer Stem Cells (CSCs) properties such as self-renewal and survival. This method comprises the steps of:

a) contacting cells expressing the co-receptors APJ and GP130 with the Apelin polypeptide and a candidate compound, b) detecting the activation level of an Apelin-dependent signaling pathway in the cells obtained in step a), c) comparing said activation level with the activation level of said cells contacted only with the Apelin polypeptide.

In a preferred embodiment, the said compound is selected if the activation level of an Apelin-dependent signaling pathway is impaired in the presence of said compound. In other words, the said compound is selected if the activation level of an Apelin-dependent signaling pathway is decreased in cells contacted with said compound and Apelin, as compared with the activation level of the same Apelin-dependent signaling pathway measured in the presence of Apelin alone.

An alternative screening method useful in the context of the invention involves the measurement of APJ/GP130 interaction by Proximity Ligation Assay (PLA). In this particular embodiment, said method comprises the following steps:

a) contacting cells with PLA-labelled APJ and GP130 with the Apelin polypeptide and a candidate compound, b) detecting the PLA signal obtained in step a), c) comparing the PLA signal obtained in the presence of the candidate compound with the PLA signal obtained only with the Apelin polypeptide.

In a preferred embodiment, the said compound is selected if the PLA signal is impaired in the presence of said compound. In other words, the said compound is selected if the PLA signal is decreased when said compound is added, as compared with the PLA signal measured in the presence of Apelin alone.

The PLA technology is known to enable the detection of interacting proteins for molecules in close vicinity (<40 nm). It is broadly used by the skilled person. The DUOLINK kit (Sigma) may be used in this purpose. The PLA signal is preferably a fluorescent signal (see FIG. 10B).

The Apelin Polypeptide and Its Receptor, APJ.

The Apelin gene (also known as APLN, APJ endogenous ligand, APEL and XNPEP2) encodes a pre-proprotein of 77 amino acids containing a signal peptide in the N-terminal region. After translocation into the endoplasmic reticulum and cleavage of the signal peptide, the proprotein of 55 amino acids generates several active fragments: a 36 amino acid peptide corresponding to the sequence 42-77 (Apelin 36), a 17 amino acid peptide corresponding to the sequence 61-77 (Apelin 17) and a 13 amino acid peptide corresponding to the sequence 65-77 (Apelin 13). In human, the proprotein Apelin has for example the SEQ ID NO:1 (NP_059109).

As used herein, the term "Apelin polypeptide" or "Apelin" is intended to refer to a polypeptide that comprises the C-terminal 13 amino acids of the Apelin proprotein (i. e., the polypeptide of SEQ ID NO: 2, corresponding to amino acids 65-77 of NP_059109) or a polypeptide that corresponds to the sequence 42-77 of the Apelin proprotein (Apelin 36) (i. e., the polypeptide of SEQ ID NO: 3). Preferably, it consists of SEQ ID NO:2 (corresponding to amino acids 65-77 of NP_059109).

The Apelin polypeptide used in the method of the present invention can be obtained by any conventional means. For example, it can be obtained by suppliers of biochemical molecules (Santa Cruz, Cayman, Sigma Aldrich, etc.). It can also be synthesized chemically by standard peptide synthesis techniques. For the purposes of this invention, when chemically synthesized, the apelin-13 peptide may comprise a pyroglutamate rather than a glutamic acid residue in the N-terminal position. As an alternative to standard peptide synthesis, the Apelin polypeptide can be produced using standard recombinant DNA techniques. For example, a nucleic acid molecule encoding the polypeptide can be cloned into an expression vector, the expression vector can be introduced into a host cell, and the Apelin polypeptide can be expressed in the host cell. The Apelin polypeptide can then be isolated from the cells by an appropriate purification scheme using standard polypeptide purification techniques.

The Apelin polypeptide has been involved in several physiological functions depending on the cellular localization of its receptor, APJ. These include cardiovascular regulation, fluid homeostasis, modulation of the adipoinsular axis, and HIV coreceptor function in vitro (Pitkin et al, 2010). Apelin has been implicated in cancer as a pro-angiogenic factor, although its exact role is still matter of debate (Rayalam S. et al, 2011 and Kidoya H., 2012). Apelin/APJ signaling is known to activate the mTor pathway (Masri B. et al, 2004). APJ (also known as Apelin receptor, AR, Angiotensin receptor-like 1, G-protein coupled receptor APJ, APLNR, AGTRL, APJ, APJR, and HG11) is the cognate receptor for Apelin (Lee D K. et al,). It belongs to the G protein-coupled receptor family and is located at cell surface. APJ is related to the angiotensin II receptor and has been described as a co-receptor involved in the mediation of HIV-1 neuropathogenesis, cardiovascular and neuroendocrine functions (Pitkin et al, *Pharmacological Review*, 2010). In human, APJ has for example the SEQ ID NO:4 (NP 005152) and is encoded by SEQ ID NO:5 (NM 005161).

The GP130 Co-Receptor

The GP130 protein (also known as Glycoprotein 130, IL6ST, IL6-beta, Interleukin-6 receptor subunit beta, IL-6 receptor subunit beta, IL-6R subunit beta, IL-6R-beta, IL-6RB, IL6RB, CDw130, Interleukin-6 signal transducer, Membrane glycoprotein 130, Oncostatin-M receptor subunit alpha or CD130) is a trans-membrane protein cytokine receptor. More specifically, GP130 is known to facilitate cytokine-driven signaling, such as the ones induced by IL-6, EPO and LIF. It has no intrinsic tyrosine kinase activity. Instead, it is phosphorylated on tyrosine residues after complexing with other proteins. This phosphorylation leads to association with JAK/Tyk tyrosine kinases and STAT protein transcription factors, such as STAT-3. Structurally, GP130 is composed of five fibronectin type-III domains and one immunoglobulin-like C2-type domain in its extracellular portion. In human, it has the sequence SEQ ID NO:6 (Gene Bank number: P40189.2) and is encoded by SEQ ID NO:7 (NM_000565.3).

Gp130 is known to activate the STAT3 pathway. This pathway is implicated in cell proliferation, migration and survival, and is further reported activated in cancer stem-like cells (Chautard E. et al, 2010), and recently in GSCs (Kim E. et al, 2013). However, the present inventors describe for the first time the functional interplay between APJ/GP130 and Apelin.

More precisely, the inventors herein show that GP130 maintains APJ at the plasma membrane to marshal Apelin/APJ signaling in GSCs (see FIG. 10).

Cells Expressing the APJ and GP130 Receptors

The screening methods of the invention may use any cells expressing the co-receptors APJ and GP130 at their membrane. Expression of these co-receptors can be endogenous or exogenous. In a preferred embodiment, the screening methods of the invention uses cells expressing high levels of the said receptors at their membrane. Although it is not excluded to use primary cells, cultured cells from conventional cell lines are however preferred, as their behavior is fully characterized, and they can be easily transfected in order to express exogenous polypeptides.

In a more preferred embodiment, the methods of the invention uses recombinant cells issued from conventional cell lines that have been transfected with exogenous nucleotide vectors expressing the co-receptors APJ and GP130. In an even more preferred embodiment, these cells do not endogenously express the co-receptors APJ and GP130, so as to ensure that the Apelin-dependent activation in GSCs requires the presence of the two co-receptors APJ and GP130 and not of only one of them.

These conventional cell lines are for example HEK293T cells, HeLa cells, COS-7 cells, CHO cells, U87-MG, and LN229 cells.

A particular cell line of interest is for example the APJ-expressing cell line of Millipore which is made in the Chem-5 host and supports high levels of recombinant APJ expression on the cell surface. This cell line advantageously contains optimized levels of a recombinant promiscuous G protein to couple the receptor to the calcium signaling pathway.

Methods to generate recombinant cells expressing APJ and GP130 are well-known in the art. For examples, conventional molecular biology, microbiology and recombinant DNA techniques can be used [see Sambrook, Fitsch & Maniatis, Molecular Cloning: A Laboratory Manual, Second Edition (1989) Cold Spring Harbor Laboratory Press, Cold Spring Harbor, N.Y.), Current Protocols in Molecular Biology, John Wiley & Sons, Inc. (1994)].

In particular, nucleotide vectors expressing the APJ and GP130 co-receptors may be transfected in the cells by means of any "transfection" system (for example by lipofection, by infection, by calcium phosphate-DNA precipitation or by electroporation), and the translation of the polynucleotide encoding said co-receptors is induced.

The term "vector", as used herein, is intended to refer to a nucleic acid molecule capable of carrying another nucleic acid. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e. g., bacterial vectors having a bacterial origin of replication and episomal mammalian vectors). Other vectors (e. g., non-episomal mammalian vectors) can be integrated into the genome of a host cell upon introduction into the host cell, and thereby are replicated along with the host genome.

Certain vectors are capable of directing the expression of genes to which they are operatively linked. Such vectors are referred to herein as "recombinant expression vectors" (or simply, "expression vectors"). In general, expression vectors of utility in recombinant DNA techniques are in the form of plasmids. In the present specification, "plasmid" and "vector" may be used interchangeably as the plasmid is the most commonly used form of vector. However, the invention is intended to include such forms of expression vectors, such as bacterial plasmids, YACs, cosmids, retrovirus, EBV-derived episomes, and all the other vectors that the skilled man will know to be convenient for ensuring the expression of the co-receptors GP130 and APJ.

Transformation of these vectors into the cells can be carried out by any known method for introducing polynucleotides into a host cell. Such methods are well known of the man skilled in the art and include e.g., dextran-mediated transformation, calcium phosphate precipitation, polybrene-mediated transfection, protoplast fusion, electroporation, encapsulation of the polynucleotide into liposomes, biolistic injection and direct microinjection of DNA into nuclei.

In a particular embodiment, the cells used in the method of the invention are HEK-293T stably expressing the APJ and the GP130 co-receptors of SEQ ID NO:4 and 6 respectively. HEK-293T can be transfected for example with plasmids encoding these polypeptides using the Turbofect system, using the manufacturer recommendations (for detailed explanations, see examples below).

The method of the invention comprises a first step of "contacting cells expressing the co-receptors APJ and GP130 with the Apelin polypeptide and a candidate compound". The Apelin polypeptide may be added after, simultaneously, or before the candidate compound.

In a preferred embodiment, the recombinant cells expressing the co-receptors APJ and GP130 are contacted with the Apelin polypeptide after being contacted with the candidate compound. The tested compound, if selected, will be for example able to impair the binding of Apelin on its binding site on the APJ/GP130 co-receptors or to down regulate the expression of APJ or GP130.

In another preferred embodiment, the recombinant cells expressing the co-receptors APJ and GP130 are contacted with the Apelin polypeptide after being contacted with the candidate compound. The tested compound, if selected, will be for example able to mask the binding site of Apelin on APJ/GP130 without activating these co-receptors (therefore acting as an antagonist of the Apelin).

If Apelin and the candidate compound are put in contact simultaneously with the cells expressing APJ/GP130, both phenomenons are likely to occur.

Cancer Stem Cells (CSCs) and CSCs Properties

As used herein, the term "Cancer stem cells" or "CSCs" refers to cancer cells that possess the properties of normal stem cells, specifically the ability to differentiate into multiple cell types (potency), and the ability to go through numerous cycles of cell division while maintaining in an undifferentiated state (self-renewal).

These properties may be tested by various methods such as clonogenic or sphere assays, in which single cells are assessed for their ability to differentiate and self-renew (Thomson S P, *Cancer Research*, 1982). Also, clonal cell transplantation systems can be used (Nakauchi et al, *Ann NY Acad Sci.* 2001), as well as their ability to initiate tumor formation in vivo.

CSCs can be identified by various means. For example, it is possible to identify them by using distinctive set of cell surface markers including CD133 (also known as PROM1), CD44, CD24, EpCAM (epithelial cell adhesion molecule, also known as epithelial specific antigen, ESA), THY1 and ATP-binding cassette B5 (ABCB5) (Al-Hajj et al, PNAS 2003). Alternatively, it is possible to identify CSCs by letting them grow in the absence of serum and without attachment to culture plates (differentiated cells fail to survive under the same conditions). Also, CSCs can be identified by their characteristic slow-cycling and quiescent properties (Horan P K, *Methods Cell Biol.* 1990).

In a preferred embodiment, the Cancer Stem Cells targeted by the compound of the invention are those present in breast cancer, head and neck cancer, lung cancer, ovarian cancer, pancreatic cancer, colorectal carcinoma, cervical cancer, sarcomas, brain tumors, renal cancer, melanoma and skin cancer, prostate cancer, gastric cancer, multiple myeloma, leukemia and lymphoma.

In a particularly preferred embodiment, Cancer Stem Cells targeted by the compound of the invention are Gliobastoma Stem Cells (GSCs). Gliobastoma Stem Cells are CSCs present in brain tumors. Biomarkers of GSCs are for example CD133, podoplanin, CD15, A2B5, filament markers (nestin), RNA-binding proteins (Musashi-1) and transcription factors (BMI1, SOX2, Id1, and Oct-4) (for a review, see Dahlrot R H. et al, *Int. J. Gin. Exp. Pathol.* 2013).

Compound to be Tested

The compound to be tested in the method of the invention is of any kind. In a preferred embodiment, it is selected from the group consisting of: an anti-sense nucleic acid, a receptor decoy, an aptamer, an antibody and a small molecule antagonist.

As used herein, the term "anti-sense nucleic acid" refers to a polynucleotide that is specific for a sequence encoding the Apelin, GP130 or APJ polypeptides, or a portion of one of those sequences. The nucleic acid sequences encoding these proteins are described herein (SEQ ID NO:5 and 7). These sequences are furthermore available on public databases, such as the GenBank database operated by the NCBI.

A person skilled in the art would be able to design, make and use suitable anti-sense molecules, based on these sequences, without undue experimentation. The anti-sense nucleic acid may be, e.g., an oligonucleotide, or a nucleic acid comprising an anti-sense sequence that is operably linked to an expression control sequence. The use of anti-sense nucleic acids to down-regulate the expression of a particular protein in a cell is well known in the art. An anti-sense nucleic acid molecule may comprise a nucleotide sequence that is complementary to the coding strand of another nucleic acid molecule (e.g., an mRNA sequence), or to a portion thereof, and accordingly is capable of hydrogen bonding to the coding strand of the other nucleic acid molecule. Alternatively, anti-sense sequences can be complementary to a sequence found in the 5' or 3' untranslated region of the mRNA or a region bridging the coding region and an untranslated region (e.g., at the junction of the 5' untranslated region and the coding region). The anti-sense nucleic acid can be complementary in sequence to a regulatory region of the gene encoding the mRNA, for instance a transcription initiation sequence or regulatory element, or a splice site. In one embodiment, an anti-sense nucleic acid is designed so as to be complementary to a region preceding or spanning the initiation codon on the coding strand or in the 3' untranslated region of an mRNA.

The anti-sense nucleic acid of the invention is preferably an RNA, such as a short interfering RNA (siRNA), a double-stranded RNA (dsRNA), a micro-RNA (miRNA), a short-hairpin RNA (shRNA).

As used herein, the term "receptor decoy" refers to a molecule that will bind to an Apelin polypeptide and prevent the apelin polypeptide from participating in its native signaling pathway (s). A receptor decoy is intended to encompass a soluble receptor for apelin (or fragment thereof) which is capable of binding apelin and inhibiting apelin from signaling through its native signaling pathway (s).

As used herein, the term "aptamer" relates to oligonucleic acid or peptide molecules that bind specifically to a specific target molecule. It preferably refers to an oligonucleic acid. Aptamers can be selected in vitro by the SELEX process from very large populations of random sequence oligomers (Ellington et Szostak, *Nature* 1990). This well-established methodology selects aptamers based on their affinity for a specific target molecule.

In a more preferred embodiment, this tested compound is an antibody or a functional antibody fragment impairing the interaction of Apelin with GP130 and APJ. Said antibody or functional fragment thereof can preferably bind Apelin, GP130 or APJ.

The term "antibody" as used herein designates a polypeptide that exhibit binding specificity to a specific antigen. More particularly, an antibody (or "immunoglobulin") consists of a glycoprotein comprising at least two heavy (H) chains and two light (L) chains inter-connected by disulfide bonds. Each heavy chain comprises a heavy chain variable region (or domain) (abbreviated herein as $V_H$) and a heavy chain constant region (hereafter $C_H$). Heavy chains are classified as gamma, mu, alpha, delta, or epsilon, and define the antibody's isotype as IgG, IgM, IgA, IgD, and IgE, respectively. The $C_H$ region of the immunoglobulin IgG, IgD, and IgA (γ, δ and α chains respectively) comprises three domains (CH1, CH2, and CH3) and a hinge region for added flexibility, while the $C_H$ region of the immunoglobulin IgM and IgE contains 4 domains (CH1, CH2, CH3, and CH4). An "epitope" is the site on the antigen to which an antibody binds. It can be formed by contiguous residues or by non-contiguous residues brought into close proximity by the folding of an antigenic protein.

As used herein, the term "antibody fragments" intends to designate Fab, Fab', F(ab')$_2$, scFv, dsFv, ds-scFv, dimers, minibodies, diabodies, and multimers thereof and bispecific antibody fragments. Antibodies can be fragmented using conventional techniques. For example, F(ab')$_2$ fragments can be generated by treating the antibody with pepsin. The resulting F(ab')$_2$ fragment can be treated to reduce disulfide bridges to produce Fab' fragments. Papain digestion can lead to the formation of Fab fragments. Fab, Fab' and F(ab')$_2$, scFv, dsFv, ds-scFv, dimers, minibodies, diabodies, bispecific antibody fragments and other fragments can also be synthesized by recombinant techniques.

A "functional fragment" of an antibody means in particular an antibody fragment as defined above, with the same binding activity as the parental antibody.

In the context of the present invention, an antibody is said to "recognize" or "bind" a peptide having a define sequence if said antibody has an affinity constant $K_a$ (which is the inverted dissociation constant, i.e. $1/K_d$) higher than $10^6$ $M^{-1}$, preferably higher than $10^7$ $M^{-1}$, more preferably higher than $10^8$ $M^{-1}$ for said peptide. Also, in the context of the present invention, an antibody is said to "specifically bind" or to "specifically recognize" a peptide if said antibody has an affinity constant $K_a$ higher than $10^7$ $M^{-1}$, preferably higher than $10^8$ $M^{-1}$, more preferably higher than $10^9$ $M^{-1}$ for said peptide and even more preferably higher than $10^{10}$ $M^{-1}$ for said peptide and has an affinity constant $K_a$ lower than $10^5 M^{-1}$ for all the other peptide.

The affinity constant which is used to characterize the binding of antibodies (Ab) to a peptide or an antigen (Ag) is the inverted dissociation constant defined as follows:

$$Ab + Ag \rightleftharpoons AbAg$$

$$K_a = \frac{[AbAg]}{[Ab][Ag]} = \frac{1}{K_d}$$

This affinity can be measured for example by equilibrium dialysis or by fluorescence quenching, both technologies being routinely used in the art.

The tested compound may be a monoclonal or a polyclonal antibody. This antibody may be of any species of origin, including (for example) mouse, rat, rabbit, horse, or human, or may be chimeric antibodies.

A "polyclonal antibody" as used herein, refers to an antibody that is obtained from different B cells. It may be produced by standard antibody production methods, for example by i) immunizing a suitable animal (e.g., rabbit, goat, etc.) with the phosphorylated protein of the invention or with an immunogenic peptide, ii) collecting immune serum from the animal, and iii) separating the polyclonal antibodies from the immune serum, in accordance with known procedures.

A "monoclonal antibody", as used herein, means an antibody arising from a nearly homogeneous antibody population. In other words, a monoclonal antibody consists of a homogeneous antibody arising from the growth of a single cell clone (for example a hybridoma, a eukaryotic host cell transfected with a DNA molecule coding for the homogeneous antibody, a prokaryotic host cell transfected with a DNA molecule coding for the homogeneous antibody, etc.) and is characterized by heavy chains of one and only one isotype and subtype, and light chains of only one type. The monoclonal antibodies of the invention may be produced in a hybridoma cell line according to the well-known technique of Kohler and Milstein, Nature 1975; Kohler and Milstein, Eur. J. Immunol. (1976); see also, CURRENT PROTOCOLS IN MOLECULAR BIOLOGY, Ausubel et al. (1989).

In a preferred embodiment, the compound of the invention is able to block the interaction of Apelin on its co-receptors APJ and GP130. In another preferred embodiment, said compound is able to block the Apelin-induced interaction of GP130 with APJ.

By "blocking an interaction", it is herein preferably meant that the said interaction cannot physically occur in the presence of the compound of the invention.

In another preferred embodiment, the compound of the invention is able to block both the mTOR and the STAT3 signaling pathways.

By "blocking a signaling pathway", it is herein meant that the said signaling pathway cannot be activated in the presence of the compound of the invention.

By blocking these interactions and/or signaling pathways, the compound of the invention will be able to inhibit CSC properties (e.g., CSCs potency, self-renewal and survival), and, consequently, will impair CSC proliferation and cancer progression.

In a preferred embodiment, the tested compound is a small molecule that is known to inhibit the interaction between APJ and Apelin. This small molecule is for example MM54 (Macaluso N J et al., 2011, ChemMedChem, 6 (6): 1017-23), which blocks Apelin-induced signaling and self-renewal in GSCs. Any other APJ antagonists may be used, such as ALX40-4C, [CRPRLC]-A-[CRPRLC], [CRPRLC]-AA-[CRPRLC], [CRPRLC]-GG-[CRPRLC], [CRPRLC]-HK-[CRPRLC], [CRPRLC]-KH-[CRPRLC], cyclo(1-6)QRPRLS, or cyclo(1-7)QRPRLSH as described in Macaluso N J et al., 2011, and in Macaluso N J et al., 2010.

In another preferred embodiment, the tested compound is an anti-sense nucleic acid such as a siRNA or a shRNA, said compounds having the following sequences:

```
siRNA specific for APJ:
CCAUCAUGCUGACCUGUUACUUCUU,      (SEQ ID NO: 10)

GACAACCAGUCUGAGUGUGAGUACA,      (SEQ ID NO: 11)

ACUAUGACUGGCCCUUUGGGACCUU       (SEQ ID NO: 21)

siRNA specific for Apelin:
GGUGCAGCCCAGAGGGUCAAGGAAU,      (SEQ ID NO: 12)

CCUCUCCCAUAAGGGACCCAUGCCU,      (SEQ ID NO: 13)

CCUGAUGCCGCUUCCCGAUGGGAAU       (SEQ ID NO: 14)

shRNA specific for Apelin:
TAACATTCTGTGATTCTTGGC,          (SEQ ID NO: 15)

TTACAAACATTGAACACAGGG,          (SEQ ID NO: 16)

AACAGGGCCTTAATATCTTTG,          (SEQ ID NO: 17)

AAGCAGACCAATCTATGGAGG,          (SEQ ID NO: 18)

TTTCTCTGCATTCTTCCCTGG           (SEQ ID NO: 19)

siRNA specific for GP130:
CUCACUUGCAACAUUCUUA             (SEQ ID NO: 20)
```

In another preferred embodiment, the tested compound is an antibody that is known to inhibit the interaction between APJ and Apelin.

Apelin-Dependent Signaling Pathway

The method of the invention comprises a step of detecting the activation level of at least one "Apelin-dependent signaling pathway" (step b).

By "Apelin-dependent signaling pathway", it is herein meant a signaling pathway whose activation is induced by Apelin. In the context of the invention, this signaling pathway is preferably activated by the interaction of Apelin with the membrane receptors APJ and GP130.

In a preferred embodiment, the detecting step b) comprises the detection and/or measurement of the activation level of the APJ receptor. This activation level can be assessed by any conventional means.

For example, activation level of the APJ transmembrane receptor can be assessed by measuring Calcium influx in cells expressing APJ coupled to a protein G receptor (Chemiscreen® from Millipore, Fluo4NW from Life Technologies), or by measuring the content of phosphorylated extracellular signal-regulated kinase (pERK) or Akt (pAkt) (Scimia M C, Nature letters 2012).

Alternatively, activation of the APJ receptor can be assessed by studying the recruitment of the scaffold molecule beta-arrestin2 to APJ. Said recruitment can be detected by any conventional means. Preferably, it is measured by immunofluorescence and microscopy analysis, co-immunoprecipitation, Fluorescence Resonance Energy Transfer (FRET) or by Bioluminescence Resonance Energy Transfer (BRET). These technologies are well known in the art.

Beta-arrestin2 is a scaffold protein, recruited upon GPCR activation and is involved in modulating GPCR trafficking and signaling (Shenoy S K et al., 2011). Beta-arrestin 2 is recruited to the plasma membrane upon activation of the membrane receptor APJ. APJ binding induces a global conformational change that involves the movement of the two arrestin domains and the release of its C-terminal tail that contains clathrin and AP2 binding sites. This conformational change can be reflected by Bioluminescence Resonance Energy Transfer (BRET) by using a vector expressing i) the bioluminescent Renilla luciferase (RLUC), ii) the beta-arrestin2 protein of SEQ ID NO:8 (P32121.2) and iii)

the yellow-emitting GFP mutant YFP. As a matter of fact, the emission spectrum of RLUC is sufficiently broad to provide good excitation of YFP.

In a specific embodiment of the method of the invention, the cells co-expressing APJ and GP130 are transfected by the RLuc-βarrestin2-YFP and subsequently stimulated with Apelin in the presence or in the absence of the tested compound. Light emission is detected (460-500 nm for RLUC and 510-550 nm for YFP) using conventional means. The BRET signal measuring beta-arrestin conformational change due to its recruitment to APJ is then determined as the ratio of the light emitted by YFP to that by RLUC. These values are preferably corrected by subtracting the background BRET RLUC signals detected when RLUC-beta-arrestin-YFP is expressed alone.

In this specific embodiment, Apelin-dependent activation of the APJ receptor is detected when the BRET signal is significantly increased in the presence of Apelin, as compared to control samples without Apelin polypeptide. Thus, the tested compound will be selected if, in the comparison step c), the BRET signal observed in the presence of Apelin is significantly decreased when said compound is added.

In one embodiment, the activation of the APJ receptor is assessed by assessing the activation status of an APJ-dependent signaling pathway. This APJ-dependent signaling pathway is for example the Akt/mTOR and ERK signaling pathways, calcium influx, and STAT3 activation.

In the context of the present invention, "the APJ-dependent signaling pathway" encompasses the APJ receptor itself, and/or a signaling pathway which is induced downstream of this receptor (e.g., the Akt/mTOR signaling pathway).

The mammalian target of rapamycin (mTOR) is an atypical serine/threonine kinase that is present in two distinct complexes, mTOR complex 1 and mTOR complex 2. The mTOR complex 1 (mTORC1) is composed of mTOR, Raptor, GβL (mLST8), and Deptor and is partially inhibited by rapamycin. mTORC1 integrates multiple signals reflecting the availability of growth factors, nutrients, or energy to promote either cellular growth when conditions are favorable or catabolic processes during stress or when conditions are unfavorable. Growth factors and hormones (e.g. insulin) signal to mTORC1 via Akt, which inactivates TSC2 to prevent inhibition of mTORC1. Alternatively, low ATP levels lead to the AMPK-dependent activation of TSC2 and phosphorylation of raptor to reduce mTORC1 signaling. Amino acid availability is signaled to mTORC1 via a pathway involving the Rag and Ragulator (LAMTORI-3) proteins. Active mTORC1 has a number of downstream biological effects including translation of mRNA via the phosphorylation of downstream targets (4E-BP1 and p70 S6 Kinase), suppression of autophagy (Atg13, ULK1), ribosome biogenesis, and activation of transcription leading to mitochondrial metabolism or adipogenesis. On another hand, the mTOR complex 2 (mTORC2) is composed of mTOR, Rictor, GβL, Sin1, PRR5/Protor-1, and Deptor and promotes cellular survival by activating Akt. mTORC2 also regulates cytoskeletal dynamics by activating PKCdelta and regulates ion transport and growth via SGK1 phosphorylation.

Akt, which exists as multiple isoforms, is one of the principle kinases activated by phosphoinositide 3-kinase (PI3K). Activation of PI3K results in the generation of phosphatidylinositol (3,4,5)-triphosphate (PIP5). These lipid second messengers bind to the pleckstrin homology domain of Akt to promote its translocation to the plasma membrane for activation via phosphorylation at Thr308 and Ser473 by PDK1 and the mTORC2 complex, respectively. Phosphorylation at both these sites is required for full activation of Akt Ser/Thr kinase activity. Akt phosphorylates over 50 known substrates, including GSK3b, p70S6K, 4EBP1, AS160, PRAS40, TSC 1, TCS 2, Raf-1, Bad, the FOXO family of transcription factors, and PFK2.

In the context of the invention, the Akt/mTOR signaling pathway is said to be activated for example when known substrates of either Akt or mTOR kinases (such as GSK3b, p70S6K, 4EBP1, AS160, PRAS40, TSC 1, TCS 2, Raf-1, Bad, the FOXO family of transcription factors, and PFK2) are substantially phosphorylated, as compared to control samples provided by kit manufacturers. Alternatively, the Akt/mTOR pathway is said to be activated when for example, Akt is phosphorylated on both Thr308 and Ser473, when mTOR is phosphorylated, or when S6, a substrate for p70S6K, is phosphorylated.

Akt activation is preferably assessed by conventional assays such as ELISA or Western Blots. For this purpose, commercial kits are available, for example the Akt pathway activation Profile InstantOne™ from Affymetrix eBioscience, the Alphascreen® assay from PerkinElmer. Anti-phosphorylated Akt antibodies are also available (Cell Signaling technology).

mTor activation is preferably assessed by ELISA or Western Blots. It can moreover be measured by cell-based imaging using antibodies anti-phospho mTOR (Pierce) or flow cytometry for pAkt or pS6 (Cell Signaling Technology).

In another embodiment, the detecting step b) of the method of the invention comprises the detection and/or measurement of the activation level of the GP130 receptor.

Activation level of GP130 can be directly measured by conventional means, for example by ELISA or western blot using antibodies recognizing specifically the Ser 782-phosphorylated form of GP130 (Santa Cruz).

In a preferred embodiment, GP130 activation level is assessed by measuring the activation level of a GP130-dependent signaling pathway. This GP130-dependent signaling pathway is for example the JAK/STAT3 signaling pathway. Additionally, MAPK and PI3K could be activated.

In the context of the present invention, "the GP130-dependent signaling pathway" encompasses the GP130 receptor itself, and/or a signaling pathway which is induced downstream of this receptor (e.g., the STAT3 signaling pathway).

The activation level of the STAT3 signaling pathway can be measured by any conventional means. Commercial kits, such as Flowcellect™ (Millipore), are available in this purpose.

Also, the skilled person may detect STAT3 activation level by western blot or by ELISA using an antibody which is specific to Tyr705- and Ser727-phosphorylated STAT3 (supplied for example by Cell Signaling Technology).

In a specific embodiment, the activation level of the STAT3 signaling pathway is detected by measuring the expression level of a reporter protein (e.g., a luminescent or a fluorescent reporter protein), whose expression is operatively linked to the STAT3 promoter of SEQ ID NO:9. The skilled person is well aware of the specific conditions that are to be used for this assay. Particular conditions are nevertheless precisely disclosed in the experimental part below. Briefly, plasmids expressing the firefly luciferase constructs downstream of STAT3 promoter can be transfected into cells co-expressing GP130 and APJ, and these cells can be treated with Apelin (preferably 24 hours after transfection). The STAT3-dependent luciferase signal can be measured once the candidate compound is added. The firefly luciferase signal should be observed only in the presence of a functional interplay between Apelin, APJ and GP130.

In this specific embodiment, activation of the GP130 receptor is detected in the presence of Apelin when the activation level of the STAT3 pathway, and, in particular, the expression level of the reporter protein placed under control of the STAT3 promoter, is significantly increased as compared to control samples without Apelin polypeptide. Thus, the tested compound will be selected if, in the comparison step c), the expression of the reporter protein under control of the STAT3 promoter observed in the presence of Apelin is significantly decreased when said compound is added.

In another embodiment, the detecting step b) of the method of the invention comprises the detection and/or measurement of the physical interaction between the co-receptors APJ and GP130. Detection can be achieved through imagery- and/or biochemical-based approaches.

In a preferred embodiment, the detecting step b) of the method of the invention comprises i) the detection and/or measurement of a GP130-dependent signaling pathway (e.g., of the GP130 receptor or of the STAT3 signaling pathway), and ii) the detection and/or measurement of the activation level of an APJ-dependent signaling pathway (e.g., of the APJ receptor or of the Akt/mTOR signaling pathway). These activation levels can be assessed by any conventional methods, as mentioned previously.

In this preferred embodiment, the tested compound will be selected if, in the comparison step c), i) the activation level, in presence of Apelin, of the GP130 receptor or of the GP130-dependent signaling pathway and ii) the activation level, in presence of Apelin, of the APJ receptor or of the APJ-dependent signaling pathway is significantly decreased when said compound is added.

In this specific embodiment, step b) of the method of the invention may contain any combination of these assays, provided that both APJ- and GP130-dependent signaling pathways are assessed. In particular, it is possible to measure, in cells co-expressing APJ and GP130, in the presence of the Apelin polypeptide and optionally the tested compound:

either i) the activation level of the GP130 receptor and the activation level of the APJ receptor, ii) the activation level of the GP130 receptor and the activation level of an APJ-dependent signaling pathway (e.g., of the Akt/mTOR signaling pathway), or iii) the activation level of a GP130-dependent signaling pathway (e.g., of the STAT3 signaling pathway) and the activation level of the APJ receptor, or iv) the activation level of a GP130-dependent signaling pathway (e.g., of the STAT3 signaling pathway) and the activation level of an APJ-dependent signaling pathway (e.g., of the Akt/mTOR signaling pathway).

In the method of the invention, the assessment of the activation status of the two signaling pathways may be performed in any order, or simultaneously. In other words, assessment of the activation level of GP130 or of the GP130-dependent signaling pathway can be performed simultaneously, before or after the activation level of APJ or of the APJ-dependent signaling pathway is assessed.

Yet, in a preferred embodiment, assessment of the activation level of GP130 or of the GP130-dependent signaling pathway is performed before the activation level of APJ or of the APJ-dependent signaling pathway is assessed.

In another preferred embodiment, the measurement of the activation level of APJ or of the APJ-dependent signaling pathway is performed only if the tested compound significantly decreases the Apelin-dependent activation of GP130 or of the GP130-dependent signaling pathway.

In practice, the activation status of the two signaling pathways may be performed independently. Consequently, the skilled person may use different cells for assessing the two different signaling pathways, provided that they express GP130 and APJ. Alternatively, the activation of the two signaling pathways may be assessed on the same cells.

In a preferred embodiment, the detecting step b) of the method of the invention comprises the detection and/or measurement, in cells co-expressing APJ and GP130, in the presence of the Apelin polypeptide and optionally the tested compound, of:

b1) the activation level of the STAT3 signaling pathway, and b2) the beta-arrestin2 recruitment to APJ.

More precisely, the detecting step b) of the method of the invention comprises the steps of:

b1) measuring, in cells co-expressing APJ and GP130, in the presence of the Apelin polypeptide and optionally the tested compound, the expression of a reporter protein whose expression is operatively linked to the STAT3 promoter of SEQ ID NO:9, and b2) measuring, in cells co-expressing APJ and GP130, in the presence of the Apelin polypeptide and optionally the tested compound, the Apelin-dependent beta-arrestin2 recruitment to APJ, preferably by BRET.

In a preferred embodiment, the two steps b1) and b2) are performed in this order (b2 following b1). More precisely, the step b2) is performed only if the tested compound significantly decreases the Apelin-dependent activation level of the reporter protein expression measured in step b1). As a matter of fact, the STAT3 pathway integrates all the tested signaling pathways. Hence, if a compound does not block the Apelin-dependent STAT3 activation, then this compound is unlikely to affect GSCs properties, although it may be efficient to affect the APJ-dependent ERK activation.

In the context of the invention, it is meant that the activation level of the receptors or of the signaling pathway depending thereof is "significantly increased" in the presence of Apelin (and in the absence of the tested compound) if the value measured in step b), b1) or b2) in the recombinant cells expressing GP130 and APJ in presence of Apelin is 2 fold superior, preferably 4 fold, and more preferably 6 fold superior to the value measured in these cells in absence of Apelin (and in absence of the tested compound).

Conversely, it is meant that the activation level of the receptors or of the signaling pathway depending thereof is "significantly decreased" in the presence of the tested compound if the value measured in step b), b1) or b2) in the recombinant cells expressing GP130 and APJ in presence of Apelin is 2 fold inferior, preferably 4 fold, and more preferably 6 fold inferior to the value obtained in these cells in absence of the tested compound (but in presence of Apelin).

Therapeutic Use of the Selected Compounds

In another aspect, the present invention relates to a method to inhibit CSC properties (e.g., CSCs potency, self-renewal and survival), said method comprising the step of contacting these cells with a compound that is able to:

a) inhibit the physical interaction of Apelin on its coreceptors APJ and GP130, or b) inhibit the physical interaction of the coreceptors APJ and GP130, or c) inhibit simultaneously the mTOR and STAT3 signaling pathways.

Preferably, said compound is not PTEN nor any PTEN-related molecule. As a matter of fact, mTOR effect on CSCs survival is independent on PTEN (Galan-Moya et al., 2011).

This method can be performed in vitro or in vivo.

This compound is preferably an anti-sense nucleic acid, a small chemical molecule or an antibody.

In a preferred embodiment, this compound is the small molecule MM54, or cyclo(1-6)CRPRLC-KH-cyclo(9-14) CRPRLC, which blocks Apelin-induced signaling and self-renewal in GSCs (Macaluso N J et al., 2011).

This compound is indeed capable of in vivo inhibiting tumor growth once initiated (see results FIGS. 6E and 9). This effect could be due, at least in part, to its anti-angiogenic effect, to its anti-proliferative effect, or to its negative effect on GSC survival, as observed by the inventors (see FIG. 9).

Moreover, the inventors observed that the engraftment of GSCs in which APJ is downregulated (by means of two different shRNAs anti-APJ) is prevented (FIG. 4H).

Any other APJ antagonists may be used, such as ALX40-4C, [CRPRLC]-A-[CRPRLC], [CRPRLC]-AA-[CRPRLC], [CRPRLC]-GG-[CRPRLC], [CRPRLC]-HK-[CRPRLC], [CRPRLC]-KH-[CRPRLC], cyclo(1-6)QRPRLS, or cyclo(1-7)QRPRLSH as described in Macaluso N J et al., 2011 and in Macaluso N J et al., 2010).

The compound of the invention, and in particular the MM54 compound, may thus be used to prevent and/or treat cancers involving CSCs, in particular GSCs.

In a preferred embodiment, the compound of the invention, and in particular MM54, may be used to inhibit cancer-associated angiogenesis.

In another preferred embodiment, the tested compound is an anti-sense nucleic acid such as a siRNA or a shRNA, said compounds having the following sequences:

```
siRNA specific for APJ:
CCAUCAUGCUGACCUGUUACUUCUU,    (SEQ ID NO: 10)

GACAACCAGUCUGAGUGUGAGUACA,    (SEQ ID NO: 11)

ACUAUGACUGGCCCUUUGGGACCUU     (SEQ ID NO: 21)

siRNA specific for Apelin:
GGUGCAGCCCAGAGGGUCAAGGAAU,    (SEQ ID NO: 12)

CCUCUCCCAUAAGGGACCCAUGCCU,    (SEQ ID NO: 13)

CCUGAUGCCGCUUCCCGAUGGGAAU     (SEQ ID NO: 14)

shRNA specific for Apelin:
TAACATTCTGTGATTCTTGGC,        (SEQ ID NO: 15)

TTACAAACATTGAACACAGGG,        (SEQ ID NO: 16)

AACAGGGCCTTAATATCTTTG,        (SEQ ID NO: 17)

AAGCAGACCAATCTATGGAGG,        (SEQ ID NO: 18)

TTTCTCTGCATTCTTCCCTGG         (SEQ ID NO: 19)

siRNA specific for GP130:
CUCACUUGCAACAUUCUUA           (SEQ ID NO: 20)
```

In another preferred embodiment, the tested compound is an antibody that is known to inhibit the interaction between APJ and Apelin.

It is to be noted that the role of the APJ/Apelin signaling pathway in tumor angiogenesis is still matter of debate. Some studies unveiled that Apelin induces tumor angiogenesis (Rayalam S. et al, 2011), whereas others demonstrated that it induces vascular normalization that eventually induce an anti-tumor effect (Kidoya et al., 2012). Moreover, no study ever disclosed the role of APJ/Apelin pathway on the survival of CSCs, as the present invention does. Altogether, this means that the skilled person was not encouraged using inhibitors of the Apelin pathway for impairing CSCs properties.

This compound is hereafter referred to as the "compound of the invention".

Importantly, the compound of the invention will selectively target cancer stem cells (and not normal stem cells), because only these cells have developed an addiction to the APJ/GP130 pathway and to the downstream activation of the Akt/mTOR and STAT3 pathways. Moreover, blocking Apelin/APJ/GP130 signaling will not target differentiated cells (either normal or cancerous cells) because APJ is lost upon their differentiation. Consequently, the compound of the invention will selectively target CSCs while sparing healthy stem cells and differentiated cells so that they will have few side effects.

Hence, the compound of the invention could be used for preventing and/or treating cancer patients, preferably those suffering from breast cancer, head and neck cancer, lung cancer, ovarian cancer, pancreatic cancer, colorectal carcinoma, cervical cancer, sarcomas, brain tumors, renal cancer, prostate cancer, melanoma and skin cancers, gastric cancer, multiple myeloma, leukemia or lymphoma, that are known to involve CSCs. In a preferred embodiment, this compound is used for preventing and/or treating glioblastoma.

Because it may not affect non-stem cancer cells, this compound could advantageously be used in combination with at least one traditional chemotherapeutic drug, such as a DNA-damaging agent, an anti-mitotic agent, and/or an antimetabolite agent.

The said DNA-damaging agent can be an alkylating agent, a topoisomerase inhibitor and/or a DNA intercalator. The said alkylating agent is preferably selected in the group consisting of: chlorambucil, cyclophosphamide, ifosfamide, mechlorethamine, melphalan, uracil mustard, thiotepa, busulfan, carmustine, lomustine, streptozocin, carboplatin, cisplatin, satraplatin, oxaliplatin, altretamine, ET-743, XL1 19 (becatecarin), dacarbazine, chlormethine, bendamus tine, trofosfamide, uramustine, fotemustine, nimustine, prednimustine, ranimustine, semustine, nedaplatin, triplatin tetranitrate, mannosulfan, treosulfan, temozolomide, carboquone, triaziquone, triethylenemelamine, and procarbazin. The said topoisomerase inhibitor is preferably selected in the group consisting of: doxorubicin (doxil), daunorubicin, epirubicin, idarubicin, anthracenedione (novantrone), mitoxantrone, mitomycin C, bleomycin, dactinomycin, plicatomycin, irinotecan (camptosar), camptothecin, rubitecan, belotecan, etoposide, teniposide, and topotecan (hycamptin). The said DNA intercalator is preferably selected in the group consisting of proflavine, doxorubicin (adriamycin), daunorubicin, dactinomycin, and thalidomide.

The said antimitotic agent is preferably selected in the group consisting of: paclitaxel (abraxane)/taxol, docetaxel (taxotere), BMS-275183, xyotax, tocosal, vinorlebine, vincristine, vinblastine, vindesine, vinzolidine, etoposide (VP-16), teniposide (VM-26), ixabepilone, larotaxel, ortataxel, tesetaxel, and ispinesib.

The said antimetabolite agent is preferably selected in the group consisting of: fluorouracil (5-FU), floxuridine (5-FUdR), methotrexate, xeloda, arranon, leucovorin, hydroxyurea, thioguanine (6-TG), mercaptopurine (6-MP), cytarabine, pentostatin, fludarabine phosphate, cladribine (2-CDA), asparaginase, gemcitabine, pemetrexed, bortezomib, aminopterin, raltitrexed, clofarabine, enocitabine, sapacitabine, and azacitidine.

Further anticancer chemotherapy, and examples of suitable therapeutic protocols, maybe found in books such as *Cancer Chemotherapy and Biotherapy: Principles and Practice,* 3rd ed. (2001), Chabner and Longo, eds., and *Handbook of Cancer Chemotherapy,* 6th ed. (2003), Skeet, ed., both from Lippincott Williams & Wilkins, Philadelphia, Pa., U.S.A.; Moreover, regimens for anticancer therapies, especially chemotherapies, may be found on Web sites such as those maintained by the National Cancer Institute (www.cancer.gov), the American Society for Clinical Oncology (www.asco.org), and the National Comprehensive Cancer Network (www.nccn.org). An association of the compounds of the invention with for example anti-angiogenic molecules (such as bevazicumab) is preferably considered.

In another aspect, the present invention relates to a method for preventing and/or treating cancer by inhibiting Cancer Stem Cells (CSCs) properties, comprising the step of administering in a subject in need thereof an efficient amount of the compound of the invention. This compound is advantageously administered before, simultaneously or after one or more traditional chemotherapeutic drug (e.g., a DNA-damaging agent, an anti-mitotic agent, and/or an antimetabolite agent, as disclosed above).

As used herein, the term "subject" refers to any animal (e.g., a mammal), including (but not limited to) human, non-human primates, rodents, and the like, which is to be the recipient of a particular treatment. Typically, the terms "subject" and "patient" are used interchangeably in reference to a human subject.

In yet another aspect, the present invention relates to a pharmaceutical composition containing the compound of the invention and a pharmaceutically acceptable carrier. This pharmaceutical composition is used preferably for preventing and/or treating cancers in subjects in need thereof.

The term "pharmaceutically acceptable carriers" refer to molecular entities and compositions that do not produce any adverse, allergic, or other untoward reaction when administered to an animal, or a human, as appropriate. Veterinary uses are equally included within the invention and "pharmaceutically acceptable" formulations include formulations for both clinical and/or veterinary use. As used herein, "pharmaceutically acceptable carrier" includes any and all solvents, dispersion media, coatings, anti-bacterial, and anti-fungal agents, isotonic and absorption delaying agents, and the like. The use of such media and agents for pharmaceutically active substances is well known in the art.

As used herein with respect to these methods, the term "administering" refers to various means of introducing a composition into a subject or a patient. It is intended to include (but is not limited to) subcutaneous injection, intravenous injection, intraocular injection, intracranial injection or implant, intradermal injection, intramuscular injection, intraperitoneal injection, intratracheal administration, epidural administration, inhalation, intranasal administration, oral administration, sublingual administration, buccal administration, rectal administration, vaginal administration, and topical administration.

As used herein, the term "effective amount" refers to an amount that will result in the desired result and may readily be determined by one of ordinary skill in the art. The compositions of the present invention may be formulated for various means of administration. These means are well known in the art and may include, for example, injection; tablets, pills, capsules, or other solids for oral administration; nasal solutions or sprays; aerosols, inhalants; topical formulations; liposomal forms; and the like.

Prognostic Use of Apelin

Gliomas may be classified by cell type, by grade, and by location. Among the different cell types, astrocytomas originate from star-shaped brain cells in the cerebrum called astrocytes. This type of tumor does not usually spread outside the brain and spinal cord and it does not usually affect other organs. Astrocytomas are the most common glioma and can occur in most parts of the brain and occasionally in the spinal cord. It is classified as a low-grade glioma of grade II by the World Health Organization (WHO). High-grade [WHO grade III-IV] gliomas such as glioblastoma are undifferentiated or anaplastic; these are malignant and carry a worse prognosis.

The results of the present inventors revealed that Apelin expression is significantly elevated in glioma samples of grades II-IV when compared to non-tumour brain tissues (cf. FIG. 8). Remarkably, Apelin was found more abundant in the mesenchymal subtypes, which are those of worse prognosis and higher resistance among grade IV (cf. FIG. 17). In line with this, patients with up-regulated Apelin expression or amplified copy number exhibit a significantly lower probability of survival (cf. FIGS. 8 and 17). Altogether, these results suggest that high Apelin levels are associated with poorer prognosis and reduced patient survival.

In another aspect, the present invention relates to the use of Apelin expression level for evaluating the survival probability of a subject suffering from glioblastoma.

Expression of Apelin may be determined either at a nucleic acid level (mRNA) or at a protein level, by any conventional means (Western-Blot, Northern Blot, immunohistochemistry, etc). This expression level is preferably measured in a biological sample of said tumour, for example obtained by biopsy.

In a preferred embodiment, the present invention relates to an in vitro method for predicting the survival probability of a subject suffering from glioblastoma, comprising the steps of:

a) determining the expression level of Apelin in a biological sample of the tumour, b) comparing said expression level to a reference value, c) concluding, from said comparison, that the said subject has a high or low survival probability.

In the context of the invention, the "reference value" corresponds to the basal expression level of Apelin in non-tumour brain tissues, as assessed by the technique which will be used in step a) (Western-Blot, Northern Blot, immunohistochemistry, etc.).

Preferably, a high survival probability will be prognosed if the expression level of Apelin in the tested sample is significantly superior to the said reference value. Conversely, a low survival probability will be prognosed if the expression level of Apelin in the tested sample is significantly inferior to the said reference value.

The expression level of Apelin will be held as "significantly superior to" the reference value if the ratio between same is strictly superior to 1.5, preferably to 2, more preferably to 5.

Conversely, the expression level of Apelin will be held as "significantly inferior to" the reference value if the ratio between same is strictly inferior to 0.75, preferably to 0.5, more preferably to 0.2.

A "high survival probability" herein means that the tested subject will have a mean survival period which is likely to be superior to 300 days, preferably superior to 400 days, after the sample has been collected.

A "low survival probability" herein means that the tested subject will have a mean survival period which is likely to be inferior to 300 days, preferably superior to 200 days, after the sample has been collected.

EXAMPLES

I. Materials and Methods

Cell culture, Conditioned Media Preparation and Apelin Secretion

Patient-derived GSCs #1 to 4 were described previously in (Patru et al, 2010), GSCs #5 to 17 were obtained from Hospital Laennec, Nantes, France. Briefly, tumors were dissociated using the gentleMACs Dissociator (Miltenyi), according to the manufacturer's instructions. GSCs #1 to 17 were maintained in DMEM/F12 plus N2, G5 and B27 (Life Technologies).

Immortalized human brain microvascular endothelial cells (hCMEC/D3) were cultured as described previously (Weksler et al, 2005) and HEK-293T in DMEM 10% FBS plus antibiotics (Invitrogen). Conditioned media from hCMEC/D3 (EC-CM) and HEK-293T (293T-CM) were obtained from 72 h-old monolayers in serum-free EBM2 (Lonza). The concentration of Apelin in CM was quantified using the human Apelin EIA Kit development kit (Phoenix Pharmaceutical) as per the manufacturer's directions.

Plasmids, Reagents, and Transfections

HA-APJ construct was kindly supplied by Dr. L. Zheng (Chun et al., 2008) and pORF-GP130 was from InvivoGen. Transfections were performed in HEK-293T using Turbofect (Thermo Scientific). Recombinant Apelin was from Sigma-Aldrich. The APJ antagonist, MM54, cyclo(1-6)CR-PRLC-KH-cyclo(9-14)CRPRLC, was kindly supplied by Dr. Robert Glenn (Macaluso N J et al., 2011). Stealth non-silencing control and selected siRNA for human Apelin, APJ and GP130 were from Invitrogen and Sigma: siRNA specific for APJ (CCAUCAUGCUGACCUGUUAC-UUCUU, GACAACCAGUCUGAGUGUGAGUACA, ACUAUGACUGGCCCUUUGGGACCUU); siRNA specific for Apelin (GGUGCAGCCCAGAGGGU-CAAGGAAU, CCUCUCCCAUAAGGGACCCAUGCCU, CCUGAUGCCGCUUCCCGAUGGGAAU); siRNA specific for GP130 (CUCACUUGCAACAUUCUUA). Transfections were performed using RNAiMAX lipofectamine (Invitrogen). GIPZ Lentiviral shRNAs Apelin were purchased from Thermo Scientific (TAACATTCTGTGATTCT-TGGC, TTACAAACATTGAACACAGGG, AACAGGGC-CTTAATATCTTTG, AAGCAGACCAATCTATGGAGG, TTTCTCTGCATTCTTCCCTGG). Lentivirus production was performed as previously described (Galan et al 2011b). 48h post-infection, puromycin selection was initiated (Sigma, 1.5 mg/ml).

Secondary Neurosphere Formation

GSCs were dissociated by up-and-down pipetting and cultured in a 48-well plate format. Cells were dissociated again at days 1 and 2 after mitogen-deprivation and then maintained until day 3. NS counts were blindly performed on five random fields of view (fov) and the mean of neurosphere/fov was calculated from 3 independent experiments. Statistical analyses were performed using 2-way Student's test (Excel Microsoft Office).

RNA Extraction and RT-PCR

RNA was extracted using the Qiagen RNeasy Mini Kit as per the manufacturer's directions. Equal amounts of RNA were reverse transcribed using the Superscript III RT kit (Invitrogen) and the resulting cDNA was used to amplify APJ, Gp130, Sox2, Nestin and Oct4 mRNA by PCR using gene specific primer sets (table 1) in the presence of Red Taq DNA polymerase (Sigma). Human beta-actin was also amplified as a control for input. PCR products were separated by electrophoresis on SYBR green-containing agarose gels (Invitrogen) and DNA was visualized by UV illumination (Appligene).

Western Blot and Antibodies

Proteins were collected in TNT buffer (10 mM Tris-HCl pH 7.5, 150 mM NaCl, 1% Triton X100, 2 mM EDTA) plus protease inhibitors (Sigma), 200 mM NaF and 0.1 mM Na3VO4. Equal amounts of proteins (microBCA kit, Pierce) were separated with 4-12% Nupage gels (Invitrogen) and transferred onto PVDF membranes (Thermo Fisher Scientific). Alexa680-conjugated secondary antibodies (Invitrogen) were used and membranes were scanned using the Odyssey infrared imaging system (Licor). The following antibodies were used: phospho(p)-S-Akt, pT-Akt, p-S6, Akt total, p-Y-STAT3, p-S-STAT3, STAT3 (Cell Signaling), APC-APJ, control Ig and non-conjugated APJ (Millipore), GP130 (Abcam).

Co-Immunoprecipitations

For co-immunoprecipitation experiments, cells were lysed in HNTG buffer (20 mM Hepes pH 7.5, 150 mM NaCl, 0.1% Triton X-100, 10% Glycerol) plus protease inhibitors (Sigma), 200 mM NaF and 0.1 mM Na3VO4. Pre-clear post-nuclei supernatants were incubated with anti-APJ antibodies (2 μg/sample, Millipore). Protein G agarose (gamma Bind Sepharose, Sigma) was added for the last 45 min.

Equal amounts of proteins (microBCA kit, Pierce) were separated with 4-12% Nupage gels (Life Technologies) and transferred onto PVDF membranes (Thermo Scientific). Alexa 680-conjugated secondary antibodies (Life Technologies) were used and membranes were scanned using the Odyssey infrared imaging system (Licor).

The following antibodies were used: phospho (p)S-Akt, p-S6, Akt total, pS-STAT3, STAT3 (Cell Signaling), Gp130 (Santa Cruz), and APJ, Sox2 and Nestin (Millipore). Tubulin (Santa Cruz) was used as an internal loading control. Scans are representative of 3 independent experiments.

Luciferase Assay

HEK-293T cells were co-transfected with HA-APJ, GP130, STAT3 Luciferase Reporter Vector (Affymetrix) and Renilla (Promega). 24 h after transfection, cells were pretreated with the indicated drugs and th after exposed to Apelin during 6 h. Then, cells were lysed and STAT3 luciferase activity was measured using the Dual-Luciferase Reporter Assay (Promega).

Flow Cytometry

For cell surface expression analysis, cells were incubated with the conjugated antibody for th and then washed twice with cold PBS. Flow cytometry analyses were performed on Accuri cytometer (BD Biosciences, CYBIO facility, Institut Cochin) and processed using CFlow plus software (BD Biosciences).

BRET Analysis

HEK-293T cells expressing APJ, GP130 or co-expressing both receptors together with the RLuc-βarrestin2-YFP (kindly provided by Dr. M. Scott) were distributed in poly-lysine coated 96-well white microplates 24 h after transfection. Cells were then washed twice with PBS and incubated with coelenterazine h (final concentration of 50 nM in Hank's solution) for 10 min. Cells were subsequently stimulated with Apelin (1 μM) for the indicated times and light emission was detected (460-500 nm for Luc and 510-550 nm for YFP) using a multilabel reader (Mithras LB 940; Berthold Technologies). The BRET signal measuring beta-arrestin conformational change due to its recruitment was determined as the ratio of the light emitted by YFP to that by Luc. The values were corrected by subtracting the background BRET RLuc signals detected when RLuc-β arrestin-YFP was expressed alone.

Radioactivity Binding Assays Using Membrane Preparations

For the membrane fractions preparation, HEK-293T and GSC cells were lysed (5 mM Tris pH7.4 and 2 mM EDTA) and homogenized 4×5 sec using ultrathorax (IKA-Labortechnik, Germany). Homogenates were cleared by 5 min centrifugation at 3000 rpm. Then cells were resuspended in binding buffer (50 nM Hepes, 5 mM MgCl2 and 1% BSA) and ultracentrifuged to obtain cell membranes. Membranes were then incubated with [125I][<Glu65,Nle75,Tyr77]apelin-13 (Perkin Elmer) in 100 µl of the binding buffer at room temperature for 90 min. In order to determine the amounts of nonspecific binding, unlabeled [<Glu65, Nle75,Tyr77] apelin-13 (Sigma) was simultaneously added After incubation, bound and free radioactivities were separated through rapid filtration using the glass-fiber filter units (GF/C, Packard Instrument Co.) of a cell harvester (Packard). Filter units were completely dried, and Microcinti O (Packard) was added to each well. The radioactivity of each well was counted with a TopCount liquid scintillation counter (Packard). The dissociation constant (Kd) and the number of binding sites (B max) were determined by the method of Scatchard.

Receptor Binding Assays Using Intact Cells.

Prior to binding experiments, $2 \times 10^6$ GSCs were washed three times with DMEM/F12, and resuspended in binding buffer (DMEM/F12, 40 mM HEPES, 1% BSA). In order to determine the amount of nonspecific binding, 1 µM unlabeled [<Glu$^{65}$, Nle$^{75}$, Tyr$^{77}$]apelin-13 was added. Cells were pre-incubated with GP130 blocking antibody (2 µg/ml) when indicated. Cells were then incubated with 400 pM [$^{125}$I][<Glu$^{65}$,Nle$^{75}$,Tyr$^{77}$]apelin-13 in agitation for 6 h at 4° C., and radioactivity was measured with a gamma counter (Beckman).

Animals, Histology and Tumour Initiation and Progression

All animal studies were carried out according to French Ministry approved protocols (agreement number #00754.02), in compliance with the European Convention for the Protection of Vertebrate Animals used for Experimental and other Scientific Purposes (ETS 123). Six weeks old females BALB/c nude mice (Janvier) were subcutaneously injected with $1*10^6$ cells in 100 µl 1:1 PBS and growth factors-free matrigel (Corning). For tumour initiation (FIG. 9), mice were examined weekly in the search for tumours and sacrificed 7 weeks after implantation. For pharmacological studies (FIG. 6), mice were treated twice per week with MNI54 or vehicle (DMSO) diluted in PBS (100 µl) (intraperitoneal injection for 7 weeks), once tumours were detected (4 weeks post-implantation).

Upon sacrifice, tumours were extracted, embedded in OCT (Tissue Tek) in biomoulds, frozen by immersion in dry ice-chilled isopentane for 1 min, and stored at −80° C. for further analysis.

For immunostaining, embedded OCT-tumours were cut in 7 µm sections using a CM350S Leica cryostat (Histology platform, Institut Cochin, Paris). Pre-warmed frozen sections (30 min, RT) were fixed for 30 min in PBS-paraformaldehyde 4% and permeabilised (PBS-Triton 0.5%, 15 min) prior a 2 hours blocking step (3% BSA in PBS). Primary antibodies (PECAM from BD, and Ki67 and Nestin from Millipore) were incubated overnight at 4° C. in blocking buffer. Sections were extensively rinsed in PBS and incubated with suitable species-specific Alexa Fluor-coupled secondary antibodies (Life Technologies) for 1 h RT. Slides were mounted in DAPI mounting medium. Cell death was estimated through the Tunel assay kit (TACS 2 TdT-Fluor. In situ detection kit, Trevigen) as per the manufacturer's instructions.

A minimum of 3 tumour sections per condition was used, with at least 5 different fields of view (fov) each. For blood vessel surface analysis, PECAM pixel intensity was calculated in each fov and an average+sem of the total fov was represented. Cell proliferation was assessed through the percentage of Ki67-positive cells normalized to the total cell number of cells in DAPI. Nestin positive cells were counted per fov.

Image Acquisition

Image acquisitions were performed on TCS/SP4 Leica confocal microscope (Institut A. Lwoff, Villejuif, France) and Spinning Disk Leica microscope (Institut Cochin, Paris, France) using Leica Application Software (LAS) and Metamorph, respectively. Image J software was used to adjust brightness, contrast and picture size (Rasband, W. S., ImageJ, U.S. National Institutes of Health, Bethesda, Md., USA, http://imagej.nih.gov/ij/, 1997-2014).

Statistical Analysis

Data are representative of at least 3 independent experiments. Statistical analysis was performed with GraphPad Prism6 or Microscoft Office Excel software using two-way analysis of variance (ANOVA) and an unpaired two-tailed t-test (Student's t test), as specified in the legends to figures. In Kaplan-Meier survival curves, differences were compared by log-rank analysis.

Results

Endothelium-Secreted Apelin Sustains GSC Sternness

The 13 amino-acid peptide Apelin was found to be released, among many other proteins, in an endothelial cell conditioned media (EC-CM) (FIG. 1, 2A-B). Interestingly, recombinant Apelin was sufficient to support self-renewal in a panel of 16 patient-derived GSCs, as evidenced by secondary neurosphere formation and Sox2/Nestin expression (FIG. 2C-D). Conversely, Apelin-depleted EC-CM failed to maintain GSC self-renewal (FIG. 2G).

To investigate whether Apelin could operate as a paracrine signal to preserve the GSC subset, recombinant Apelin was applied to GSCs in mitogen-free (MF) media (FIG. 11a). While readily detected in mitogen-containing media (NS), Nestin and Sox2 expression was abolished in GSCs upon mitogen withdrawal (MF conditions), along with a significant drop of secondary tumoursphere formation (FIG. 11b-c). Conversely, cell death was increased (FIG. 11d). These self-renewal markers were however maintained in the presence of Apelin (FIG. 11b-c and FIG. 12). In keeping with this, Apelin also hindered mitogen deprivation-induced cell death (FIG. 11d). RNA interference was then used to knock down Apelin in endothelial cells. It was found that conditioned media (CM) from Apelin-silenced endothelial cells was unable to support cell survival in a panel of 16 patient-derived GSCs (FIG. 11e-h). The addition of exogenous Apelin into depleted endothelial cell-derived media restored EC-CM-sustained self-renewal and viability (FIG. 11i-k). In contrast to Apelin, Toddler/Elabela, which was recently identified as an alternate APJ ligand did not recapitulate the Apelin effects on GSCs (not shown). Thus, Apelin is an essential endothelial factor needed for GSC maintenance and survival. Other APJ agonists (namely ML233, Apelin 13 and Apelin 36) have been shown to promote GSC survival through APJ/GP130 and mTOR pathway (cf. FIG. 13).

Importantly, the results presented on FIG. 11 (d, h, k) show that Apelin has an effect on GSCs survival (not only proliferation).

To explore the role of Apelin in human GBM, a retrospective analysis of its expression was conducted using the National Cancer Institute's Repository for Molecular Brain Neoplasia Data (REMBRANDT). This revealed that Apelin expression was significantly elevated in glioma samples (grades II-IV) when compared to non-tumour brain tissues (see FIG. 8a). Remarkably, Apelin was found more abundant in the mesenchymal subtype (Yan et al, 2013; Verhaak et al., 2010), which are those displaying worse prognosis and higher resistance among grade IV (FIG. 8b-c). In line with this, patients with up-regulated gene expression or amplified copy number exhibit a significantly lower probability of survival (see FIG. 8d-e). Remarkably, APLN was found more abundant in the mesenchymal subtypes, which are those displaying worse prognosis and higher resistance among grade IV (cf. FIG. 17). Hence, this set of data indicated that GBM present heightened Apelin levels that are associated with poorer prognosis and reduced patient survival.

Apelin Maintains Neurosphere Integrity Through APJ Signaling to mTOR

APJ, the cognate receptor for Apelin, belongs to the G protein-coupled receptor family. APJ is related to the angiotensin II receptor and has been described as a co-receptor involved in the mediation of HIV-1 neuropathogenesis, cardiovascular and neuroendocrine functions. APJ expression was detected in patient-derived self-renewing GSCs, but not upon their differentiation, at the RNA and protein level (FIG. 3A-C). APJ was notably absent from glioblastoma cell lines (FIG. 3D). Moreover, cancer stem-like cells but not normal stem cells from different tissues express APJ (FIG. 3E-F). We have previously demonstrated the importance of the Akt/mTor pathway for GSC properties. In line with this, recombinant Apelin was able to activate this pathway in a similar extend than EC-CM (FIG. 4A). More interestingly, Apelin-depleted EC-CM failed to do so (FIG. 4B), suggesting that Apelin could be a key factor for EC-mediated Akt/mTor pathway activation. Furthermore, reduction of APJ expression through RNA interference effectively hampered mTor activation, triggered by both EC-CM and recombinant Apelin (FIG. 4C-D). Similarly, APJ pharmacological inhibition was able to reduce both EC-CM and Apelin-induced Akt/mTor activation (FIG. 4E). Finally, targeting APJ through either siRNA or pharmacological antagonist dramatically decreased neurosphere number and size, when GSCs were cultured with EC-CM, along with Sox2/Nestin diminution (FIG. 4F).

Apelin co-opts GP130 to fully activate APJ-dependent mTOR pathway mTOR is known to phosphorylate STAT3. It was thus decided to evaluate STAT3 signaling in response to both EC-CM and recombinant Apelin. Interestingly, both recombinant and endothelial-derived Apelin were able to activate this signaling pathway (FIG. 5A). Furthermore, interfering with APJ in GSCs or Apelin in endothelial cell was sufficient to reduce STAT3 phosphorylation (FIG. 5B).

It is well described that GP130 can function as a signal transducer for many cytokine receptors involved in sternness, such as LIFR and CNTFR. Therefore, it was investigated whether GP130 could play a role as well in Apelin/APJ signaling. Interfering with GP130 expression through siRNA showed that GP130 is strictly required for EC-CM-mediated Akt/mTor pathway activation (FIG. 5C). Moreover, a GP130 blocking antibody also efficiently blocked Akt/mTor pathway activation in response to both EC-CM and recombinant Apelin (FIG. 5D). Using a similar approach, we evaluated the impact of GP130 blockade on GSC sternness. Noticeably, interfering with GP130 dramatically decreased the number and size of neurosphere cultured with EC-CM, while it barely affected those of GSCs growing in control medium (FIG. 5E).

This set of data points for a role of GP130 as a signal transducer in APJ/Apelin axis. Thus, recombinant Apelin triggered the activation of the mTor signalling cascade, as illustrated by Akt, S6 and STAT3 phosphorylation, in the absence of any other exogenous mitogen, as did EC-CM and NS. Conversely, EC-CM from Apelin-depleted cells failed to do so. Likewise, blocking mTor pharmacologically with rapamycin or genetically by RNA interference jeopardized Apelin protective effects on GSCs (not shown), reinforcing the idea that Apelin is central in endothelial-mediated mTor activation. The Apelin-triggered signalling downstream of APJ was examined in patient-derived GSCs. The reduction of APJ gene expression quelled EC-CM- and recombinant Apelin-triggered S6, Akt and STAT3 phosphorylation. Functionally, endothelial-mediated cell survival and self-renewal relied on APJ expression (FIG. 4G). Of note, exogenous mitogens contained in the growth medium were sufficient to bypass Apelin-APJ dependence (NS conditions, FIG. 4G). Lastly, the impact of APJ silencing on tumour initiation in vivo was analysed by implanting GSCs retrovirally infected with short interfering RNA against APJ in mice. Reducing APJ levels in GSCs markedly decreased the occurrence of tumours when compared to APJ-expressing GSCs (FIG. 4H). The few resulting tumours displayed weak Nestin staining and lower vascularisation index (FIG. 4I). Collectively, these data demonstrate that endothelial-released Apelin sustains GSC integrity and is an essential mediator of their survival through the mTor pathway.

Interplay Between APJ and GP130

We then deciphered the interplay between APJ and GP130 in response to Apelin stimulation. First, we observed that GP130 was strictly required for Apelin-mediated STAT3 and APJ activation, as evidenced by luciferase-based reporter and BRET assays, respectively (FIG. 6A-B). Interestingly, endogenous APJ and GP130 co-localize in GSC neurospheres (not shown). Although GP130 was not required for Apelin binding to APJ (FIG. 6C), treatment with a blocking antibody prevented from Apelin binding (FIG. 6D). Interestingly, flow cytometry analysis revealed that GP130 modulated APJ surface availability (not shown). More precisely, APJ expression was significantly decreased at the cell surface in GP130-silenced cells, although APJ total level remained unchanged (not shown). Conversely, in HEK-293T cells, overexpressed GP130 potentiated APJ availability at the cell surface. These observations offer support for a role of GP130 in APJ localization at the plasma membrane.

Meanwhile, endogenous GP130 expression did not alter agonist-induced APJ internalisation (not shown).

Moreover, it was found that targeting GP130 hampered GSCs sustainability in a very similar manner to that observed when interfering with APJ, when cultured in apelin-containing media, either produced by endothelial cells or provided as a purified peptide (FIG. 10j-m). Such effects were recapitulated using the non-peptide APJ agonist ML233 (not shown). Thus, GP130 maintains APJ at the plasma membrane to marshal apelin/APJ signalling in GSCs.

Physical Interaction Between APJ and GP130

To identify new partners for APJ in the context of GSCs, we performed a series of co-immunoprecipitation experiments with an emphasis for membrane proteins. This led to the identification Gp130 as part of the APJ interactome (FIG. 10a). This single spanned glycoprotein often serves as a co-receptor for LIF (leukemia inhibitory factor), IL-6 (interleukin 6) and EPO (erythropoietin) cytokine receptors, while tightly associated with STAT3 signalling. Its expression was homogeneous in patient-derived GSCs. The association between APJ and Gp130 was also directly visualised in cells in a Duolink technology assay, further highlighting their close proximity (<40 nm distance between the two receptors) (FIG. 10b). In addition, Bioluminescence Resonance Energy Transfer (BRET) assays revealed that Gp130 and APJ cooperate to promote β-arrestin activation (FIG. 10c), suggesting that APJ alone was not sufficient to fully recapitulate a functional G-protein coupled receptor, when overexpressed in HEK-293T cells. Accordingly, knocking down Gp130 or blocking its activity with an antibody blunted endothelial- and Apelin-mediated mTor activation and the subsequent STAT3 promoter activation (FIG. 10d-e). Although APJ total level remained even in Gp130-silenced cells, its expression was significantly decreased at the cell surface (FIG. 10i). In HEK-293T cells, overexpressed Gp130 potentiated APJ availability at the cell surface. These observations offer support for a role of Gp130 in APJ localization at the plasma membrane. Finally, we found that targeting Gp130 hampered GSCs sustainability in a very similar manner to that observed when interfering with APJ, when cultured in Apelin-containing media, either produced by endothelial cells or provided as a recombinant protein (FIG. 10j-m). Thus, Gp130 maintains APJ at the plasma membrane to marshal Apelin/APJ signalling in GSCs.

Inhibition of Tumour Growth

Finally, the effects of Apelin signaling in tumor initiation and progression were assessed in vivo, using a xenograft model where human GSCs were implanted into immunocompromised mouse flanks (FIG. 6E). While vehicle treated mice show an increase of tumor volume over time, APJ antagonist MM54 intraperitoneal injections restrain tumor growth and expansion. Although the exact mechanism by which the APJ inhibitor quells tumor formation (i.e. anti-angiogenic and/or anti-tumorigenic action) is not deciphered, these results suggested that APJ signaling is required for GSC tumor-initiating properties.

MM54 alleviated Apelin and endothelial-governed effects on the mTOR activation in GSCs (FIG. 9a). MM54 also reduced Apelin-mediated STAT3 activation in HEK-293T that co-expressed APJ and Gp130 (FIG. 9b). In addition, MM54 challenge impaired endothelial Apelin-dependent GSC self-renewal and survival (FIG. 9c). To further investigate its anti-tumour potential, we administrated the APJ inhibitor bi-weekly, intraperitoneally to subcutaneously GSC-implanted mice. In vivo, MM54 treatment strongly hindered tumour growth and decreased GSC number, as scored with Nestin, and overall cell proliferation and viability in residual tumours (FIG. 9e). This was accompanied by a reduction in tumour vascularisation (FIG. 9e).

To gain further insights into the therapeutic potential of MM54 compound, mice intracranially implanted with GSCs were treated with intraperitonal administration thrice a week. Strikingly, MM54 treatment was sufficient to both significantly abolish neurological symptoms and rescue loss weight associated with tumour progression (FIG. 15a-b). The overall survival of tumour-bearing mice was dramatically increased upon MM54 administration and tumour size was reduced (FIG. 15 c,d). Importantly, it was observed that the MM54 treatment does not exert any obvious toxic effects (cf. FIG. 16).

Thus, these data suggest that an APJ antagonist could be a suitable drug target to interfere with GBM progression.

In summary, here is documented the role of Apelin as an essential stem cell niche factor for gliomagenesis, which might be fuelled by the surrounding vascular endothelium. Our results unveil that GSCs are addicted to endothelial Apelin and identify the Apelin/APJ/Gp130 nexus as a druggable target in glioblastoma. Given the concerns about current chemotherapy regimen, including resistance and adverse effects of the anti-angiogenic antibody, bevacizumab, and the alkylating agent, temolozomide, targeting Apelin opens up new opportunities for future therapeutic uses in the treatment of these aggressive tumours.

Screening Assay of the Invention

The inventors highlighted an APJ-GP130 functional interplay by three different means.

Apelin, APJ and GP130 are required for STAT3 signaling in HEK-293T cells (Luciferase STAT3 reporter assay). This activation is blocked using anti-GP130 antibodies or a pharmacological antagonist of APJ.

GP130 is required for the Apelin-dependent APJ (G-Protein Coupled Receptor) activation in HEK-293T cells (BRET assay).

GP130 is required for Apelin binding to APJ but does not affect Apelin affinity for total APJ in GSCs (radioactive binding assay using GP130-siRNA and anti-GP130 antibodies).

This interplay does not occur in non-cancerous stem cells, as APJ is not expressed in human fetal neural stem cells, mouse embryonic stem cells, and human hematopoietic adult stem cells (FIG. 3d-e).

As mentioned previously, it would be interesting to inhibit Apelin/APJ/GP130 signaling axis to interfere with the integrity of the GSC tumor population, and, therefore, with glioblastoma progression.

The inventors set up experimental conditions for identifying Apelin/APJ/GP130 pathway inhibitor(s) in high-through-put screening. This screening advantageously requires the two following independent steps.

1. A primary screen based on STAT3 pathway inhibitory activity: STAT3 reporter

In white 96-well plates, HEK-293T cells which do not expressed APJ and GP130 were first transfected with APJ and GP130 cDNA, together with the firefly luciferase constructs downstream of STAT3 promoter and Renilla luciferase control plasmid. These cells were then treated with Apelin 24 hours later. Molecule candidates were added, and the STAT3-dependent luciferase signal was measured.

Importantly, STAT3 pathway activation was specific of Apelin/APJ/GP130 pathway and integrated upstream mTor signal. Consequently, in this first step, the firefly luciferase signal was observed only in the presence of a functional interplay between Apelin, APJ and GP130.

2. Secondary screen based on APJ G-Protein Coupled Receptor activation: BRET reporter assay In white 96-well plates, HEK-293T cells were transfected with mock, APJ and/or GP130 cDNA, together with the RLuc-beta-arrestin2-YFP plasmid (Charest P G et al, EMBO, 2005). These cells were then treated with Apelin 24 hours later. Molecule candidates were added, and the BRET-signal was measured. It was shown that the BRET signal was significantly increased and thus APJ was activated only in presence of a functional interplay between Apelin, APJ and GP130.

TABLE 1

Peptidome and proteome analysis from hCMEC/D3 secretome MS/MS analysis was performed on hCMEC/D3 secretome and compared to the HEK-293T one. Shared hits were removed from the list. The MS score and number of hits are indicated for each of the 22 identified proteins.

| Family | Name | SwissProt ID | Score | Hits |
|---|---|---|---|---|
| Secreted Growth Factors | ADM | P35318 | 679 | 13 |
| | Apelin | Q9ULZ1 | 359 | 8 |
| | CTGF | P29279 | 58 | 2 |
| | Follistatin-like 1 | Q12841 | 55 | 1 |
| | Pentraxin related protein 3 | P26022 | 246 | 6 |
| | IGF-BP7 | Q16270 | 86 | 2 |
| | MIF | P14174 | 50 | 1 |
| | TGFb2 | P61812 | 46 | 1 |
| | Galectin1 | P09382 | 49 | 1 |
| Extracellular Matrix | Galectin3 binding protein | Q08380 | 399 | 6 |
| | Fibronectin | P02751 | 543 | 12 |
| | Thrombospondin 1 | P07996 | 615 | 14 |
| | Fibulin3 | Q12805 | 181 | 4 |
| | HSPG2 | P98160 | 91 | 3 |
| | Laminin 5 | O15230 | 73 | 2 |
| | Edil3 | O43854 | 47 | 1 |
| Proteases | Serglycin | P10124 | 72 | 3 |
| | Serine protease 23 | O95084 | 62 | 2 |
| | Pai 1 | P05121 | 391 | 8 |
| | Cystatin C | P01034 | 118 | 2 |
| | MMP 1 | P03956 | 56 | 1 |
| | Cathepsin B | P07688 | 36 | 1 |

BIBLIOGRAPHIC REFERENCES

Singh et al, 2004 Identification of human brain tumour initiating cells. Nature 432, 396-401

Bao et al, 2006 Glioma stem cells promote radioresistance by preferential activation of the DNA damage response. Nature 444, 756-60

Piccirillo et al, 2006 Bone morphogenetic proteins inhibit the tumorigenic potential of human brain tumour-initiating cells. Nature 444, 761-5

Fisher et al, 2007 Epidemiology of brain tumors. Neurol Clin 25, 867-90

Rayalam et al, 2011 Emerging role of apelin as a therapeutic target in cancer: a patent review. Recent Pat Anticancer Drug Discov 6, 367-72

Pitkin et al, 2010 The apelin receptor APJ: journey from an orphan to a multifaceted regulator of homeostasis. The Journal of endocrinology 219, R13-35

Masri et al, 2004 Apelin (65-77) activates p70 S6 kinase and is mitogenic for umbilical endothelial cells FASEB J 18, 1909-11

Kidoya et al, 2012 The apelin/APJ system induces maturation of the tumor vasculature and improves the efficiency of immune therapy Oncogene 31, 3254-64

Lee et al, 2000 Characterization of apelin, the ligand for the APJ receptor. J Neurochem 74, 34-41

Macaluso et al, 2011 Discovery of a competitive apelin receptor (APJ) antagonist. ChemMedChem 6, 1017-23

Macaluso et al, 2010 Exploring the 'RPRL' motif of apelin-13 through molecular simulation and biological evaluation of cyclic peptide analogues. ChemMedChem 2, 1247-53

Galan-Moya et al, 2011 Secreted factors from brain endothelial cells maintain glioblastoma stem-like cell expansion through the mTOR pathway. EMBO Rep 12, 470-476

Weksler et al, 2005 Blood-brain barrier-specific properties of a human adult brain endothelial cell line. FASEB J. 19, 1872-1874

Chun et al, 2008 Apelin signaling antagonizes Ang II effects in mouse models of atherosclerosis. J Clin Invest 118, 3343-54

Galan et al, 2011b Feeding the hungry enemy: an endothelial recipe for glioma stem cells. Cell Cycle 10, 2403-4

Yan et al, 2013 The evolving landscape of glioblastoma stem cells. Curr Opin Neurol 26, 701-7

Verhaak et al, 2010 Integrated genomic analysis identifies clinically relevant subtypes of glioblastoma characterized by abnormalities in PDGFRA, IDH1, EGFR, and NF1. Cancer Cell 17, 98-110

Charest P G et al, E Monitoring agonist-promoted conformational changes of beta-arrestin in living cells by intramolecular BRET. EMBO Rep 6, 334-340

Chautard et al, 2010 Akt signaling pathway: a target for radiosensitizing human malignant glioma. Neuro Oncol 12, 434-43

Kim et al, 2013 Phosphorylation of EZH2 activates STAT3 signaling via STAT3 methylation and promotes tumorigenicity of glioblastoma stem-like cells. Cancer Cell 23, 839-52

Nakauchi et al, 2001 Quantitative assessment of the stem cell self-renewal capacity. Ann NY Acad Sci 938, 18-24

Al-Hajj et al, 2003 Prospective identification of tumorigenic breast cancer cells. Proc Natl Acad Sci USA 100, 3983-8

Dahlrot et al, 2013 What is the clinical value of cancer stem cell markers in gliomas? Int J Clin Exp Pathol 6, 334-48

Shenoy et al, 2011 Visualizing G protein-coupled receptor signalsomes using confocal immunofluorescence microscopy. Methods Mol Biol 756, 333-42

Patru et al, 2010, CD133, CD15/SSEA-1, CD34 or side populations do not resume tumor-initiating properties of long-term cultured cancer stem cells from human malignant glio-neuronal tumors. BMC Cancer 10, 66

The invention claimed is:

1. A method for identifying compounds capable of inhibiting Cancer Stem Cells properties, wherein said properties are potency, self-renewal, and survival, said method comprising the steps:
   a) contacting cells that have been transfected with exogenous nucleotide vectors expressing the co-receptors APJ and GP130 or are Cancer Stem Cells expressing the co-receptors APJ and GP130 with the Apelin polypeptide and a candidate compound,
   b) detecting the activation level of an Apelin-dependent signaling pathway in the cells contacted in step a), and
   c) detecting the activation level of an Apelin-dependent signaling pathway in cells that have been transfected with exogenous nucleotide vectors expressing the co-receptors APJ and GP130 or are Cancer Stem Cells expressing the co-receptors APJ and GP130 contacted only with the Apelin polypeptide;
   wherein a candidate compound that impairs the activation level of an Apelin-dependent signaling pathway in cells from step a) as compared with cells from step c) is capable of inhibiting the potency and/or the self-renewal and/or the survival of Cancer Stem Cells.

2. The method of claim 1, wherein detecting step b) comprises the detection and/or measurement of the activation level of an APJ-dependent signaling pathway.

3. The method of claim 2, wherein activation of the APJ receptor is assessed by studying beta-arrestin2 recruitment to APJ.

4. The method of claim 2, wherein said APJ-dependent signaling pathway is the Akt/mTOR signaling pathway.

5. The method of claim 1, wherein detecting step b) comprises the detection and/or measurement of the activation level of a GP130-dependent signaling pathway.

6. The method of claim 1, wherein said detecting step b) comprises the detection of the interaction between the co-receptors APJ and GP130.

7. The method of claim 1, wherein the detecting step b) comprises the steps of:
   b1) measuring the Apelin-dependent activation level of a GP130-dependent signaling pathway, and
   b2) measuring the Apelin-dependent activation level of an APJ-dependent signaling pathway in said cells.

8. The method of claim 7, wherein the detecting step b) comprises the steps of:
   b1) measuring the Apelin-dependent activation level of the STAT3 signaling pathway in said cells, and
   b2) measuring the Apelin-dependent beta-arrestin2 recruitment to APJ in said cells.

9. The method of claim 3, wherein activation of the APJ receptor is assessed by studying beta-arrestin2 recruitment to APJ by Bioluminescence Resonance Energy Transfer.

10. A method for identifying compounds capable of inhibiting Cancer Stem Cells properties, wherein said properties are potency, self-renewal, and survival, said method comprising the steps:
   a) contacting cells that have been transfected with exogenous nucleotide vectors expressing the co-receptors APJ and GP130 or are Cancer Stem Cells expressing the co-receptors APJ and GP130, with the Apelin polypeptide and a candidate compound,
b) detecting the activation level of an Apelin-dependent signaling pathway in the cells contacted in step a),
c) detecting the activation level of an Apelin-dependent signaling pathway in cells that have been transfected with exogenous nucleotide vectors expressing the co-receptors APJ and GP130 or are Cancer Stem Cells expressing the co-receptors APJ and GP130, contacted only with the Apelin polypeptide
d) selecting a candidate compound wherein the activation level of an Apelin-dependent signaling pathway is impaired in cells from step a) as compared with cells from step c), and
e) detecting if said selected candidate compound inhibits the potency and/or self-renewal and/or the survival of Cancer Stem Cells.

* * * * *

SEQUENCE LISTING

```
<160> NUMBER OF SEQ ID NOS: 21

<210> SEQ ID NO 1
<211> LENGTH: 77
<212> TYPE: PRT
<213> ORGANISM: homo sapiens
<220> FEATURE:
<221> NAME/KEY: MISC_FEATURE
<223> OTHER INFORMATION: NP_059109 - human apelin proprotein

<400> SEQUENCE: 1

Met Asn Leu Arg Leu Cys Val Gln Ala Leu Leu Leu Leu Trp Leu Ser
1               5                   10                  15
```

Leu Thr Ala Val Cys Gly Gly Ser Leu Met Pro Leu Pro Asp Gly Asn
            20                  25                  30

Gly Leu Glu Asp Gly Asn Val Arg His Leu Val Gln Pro Arg Gly Ser
            35                  40                  45

Arg Asn Gly Pro Gly Pro Trp Gln Gly Gly Arg Arg Lys Phe Arg Arg
    50                  55                  60

Gln Arg Pro Arg Leu Ser His Lys Gly Pro Met Pro Phe
65                  70                  75

<210> SEQ ID NO 2
<211> LENGTH: 13
<212> TYPE: PRT
<213> ORGANISM: homo sapiens
<220> FEATURE:
<221> NAME/KEY: MISC_FEATURE
<223> OTHER INFORMATION: Apelin 13 aa - homo sapiens

<400> SEQUENCE: 2

Gln Arg Pro Arg Leu Ser His Lys Gly Pro Met Pro Phe
1               5                   10

<210> SEQ ID NO 3
<211> LENGTH: 36
<212> TYPE: PRT
<213> ORGANISM: homo sapiens
<220> FEATURE:
<221> NAME/KEY: MISC_FEATURE
<223> OTHER INFORMATION: Apelin 36 aa - homo sapiens

<400> SEQUENCE: 3

Leu Val Gln Pro Arg Gly Ser Arg Asn Gly Pro Gly Pro Trp Gln Gly
1               5                   10                  15

Gly Arg Arg Lys Phe Arg Arg Gln Arg Pro Arg Leu Ser His Lys Gly
            20                  25                  30

Pro Met Pro Phe
        35

<210> SEQ ID NO 4
<211> LENGTH: 380
<212> TYPE: PRT
<213> ORGANISM: homo sapiens
<220> FEATURE:
<221> NAME/KEY: MISC_FEATURE
<223> OTHER INFORMATION: NP_005152 - human. APJ receptor

<400> SEQUENCE: 4

Met Glu Glu Gly Gly Asp Phe Asp Asn Tyr Tyr Gly Ala Asp Asn Gln
1               5                   10                  15

Ser Glu Cys Glu Tyr Thr Asp Trp Lys Ser Ser Gly Ala Leu Ile Pro
            20                  25                  30

Ala Ile Tyr Met Leu Val Phe Leu Leu Gly Thr Thr Gly Asn Gly Leu
        35                  40                  45

Val Leu Trp Thr Val Phe Arg Ser Ser Arg Glu Lys Arg Arg Ser Ala
    50                  55                  60

Asp Ile Phe Ile Ala Ser Leu Ala Val Ala Asp Leu Thr Phe Val Val
65                  70                  75                  80

Thr Leu Pro Leu Trp Ala Thr Tyr Thr Tyr Arg Asp Tyr Asp Trp Pro
                85                  90                  95

Phe Gly Thr Phe Phe Cys Lys Leu Ser Ser Tyr Leu Ile Phe Val Asn
            100                 105                 110

Met Tyr Ala Ser Val Phe Cys Leu Thr Gly Leu Ser Phe Asp Arg Tyr
            115                 120                 125

Leu Ala Ile Val Arg Pro Val Ala Asn Ala Arg Leu Arg Leu Arg Val
        130                 135                 140

Ser Gly Ala Val Ala Thr Ala Val Leu Trp Val Leu Ala Ala Leu Leu
145                 150                 155                 160

Ala Met Pro Val Met Val Leu Arg Thr Thr Gly Asp Leu Glu Asn Thr
                165                 170                 175

Thr Lys Val Gln Cys Tyr Met Asp Tyr Ser Met Val Ala Thr Val Ser
            180                 185                 190

Ser Glu Trp Ala Trp Glu Val Gly Leu Gly Val Ser Ser Thr Thr Val
        195                 200                 205

Gly Phe Val Val Pro Phe Thr Ile Met Leu Thr Cys Tyr Phe Phe Ile
210                 215                 220

Ala Gln Thr Ile Ala Gly His Phe Arg Lys Glu Arg Ile Glu Gly Leu
225                 230                 235                 240

Arg Lys Arg Arg Arg Leu Leu Ser Ile Ile Val Val Leu Val Val Thr
                245                 250                 255

Phe Ala Leu Cys Trp Met Pro Tyr His Leu Val Lys Thr Leu Tyr Met
            260                 265                 270

Leu Gly Ser Leu Leu His Trp Pro Cys Asp Phe Asp Leu Phe Leu Met
        275                 280                 285

Asn Ile Phe Pro Tyr Cys Thr Cys Ile Ser Tyr Val Asn Ser Cys Leu
290                 295                 300

Asn Pro Phe Leu Tyr Ala Phe Phe Asp Pro Arg Phe Arg Gln Ala Cys
305                 310                 315                 320

Thr Ser Met Leu Cys Cys Gly Gln Ser Arg Cys Ala Gly Thr Ser His
                325                 330                 335

Ser Ser Ser Gly Glu Lys Ser Ala Ser Tyr Ser Ser Gly His Ser Gln
            340                 345                 350

Gly Pro Gly Pro Asn Met Gly Lys Gly Gly Glu Gln Met His Glu Lys
        355                 360                 365

Ser Ile Pro Tyr Ser Gln Glu Thr Leu Val Val Asp
370                 375                 380

<210> SEQ ID NO 5
<211> LENGTH: 3905
<212> TYPE: DNA
<213> ORGANISM: homo sapiens
<220> FEATURE:
<221> NAME/KEY: misc_feature
<223> OTHER INFORMATION: NM_005161 - human APJ receptor mRNA

<400> SEQUENCE: 5
ggaaagccga cttgcaaaac cacagataat gttcagccca gcacagtagg ggtcaatttg      60
gtccacttgc tcagtgacaa aaagaaaaaa aaagtgggct gtcactaaag attttgactc     120
acaagagagg ggctggtctg gaggtgggag gagggagtga cgagtcaagg aggagacagg     180
gacgcaggag ggtgcaagga agtgtcttaa ctgagacggg ggtaaggcaa gagagggtgg     240
aggaaattct gcaggagaca ggcttcctcc agggtctgga gaacccagag gcagctcctc     300
ctgagtgctg ggaaggactc tgggcatctt cagcccttct tactctctga ggctcaagcc     360
agaaattcag gctgcttgca gagtgggtga cagagccacg gagctggtgt ccctgggacc     420
ctctgcccgt cttctctcca ctccccagca tggaggaagg tggtgatttt gacaactact     480 atgggggcaga caaccagtct gagtgtgagt acacagactg gaaatcctcg ggggccctca     540

```
tccctgccat ctacatgttg gtcttcctcc tgggcaccac gggcaacggt ctggtgctct      600
ggaccgtgtt tcggagcagc cgggagaaga ggcgctcagc tgatatcttc attgctagcc      660
tggcggtggc tgacctgacc ttcgtggtga cgctgcccct gtgggctacc tacacgtacc      720
gggactatga ctggcccttt gggaccttct tctgcaagct cagcagctac ctcatcttcg      780
tcaacatgta cgccagcgtc ttctgcctca ccggcctcag cttcgaccgc tacctggcca      840
tcgtgaggcc agtggccaat gctcggctga ggctgcgggt cagcggggcc gtggccacgg      900
cagttctttg ggtgctggcc gccctcctgg ccatgcctgt catggtgtta cgcaccaccg      960
gggacttgga gaacaccact aaggtgcagt gctacatgga ctactccatg gtggccactg     1020
tgagctcaga gtgggcctgg gaggtgggcc ttggggtctc gtccaccacc gtgggctttg     1080
tggtgccctt caccatcatg ctgacctgtt acttcttcat cgcccaaacc atcgctggcc     1140
acttccgcaa ggaacgcatc gagggcctgc ggaagcggcg ccggctgctc agcatcatcg     1200
tggtgctggt ggtgaccttt gccctgtgct ggatgcccta ccacctggtg aagacgctgt     1260
acatgctggg cagcctgctg cactggccct gtgactttga cctcttcctc atgaacatct     1320 tccctactg cacctgcatc agctacgtca acagctgcct caacccctc ctctatgcct     1380 ttttcgaccc ccgcttccgc caggcctgca cctccatgct ctgctgtggc cagagcaggt     1440
gcgcaggcac ctcccacagc agcagtgggg agaagtcagc cagctactct tcggggcaca     1500
gccaggggcc cggccccaac atgggcaagg gtggagaaca gatgcacgag aaatccatcc     1560
cctacagcca ggagacccttt gtggttgact agggctggga gcagagagaa gcctggcgcc     1620
ctcggccctc cccggccttt gcccttgctt tctgaaaatc aggtagtgtg ctactccttt     1680
gtcctatgca catccttttaa ctgtcccctg attctgcccc gccctgtcct cctctactgc     1740
tttattcttt ctcagaggtt tgtggtttag gggaaagaga ctgggctcta cagacctgac     1800
cctgcacaag ccatttaatc tcactcagcc tcagtttctc cattggtatg aaatggggga     1860
aagtcatatt gatcctaaaa tgttgaagcc tgagtctgga cgcagtaaaa gcttgtttcc     1920
ctctgctgct ttcttagatc tgcaatcgtc tttcctcccct tctttccttg tagttttttcc    1980 cccaccactc tctgcagctg ccgctcctta tccctgcctt ctggcaccaa tcccctccta     2040
cagctcgtcc ccctccctcc atccatcctt ctccctgtc tactttcttg ttctgaaggg     2100
ctactaaggg ttaaggatcc caaagcttgc agagactgac cctgtttaag ctttctatcc     2160
tgttttctga gtgtgaggca gggaatgggc tggggccggg ggtgggctgt gtgtcagcag     2220
ataattagtg ctccagccct tagatctggg agctccagag cttgccctaa aattggatca     2280
cttccctgtc attttgggca ttggggctag tgtgattcct gcagttcccc catggcacca     2340
tgacactgac tagatatgct ttctccaaat tgtccgcaga ccctttcatc cttcctctat     2400
tttctatgag aattggaagg cagcagggct gatgaatgga tgtactcctt ggtttcatta     2460
tgtgagtggg gagttgggaa gggcaactag agagagagga tggaggggtg tctgcatta     2520 gtccagacac tgcttggctc gctccccgag tcctcctgtt tctgacttcc tgcataactg     2580
tgagctgaag ggtttcctca tctcccccatc ttaccccatc atactgattt ctttcttggg     2640
cactggtgct acttggtgcc aagaatcatg ttgtttggga tggagatgcc tgcctcttgt     2700
ctgtgtgtgt tgtacttata tgtctatatg gatgagcctg gcatgaacag cagtgtgcct     2760
gggtcatttg gacaaatctc ctcccacccc ccaatccact gcaactctgc tgttcacaca     2820
ttacccttgg caggggtgg tgggggggcag ggacacactg aggcaatgaa aaatgtagaa     2880
```

-continued

```
taaaaatgag tccaccccct actggatttg ggggctccaa cggctggtcc gtgctttagg    2940
agcgaagtta atgtttgcac caggcttcct gtagggagat ccctcccaa agcagctggc     3000 gccaaggctt gggggcgtcc tactgagctg ggttcctgct ccttcttggg ctccatgaag    3060
gaagtaagag gctagttgag agcctcccctt ggccccttc cggtgcctcc ccgcctggct    3120
tcaaatttat gagcattgcc ctcatcgtcc tttcttgttc cagggtcagt ggccctcttc    3180
ctaaggaggc ctcctgcttg ccatgggcca aaaggcacgg ggtgggtttt ttctctccct   3240
accctcagga ttggacctct tggcttctgc tggattgggg atctgggaat agggactgga   3300
gcaagtgtgc agatagcatg atgtctacac tgccagagag accgtgagga tgaaattaat   3360
agtggggcct ttgtgagcta gaggctggga gtgtctattc cgggttttgt tcttggagga   3420
ctatgaaagt gaaggacaag acatgagcga tggagataag aaaagcccag cttgatgtga   3480
atggacatct tgaccctccc tggaatgacg ccagctctgg gggcagaggg aggaggagag   3540
gggaaggggc tcctcacagc ctagtctccc catcttaaga tagcatcttt cacagagtca   3600
cctcctctgc ccagagctgt cctcaaagca tccagtgaac actggaagag gcttctagaa   3660
gggaagaaat tgtccctctg aggccgccgt gggtgacctg cagagacttc ctgcctggaa   3720
ctcatctgtg aactgggaca gaagcagagg aggctgcctg ctgtgatacc cccttacctc   3780
ccccagtgcc ttcttcagaa tatctgcact gtcttctgat cctgttagtc actgtggttc   3840
atcaaataaa actgtttgtg caactgttgt gtccaaaaaa aaaaaaaaaa aaaaaaaaa    3900 aaaaa                                                               3905
```

<210> SEQ ID NO 6
<211> LENGTH: 918
<212> TYPE: PRT
<213> ORGANISM: homo sapiens
<220> FEATURE:
<221> NAME/KEY: MISC_FEATURE
<223> OTHER INFORMATION: P40189.2 - human GP130 protein

<400> SEQUENCE: 6

```
Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
                20                  25                  30

Pro Glu Ser Pro Val Val Gln Leu His Ser Asn Phe Thr Ala Val Cys
            35                  40                  45

Val Leu Lys Glu Lys Cys Met Asp Tyr Phe His Val Asn Ala Asn Tyr
        50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175
```

```
Asp Thr Pro Thr Ser Cys Thr Val Asp Tyr Ser Thr Val Tyr Phe Val
                180                 185                 190

Asn Ile Glu Val Trp Val Glu Ala Glu Asn Ala Leu Gly Lys Val Thr
            195                 200                 205

Ser Asp His Ile Asn Phe Asp Pro Val Tyr Lys Val Lys Pro Asn Pro
        210                 215                 220

Pro His Asn Leu Ser Val Ile Asn Ser Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
            340                 345                 350

Thr Leu Pro Pro Phe Glu Ala Asn Gly Lys Ile Leu Asp Tyr Glu Val
        355                 360                 365

Thr Leu Thr Arg Trp Lys Ser His Leu Gln Asn Tyr Thr Val Asn Ala
    370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
            420                 425                 430

Phe Pro Lys Asp Asn Met Leu Trp Val Glu Trp Thr Thr Pro Arg Glu
        435                 440                 445

Ser Val Lys Lys Tyr Ile Leu Glu Trp Cys Val Leu Ser Asp Lys Ala
    450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
            500                 505                 510

Tyr Leu Lys Gln Ala Pro Pro Ser Lys Gly Pro Thr Val Arg Thr Lys
        515                 520                 525

Lys Val Gly Lys Asn Glu Ala Val Leu Glu Trp Asp Gln Leu Pro Val
    530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
            580                 585                 590
```

| | | | | | | | | | | | | |
|---|---|---|---|---|---|---|---|---|---|---|---|---|
|Ala|Ala|Tyr|Thr|Asp|Glu|Gly|Gly|Lys|Asp|Gly|Pro|Glu|Phe|Thr|Phe|
| | | |595| | | |600| | | |605| | | |

Ala Ala Tyr Thr Asp Glu Gly Gly Lys Asp Gly Pro Glu Phe Thr Phe
            595                 600             605

Thr Thr Pro Lys Phe Ala Gln Gly Glu Ile Glu Ala Ile Val Val Pro
    610                 615                 620

Val Cys Leu Ala Phe Leu Leu Thr Thr Leu Leu Gly Val Leu Phe Cys
625                 630                 635                 640

Phe Asn Lys Arg Asp Leu Ile Lys Lys His Ile Trp Pro Asn Val Pro
                645                 650                 655

Asp Pro Ser Lys Ser His Ile Ala Gln Trp Ser Pro His Thr Pro Pro
            660                 665                 670

Arg His Asn Phe Asn Ser Lys Asp Gln Met Tyr Ser Asp Gly Asn Phe
        675                 680                 685

Thr Asp Val Ser Val Val Glu Ile Glu Ala Asn Asp Lys Lys Pro Phe
    690                 695                 700

Pro Glu Asp Leu Lys Ser Leu Asp Leu Phe Lys Lys Glu Lys Ile Asn
705                 710                 715                 720

Thr Glu Gly His Ser Ser Gly Ile Gly Gly Ser Ser Cys Met Ser Ser
                725                 730                 735

Ser Arg Pro Ser Ile Ser Ser Ser Asp Glu Asn Glu Ser Ser Gln Asn
            740                 745                 750

Thr Ser Ser Thr Val Gln Tyr Ser Thr Val Val His Ser Gly Tyr Arg
        755                 760                 765

His Gln Val Pro Ser Val Gln Val Phe Ser Arg Ser Glu Ser Thr Gln
    770                 775                 780

Pro Leu Leu Asp Ser Glu Glu Arg Pro Glu Asp Leu Gln Leu Val Asp
785                 790                 795                 800

His Val Asp Gly Gly Asp Gly Ile Leu Pro Arg Gln Gln Tyr Phe Lys
                805                 810                 815

Gln Asn Cys Ser Gln His Glu Ser Ser Pro Asp Ile Ser His Phe Glu
            820                 825                 830

Arg Ser Lys Gln Val Ser Ser Val Asn Glu Glu Asp Phe Val Arg Leu
        835                 840                 845

Lys Gln Gln Ile Ser Asp His Ile Ser Gln Ser Cys Gly Ser Gly Gln
    850                 855                 860

Met Lys Met Phe Gln Glu Val Ser Ala Ala Asp Ala Phe Gly Pro Gly
865                 870                 875                 880

Thr Glu Gly Gln Val Glu Arg Phe Glu Thr Val Gly Met Glu Ala Ala
                885                 890                 895

Thr Asp Glu Gly Met Pro Lys Ser Tyr Leu Pro Gln Thr Val Arg Gln
            900                 905                 910

Gly Gly Tyr Met Pro Gln
        915

<210> SEQ ID NO 7
<211> LENGTH: 5928
<212> TYPE: DNA
<213> ORGANISM: homo sapiens
<220> FEATURE:
<221> NAME/KEY: misc_feature
<223> OTHER INFORMATION: NM_000565.3 - human GP130 mRNA

<400> SEQUENCE: 7
ggcggtcccc tgttctcccc gctcaggtgc ggcgctgtgg caggaagcca ccccctcggt      60
cggccggtgc gcggggctgt tgcgccatcc gctccggctt tcgtaaccgc acctgggac     120 ggcccagaga cgctccagcg cgagttcctc aaatgttttc ctgcgttgcc aggaccgtcc    180

```
gccgctctga gtcatgtgcg agtgggaagt cgcactgaca ctgagccggg ccagagggag      240
aggagccgag cgcggcgcgg ggccgaggga ctcgcagtgt gtgtagagag ccgggctcct      300
gcggatgggg gctgccccg gggcctgagc ccgcctgccc gccaccgcc ccgccccgcc        360 cctgccaccc ctgccgcccg gttcccatta gcctgtccgc ctctgcggga ccatggagtg      420
gtagccgagg aggaagcatg ctggccgtcg gctgcgcgct gctggctgcc ctgctggccg      480
cgccgggagc ggcgctggcc ccaaggcgct gccctgcgca ggaggtggcg agaggcgtgc      540
tgaccagtct gccaggagac agcgtgactc tgacctgccc gggggtagag ccggaagaca      600
atgccactgt tcactgggtg ctcaggaagc cggctgcagg ctcccacccc agcagatggg      660
ctggcatggg aaggaggctg ctgctgaggt cggtgcagct ccacgactct ggaaactatt      720
catgctaccg gccggccgc ccagctggga ctgtgcactt gctggtggat gttccccccg       780
aggagcccca gctctcctgc ttccggaaga gcccctcag caatgttgtt tgtgagtggg       840
gtcctcggag cacccatcc ctgacgacaa aggctgtgct cttggtgagg aagtttcaga       900
acagtccggc cgaagacttc caggagccgt gccagtattc caggagtcc cagaagttct       960 cctgccagtt agcagtcccg gagggagaca gctctttcta catagtgtcc atgtgcgtcg     1020
ccagtagtgt cgggagcaag ttcagcaaaa ctcaaacctt tcagggttgt ggaatcttgc     1080
agcctgatcc gcctgccaac atcacagtca ctgccgtggc cagaaacccc cgctggctca     1140
gtgtcacctg gcaagacccc cactcctgga actcatcttt ctacagacta cggtttgagc     1200
tcagatatcg ggctgaacgg tcaaagacat tcacaacatg gatggtcaag gacctccagc     1260
atcactgtgt catccacgac gcctggagcg gcctgaggca cgtggtgcag cttcgtgccc     1320
aggaggagtt cgggcaaggc gagtggagcg agtggagccc ggaggccatg ggcacgcctt     1380
ggacagaatc caggagtcct ccagctgaga acgaggtgtc cacccccatg caggcactta     1440
ctactaataa agacgatgat aatattctct tcagagattc tgcaaatgcg acaagcctcc     1500
cagtgcaaga ttcttcttca gtaccactgc ccacattcct ggttgctgga gggagcctgg     1560
ccttcggaac gctcctctgc attgccattg ttctgagggt caagaagacg tggaagctgc     1620
gggctctgaa ggaaggcaag acaagcatgc atccgccgta ctctttgggg cagctggtcc     1680
cggagaggcc tcgacccacc ccagtgcttg ttcctctcat ctccccaccg gtgtccccca     1740
gcagcctggg gtctgacaat acctcgagcc acaaccgacc agatgccagg acccacggga     1800
gcccttatga catcagcaat acagactact tcttccccag atagctggct gggtggcacc     1860
agcagcctgg accctgtgga tgataaaaca caaacgggc cagcaaaaga tgcttctcac     1920
tgccatgcca gcttatctca ggggtgtgcg gcctttggct tcacggaaga gccttgcgga     1980
aggttctacg ccaggggaaa atcagcctgc tccagctgtt cagctggttg aggtttcaaa     2040 cctcccttt caaatgccca gcttaaaggg gctagagtga acttgggcca ctgtgaagag     2100
aaccatatca agactctttg gacactcaca cggacactca aaagctgggc aggttggtgg     2160
gggcctcggt gtggagaagc ggctggcagc ccaccctca acacctctgc acaagctgca     2220
ccctcaggca ggtgggatgg attccagcc aaagcctcct ccagccgcca tgctcctggc     2280
ccactgcatc gtttcatctt ccaactcaaa ctcttaaaac ccagtgcct tagcaaattc     2340 tgttttcta ggcctgggga cggcttttac ttaaaccgcc aaggctgggg gaagaagctc     2400
tctcctccct ttcttcccta cagttgaaaa acagctgagg gtgagtgggt gaataataca     2460
gtatctcagg gcctggtcgt tttcaacaga attataatta gttcctcatt agcattttgc     2520
```

```
taaatgtgaa tgatgatcct aggcatttgc tgaatacaga ggcaactgca ttggctttgg    2580
gttgcaggac ctcaggtgag aagcagagga aggagaggag aggggcacag ggtctctacc    2640
atcccctgta gagtgggagc tgagtggggg atcacagcct ctgaaaacca atgttctctc    2700
ttctccacct cccacaaagg agagctagca gcagggaggg cttctgccat ttctgagatc    2760
aaaacggttt tactgcagct ttgtttgttg tcagctgaac ctgggtaact agggaagata    2820
atattaagga agacaatgtg aaaagaaaaa tgagcctggc aagaatgtgt ttaaacttgg    2880
tttttaaaaa actgctgact gttttctctt gagagggtgg aatatccaat attcgctgtg    2940
tcagcataga agtaacttac ttaggtgtgg gggaagcacc ataactttgt ttagcccaaa    3000
accaagtcaa gtgaaaaagg aggaagagaa aaaatatttt cctgccaggc atggtggccc    3060
acgcacttcg ggaggtcgag gcaggaggat cacttgagtc cagaagtttg agatcagcct    3120
gggcaatgtg ataaaacccc atctctacaa aaagcataaa aattagccaa gtgtggtaga    3180
gtgtgcctga gtcccagat acttgggggg ctgaggtggg aggatctctt gagcctggga    3240
ggtcaaggct gcagtgagcc gagattgcac cactgcactc cagcctgggt gacagagcaa    3300
gtgagaccct gtctcaaaaa aagaaaaaga aaaagaaaaa atattttccc tattagagaa    3360
gagattgtgg tttcattctg tattttgttt ttgtcttaaa aagtggaaaa atagcctgcc    3420
tcttctctac tctagggaaa aaccagcgtg tgactactcc cccaggtggt tatggagagg    3480
gtgtccggtc cctgtcccag tgccgagaag gaagcctccc acgactgccc ggcagggtcc    3540
tagaaattcc ccaccctgaa agccctgagc tttctgctat caaagaggtt ttaaaaaaat    3600
cccatttaaa aaaaatccct tacctcggtg ccttcctctt tttatttagt tccttgagtt    3660
gattcagctc tgcaagaatt gaagcaggac taaatgtcta gttgtaacac catgattaac    3720
cacttcagct gactttttctg tccgagcttt gaaaattcag tggtgttagt ggttacccag    3780
ttagctctca agttatcagg gtattccaga gtggggatat gatttaaatc agccgtgtaa    3840
ccatggaccc aatatttacc agaccacaaa acttttctaa tactctaccc tcttagaaaa    3900
accaccacca tcaccagaca ggtgcgaaag gatgaaagtg accatgtttt gtttacggtt    3960
ttccaggttt aagctgttac tgtcttcagt aagccgtgat tttcattgct gggcttgtct    4020
gtagatttta gaccctattg ctgcttgagg caactcatct taggttggca aaaaggcagg    4080
atggccgggc gcgtggctc acgcctgtaa tcctagcact ttgggaggcc aaggtgggag    4140
gattgcttga gctcaggagt ttgagaccaa cctgggtaac atagtgagac accatctcta    4200
ttatgaacaa taacagttaa gaaaaaaaaa ggcaggcagg cggttatggt ggttccctcc    4260
catcccacca cataaagttt ctgagacttg agaacagcaa aatgctgtta agggaaata    4320 ttaagaatga gaatctgcag taagggtgat tctgtgccca cagttcttca attctttata    4380
ccgttttacc cacatgtggt gttaccaaag ccgggcagaa ccatgctagc ggaagatgtg    4440
aaatccagat agctcattat tgccaagagc taggcagctt tgatctccaa attgttattg    4500 cttttcatttt tattgtaatg gaattgcttt gttttgtttt tttgttttg tattgaagag    4560 ggttgttttc cctttatttt tcataagcta atgtaaatga agaaaaaatg tcttctctgg    4620
gctgtaggcc tggctcagcg tacacaggta tacatcctaa gctctctatg ttctctaatc    4680
tgtggtgact gaacatgtgt ctcaatgcac ggggcatttc tacctgtgtt tctgcagcac    4740
ccccactgcc ttgagtcccc agcagtgctg ttatttgcct aacacctgta gccatctgcc    4800
acgcagccag acgtgaaacg ctgagacaga gaccatttag gttaaatacg acagcttatc    4860
ctgctgggtg gggaaagtaa aaaatatgct ggttcaaggc ctaaagtaaa atgatcaata    4920
```

```
atgtttgtag cattaatgaa atattttcaa gaaatgtgtc caggggtagc actggctatg    4980
ttgacgaggc ctttggtaac tcagagagct cttggccctg atggggactt gcccttacgc    5040
tttctttatc aggctctgag ttcacacgga gcctctggca cttccctgct gtcttgggag    5100
aaaggaaact ggttgccgcg gcaggttgtg aatctgttg ctggaaccag gctggaagcc    5160
cacctggtag tgaacagggc ccagtggggc aggctgggca tgttgtggtc tatgggtttg    5220
tttcctggag aatgttcagg aatgtcttcc cagctgcttt ggtgctgagc tctattatct    5280
cacagcacgt ccagaaggct aacccaggtg gggaggatgc tgacaccagc tccaggtgga    5340
gttggtggtc ttaatttgga gatgcagggg caacctgtga cccttgagg caagagccct    5400 gcacccagct gtcccgtgca gccgtgggca ggggctgcac acggaggggc aggcgggcca    5460
gttcagggtc cgtgccaggc cctcctcagt gccctgtgaa ggcctcctgt cctccgtgcg    5520
gctgggcacc agcaccaggg agtttctatg caaccttag tgattattaa ggaacactgt    5580 cagtttatg aacatatgct caaatgaaat tctactttag gaggaaagga ttggaacagc    5640
atgtcacaag gctgttaatt aacagagaga ccttattgga tggagatcac atctgttaaa    5700
tagaatacct caactctacg ttgttttctt ggagataaat aatagtttca gttttttgtt    5760
tgtttgtttt acctaattac ctgaaagcaa ataccaaagg ctgatgtctg tatatggggc    5820
aaagggtcag tatattttc agtgtttttt tttctaccag ctattttgca tttaaagtga    5880
acattgtgtt tggaataaat actcttaaaa aataaaaaaa aaaaaaaa                 5928
```

<210> SEQ ID NO 8
<211> LENGTH: 409
<212> TYPE: PRT
<213> ORGANISM: homo sapiens
<220> FEATURE:
<221> NAME/KEY: MISC_FEATURE
<223> OTHER INFORMATION: human beta-arrestin2 protein - P32121.2

<400> SEQUENCE: 8

```
Met Gly Glu Lys Pro Gly Thr Arg Val Phe Lys Lys Ser Ser Pro Asn
1               5                   10                  15

Cys Lys Leu Thr Val Tyr Leu Gly Lys Arg Asp Phe Val Asp His Leu
            20                  25                  30

Asp Lys Val Asp Pro Val Asp Gly Val Val Leu Val Asp Pro Asp Tyr
        35                  40                  45

Leu Lys Asp Arg Lys Val Phe Val Thr Leu Thr Cys Ala Phe Arg Tyr
    50                  55                  60

Gly Arg Glu Asp Leu Asp Val Leu Gly Leu Ser Phe Arg Lys Asp Leu
65                  70                  75                  80

Phe Ile Ala Thr Tyr Gln Ala Phe Pro Pro Val Pro Asn Pro Pro Arg
                85                  90                  95

Pro Pro Thr Arg Leu Gln Asp Arg Leu Leu Arg Lys Leu Gly Gln His
            100                 105                 110

Ala His Pro Phe Phe Phe Thr Ile Pro Gln Asn Leu Pro Cys Ser Val
        115                 120                 125

Thr Leu Gln Pro Gly Pro Glu Asp Thr Gly Lys Ala Cys Gly Val Asp
    130                 135                 140

Phe Glu Ile Arg Ala Phe Cys Ala Lys Ser Leu Glu Glu Lys Ser His
145                 150                 155                 160

Lys Arg Asn Ser Val Arg Leu Val Ile Arg Lys Val Gln Phe Ala Pro
                165                 170                 175
```

-continued

```
        Glu Lys Pro Gly Pro Gln Pro Ser Ala Glu Thr Thr Arg His Phe Leu
                    180                 185                 190

Met Ser Asp Arg Ser Leu His Leu Glu Ala Ser Leu Asp Lys Glu Leu
                195                 200                 205

Tyr Tyr His Gly Glu Pro Leu Asn Val Asn Val His Val Thr Asn Asn
                210                 215                 220

Ser Thr Lys Thr Val Lys Ile Lys Val Ser Val Arg Gln Tyr Ala
        225                 230                 235                 240

Asp Ile Cys Leu Phe Ser Thr Ala Gln Tyr Lys Cys Pro Val Ala Gln
                        245                 250                 255

Leu Glu Gln Asp Asp Gln Val Ser Pro Ser Ser Thr Phe Cys Lys Val
                    260                 265                 270

Tyr Thr Ile Thr Pro Leu Leu Ser Asp Asn Arg Glu Lys Arg Gly Leu
                275                 280                 285

Ala Leu Asp Gly Lys Leu Lys His Glu Asp Thr Asn Leu Ala Ser Ser
                290                 295                 300

Thr Ile Val Lys Glu Gly Ala Asn Lys Glu Val Leu Gly Ile Leu Val
        305                 310                 315                 320

Ser Tyr Arg Val Lys Val Lys Leu Val Val Ser Arg Gly Gly Asp Val
                        325                 330                 335

Ser Val Glu Leu Pro Phe Val Leu Met His Pro Lys Pro His Asp His
                    340                 345                 350

Ile Pro Leu Pro Arg Pro Gln Ser Ala Ala Pro Glu Thr Asp Val Pro
                    355                 360                 365

Val Asp Thr Asn Leu Ile Glu Phe Asp Thr Asn Tyr Ala Thr Asp Asp
                370                 375                 380

Asp Ile Val Phe Glu Asp Phe Ala Arg Leu Arg Leu Lys Gly Met Lys
        385                 390                 395                 400

Asp Asp Asp Tyr Asp Asp Gln Leu Cys
                        405

<210> SEQ ID NO 9
<211> LENGTH: 54
<212> TYPE: DNA
<213> ORGANISM: artificial
<220> FEATURE:
<223> OTHER INFORMATION: STAT3 promoter sequence

<400> SEQUENCE: 9
tgcttcccga attcccgaat tcccgaattc cgaattccc gaattcccga acgt          54

<210> SEQ ID NO 10
<211> LENGTH: 25
<212> TYPE: RNA
<213> ORGANISM: artificial
<220> FEATURE:
<223> OTHER INFORMATION: siRNA specific for APJ

<400> SEQUENCE: 10
ccaucaugcu gaccuguuac uucuu                                         25

<210> SEQ ID NO 11
<211> LENGTH: 25
<212> TYPE: RNA
<213> ORGANISM: artificial
<220> FEATURE:
<223> OTHER INFORMATION: siRNA specific for APJ

<400> SEQUENCE: 11
```

```
gacaaccagu cugaguguga guaca                                          25

<210> SEQ ID NO 12
<211> LENGTH: 25
<212> TYPE: RNA
<213> ORGANISM: artificial
<220> FEATURE:
<223> OTHER INFORMATION: siRNA specific for Apelin

<400> SEQUENCE: 12
ggugcagccc agagggucaa ggaau                                          25

<210> SEQ ID NO 13
<211> LENGTH: 25
<212> TYPE: RNA
<213> ORGANISM: artificial
<220> FEATURE:
<223> OTHER INFORMATION: siRNA specific for Apelin

<400> SEQUENCE: 13
ccucucccau aagggaccca ugccu                                          25

<210> SEQ ID NO 14
<211> LENGTH: 25
<212> TYPE: RNA
<213> ORGANISM: artificial
<220> FEATURE:
<223> OTHER INFORMATION: siRNA specific for Apelin

<400> SEQUENCE: 14
ccugaugccg cuucccgaug ggaau                                          25

<210> SEQ ID NO 15
<211> LENGTH: 21
<212> TYPE: DNA
<213> ORGANISM: artificial
<220> FEATURE:
<223> OTHER INFORMATION: shRNA specific for Apelin

<400> SEQUENCE: 15
taacattctg tgattcttgg c                                              21

<210> SEQ ID NO 16
<211> LENGTH: 21
<212> TYPE: DNA
<213> ORGANISM: artificial
<220> FEATURE:
<223> OTHER INFORMATION: shRNA specific for Apelin

<400> SEQUENCE: 16
ttacaaacat tgaacacagg g                                              21

<210> SEQ ID NO 17
<211> LENGTH: 21
<212> TYPE: DNA
<213> ORGANISM: artificial
<220> FEATURE:
<223> OTHER INFORMATION: shRNA specific for Apelin

<400> SEQUENCE: 17
aacagggcct taatatcttt g                                              21

<210> SEQ ID NO 18
<211> LENGTH: 21
<212> TYPE: DNA
<213> ORGANISM: artificial
```

```
<220> FEATURE:
<223> OTHER INFORMATION: shRNA specific for Apelin

<400> SEQUENCE: 18
aagcagacca atctatggag g                                              21

<210> SEQ ID NO 19
<211> LENGTH: 21
<212> TYPE: DNA
<213> ORGANISM: artificial
<220> FEATURE:
<223> OTHER INFORMATION: shRNA specific for Apelin

<400> SEQUENCE: 19
tttctctgca ttcttccctg g                                              21

<210> SEQ ID NO 20
<211> LENGTH: 19
<212> TYPE: RNA
<213> ORGANISM: artificial
<220> FEATURE:
<223> OTHER INFORMATION: siRNA specific for GP130

<400> SEQUENCE: 20
cucacuugca acauucuua                                                 19

<210> SEQ ID NO 21
<211> LENGTH: 25
<212> TYPE: RNA
<213> ORGANISM: artificial
<220> FEATURE:
<223> OTHER INFORMATION: siRNA specific for APJ

<400> SEQUENCE: 21
acuaugacug gcccuuuggg accuu                                          25
```